(12) United States Patent
Goletz et al.

(10) Patent No.: US 9,700,610 B2
(45) Date of Patent: Jul. 11, 2017

(54) MICROORGANISMS CARRYING A TUMOR ANTIGEN

(75) Inventors: Steffen Goletz, Berlin (DE); Philippe Ulsemer, Berlin (DE); Kawe Toutounian, Berlin (DE)

(73) Assignee: Glycotope GmbH, Berlin (DE)

( * ) Notice: Subject to any disclaimer, the term of this patent is extended or adjusted under 35 U.S.C. 154(b) by 157 days.

(21) Appl. No.: 14/239,711

(22) PCT Filed: Aug. 22, 2012

(86) PCT No.: PCT/EP2012/066360
§ 371 (c)(1),
(2), (4) Date: Jun. 4, 2014

(87) PCT Pub. No.: WO2013/026887
PCT Pub. Date: Feb. 28, 2013

(65) Prior Publication Data
US 2014/0302093 A1      Oct. 9, 2014

Related U.S. Application Data

(60) Provisional application No. 61/526,054, filed on Aug. 22, 2011.

(30) Foreign Application Priority Data

Aug. 22, 2011  (EP) .................................. 11178322

(51) Int. Cl.
| | | |
|---|---|---|
| *A01N 63/00* | (2006.01) | |
| *A61K 39/02* | (2006.01) | |
| *C07K 16/12* | (2006.01) | |
| *C12N 1/20* | (2006.01) | |
| *C12R 1/01* | (2006.01) | |
| *A61K 39/00* | (2006.01) | |

(52) U.S. Cl.
CPC ...... *A61K 39/0216* (2013.01); *A61K 39/0011* (2013.01); *C07K 16/1257* (2013.01); *C12N 1/20* (2013.01); *C12R 1/01* (2013.01); *A61K 2039/5154* (2013.01); *A61K 2039/585* (2013.01)

(58) Field of Classification Search
CPC ......... C12N 1/00; C12N 1/20; A61K 39/0216
See application file for complete search history.

(56) References Cited

U.S. PATENT DOCUMENTS

| | | | |
|---|---|---|---|
| 4,931,275 A | 6/1990 | Shinitzky et al. | |
| 5,506,343 A | 4/1996 | Kufe | |
| 5,547,933 A | 8/1996 | Lin | |
| 5,683,674 A | 11/1997 | Taylor-Papadimitriou et al. | |
| 5,739,277 A | 4/1998 | Presta et al. | |
| 5,804,187 A | 9/1998 | do Couto et al. | |
| 5,948,646 A | 9/1999 | Srivastava | |
| 5,961,979 A | 10/1999 | Srivastava | |
| 6,168,793 B1 | 1/2001 | Srivastava | |
| 6,315,997 B1 | 11/2001 | do Couto et al. | |
| 6,984,384 B1 | 1/2006 | Subjeck et al. | |
| 7,268,120 B1 | 9/2007 | Horton et al. | |
| 7,595,192 B2 | 9/2009 | Goletz et al. | |
| 8,017,388 B2 | 9/2011 | Goletz et al. | |
| 8,088,357 B2 | 1/2012 | Goletz et al. | |
| 8,198,045 B2* | 6/2012 | DeFrees ................ | C12P 21/005 435/101 |
| 8,592,165 B2* | 11/2013 | Goletz ............... | C07K 16/3092 435/7.1 |
| 8,609,370 B2 | 12/2013 | Goletz et al. | |
| 8,642,276 B2 | 2/2014 | Goletz et al. | |
| 8,741,365 B2* | 6/2014 | Goletz ........................... | 426/34 |
| 8,795,746 B2* | 8/2014 | Sonnenburg ............ | A23L 1/296 426/71 |
| 8,887,358 B2* | 11/2014 | Cox et al. ......................... | 27/19 |
| 8,951,762 B2* | 2/2015 | Nikolau ................... | C12N 9/16 435/134 |
| 9,028,841 B2* | 5/2015 | Henn et al. ................ | 424/247.1 |
| 9,234,204 B2* | 1/2016 | Qvit-Raz ............. | C12N 15/746 |
| 9,494,587 B2 | 11/2016 | Goletz et al. | |
| 2002/0132771 A1 | 9/2002 | Madiyalakan | |
| 2004/0029127 A1 | 2/2004 | Postaire et al. | |
| 2004/0115177 A1 | 6/2004 | Harris et al. | |

(Continued)

FOREIGN PATENT DOCUMENTS

| | | |
|---|---|---|
| CN | 101560488 A | 10/2009 |
| DE | 4329004 A1 | 3/1995 |

(Continued)

OTHER PUBLICATIONS

Chassard, Christophe et al, International Journal of Systematic and Evolutionary Microbiology, 2008, vol. 58, pp. 1008-1013, *Bacteroides xylanisolvens* sp. nov., a xylan-degrading bacerium isolated from human feces.*

Sanchez, J. I. et al, Micrbial Biotechnology, 2009, vol. 2(1), pp. 101-113, Arabinoxylan-oligosaccharides (AXOS) affect the protein/carbohydrate fermentation balance and microbial population dynamics of the Simulator of Human Intestinal Microbial Ecosystem.*

Mirande, C et al, Journal of Applied Microbiology, epub Jan. 11, 2010, vol. 109, pp. 451-460, Dietary fibre degradation and fermentation by two xylanolytic bacteria Bacteroides xylanisolvens XB1At and Roseburia intestinalis XB6B4 from human intestine.*

Mirande, C et al, Journal of Applied Microbioligy, vol. 109, pp. 451-460, 2010.*

(Continued)

*Primary Examiner* — Albert Navarro

(74) *Attorney, Agent, or Firm* — Nelson Mullins Riley & Scarborough LLP; Jane E. Remillard, Esq.; Jill Gorny Sloper, Esq.

(57) ABSTRACT

The present invention pertains to microorganisms of the species *Bacteroides xylanisolvens* expressing a core-1 antigen on their surface. These microorganisms are in particular useful for the prophylaxis and treatment of core-1 positive diseases and are particularly characterized by a stable, homogenous high core-1 expression. Also provided are pharmaceutical compositions which comprise respective core-1 positive microorganisms or fractions thereof.

12 Claims, 11 Drawing Sheets

(56) References Cited

U.S. PATENT DOCUMENTS

Figure 1:
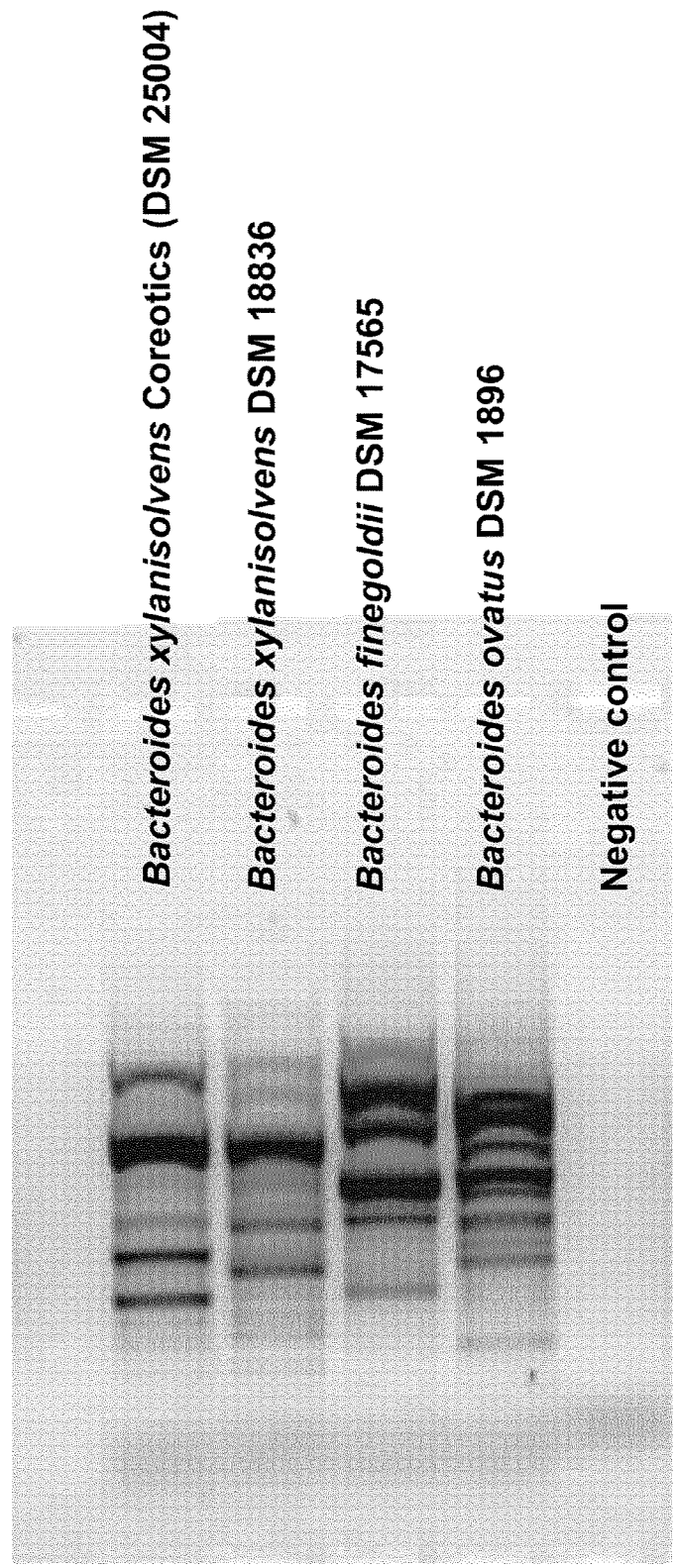

| | | |
|---|---|---|
| 2004/0265998 A1 | 12/2004 | Goletz et al. |
| 2005/0187378 A1 | 8/2005 | Kim |
| 2005/0203010 A1 | 9/2005 | Kim |
| 2006/0127419 A1 | 6/2006 | Goletz et al. |
| 2006/0251668 A1 | 11/2006 | Goletz et al. |
| 2006/0292129 A1* | 12/2006 | Goletz ............... A61K 39/0011 424/93.21 |
| 2007/0015239 A1 | 1/2007 | Bihoreau et al. |
| 2007/0016704 A1 | 1/2007 | Harari et al. |
| 2008/0226681 A1 | 9/2008 | Goletz et al. |
| 2008/0227689 A1* | 9/2008 | Marth ................ A01K 67/0276 514/1.1 |
| 2009/0311744 A1* | 12/2009 | DeFrees ............... C12P 21/005 435/69.1 |
| 2009/0324617 A1* | 12/2009 | Satomaa ........... A61K 39/0011 424/174.1 |
| 2010/0028947 A1 | 2/2010 | Goletz et al. |
| 2010/0158952 A1* | 6/2010 | Goletz ............... C07K 16/3092 424/243.1 |
| 2010/0297159 A1* | 11/2010 | Irazoqui ............. A61K 39/0011 424/185.1 |
| 2010/0303837 A1* | 12/2010 | Goletz ............... C07K 16/3092 424/184.1 |
| 2011/0076356 A1* | 3/2011 | Ziemer ..................... C12R 1/01 426/2 |
| 2011/0104692 A1* | 5/2011 | Rudi ...................... C12Q 1/689 435/6.12 |
| 2011/0129570 A1* | 6/2011 | Goletz ................. A23C 9/1203 426/61 |
| 2012/0128676 A1 | 5/2012 | Goletz et al. |
| 2012/0149877 A1 | 6/2012 | Goletz et al. |
| 2012/0207882 A1* | 8/2012 | Sonnenburg .............. A23L 1/30 426/71 |
| 2013/0303837 A1 | 11/2013 | Berka et al. |
| 2014/0302093 A1 | 10/2014 | Goletz et al. |
| 2016/0103022 A1 | 4/2016 | Rogers et al. |

FOREIGN PATENT DOCUMENTS

| | | | |
|---|---|---|---|
| EP | 0117060 A2 | 8/1984 | |
| EP | 1167537 A1 | 1/2002 | |
| EP | 1371735 A1 | 12/2003 | |
| EP | 1920781 * | 5/2008 | ............ A61K 39/02 |
| EP | 1920781 A1 | 5/2008 | |
| WO | 9215682 A1 | 9/1992 | |
| WO | 93/20841 A1 | 10/1993 | |
| WO | 9429469 A2 | 12/1994 | |
| WO | 9700957 A1 | 1/1997 | |
| WO | 97/30087 A1 | 8/1997 | |
| WO | 9740182 A1 | 10/1997 | |
| WO | 9929834 A1 | 6/1999 | |
| WO | 0041576 A1 | 7/2000 | |
| WO | 0052135 A2 | 9/2000 | |
| WO | 01/12217 A1 | 2/2001 | |
| WO | 02/44217 A1 | 6/2002 | |
| WO | 03016329 A2 | 2/2003 | |
| WO | 03/023023 A1 | 3/2003 | |
| WO | 03035636 A2 | 5/2003 | |
| WO | 03044051 A1 | 5/2003 | |
| WO | 2004009632 A2 | 1/2004 | |
| WO | 2004018659 A1 | 3/2004 | |
| WO | 04/050707 A2 | 6/2004 | |
| WO | 2004/050707 A2 | 6/2004 | |
| WO | 2005003773 A1 | 1/2005 | |
| WO | 2005/016962 A2 | 2/2005 | |
| WO | 2005017130 A2 | 2/2005 | |
| WO | 2005040221 A1 | 5/2005 | |
| WO | 2005080585 A1 | 9/2005 | |
| WO | 2005108423 A1 | 11/2005 | |
| WO | 2006/012626 A2 | 2/2006 | |
| WO | 2006012616 A2 | 2/2006 | |
| WO | 2007124992 A1 | 11/2007 | |
| WO | 2008/055703 Querry * | 1/2008 | |
| WO | 2008/028686 A2 | 3/2008 | |
| WO | 2008/055702 * | 5/2008 | ............ A61K 39/02 |
| WO | 2008/055703 * | 5/2008 | ............ C07K 16/30 |
| WO | 2008/055703 A2 | 5/2008 | |
| WO | 2008055702 A1 | 5/2008 | |
| WO | 2009/138220 A1 | 11/2009 | |
| WO | 2013026887 A1 | 2/2013 | |

OTHER PUBLICATIONS

Jager, G. et al., "Treatment of Extranodal Marginal Zone B-Cell Lymphoma of Mucosa-Associated Lymphoid Tissue TYpe with Cladribine: A Phase II Study," Journal of Clinical Oncology, vol. 20, Issue 18, pp. 3872-3877 (2002).

Jensen, K. et al., "Functional Improvement of Antibody Fragments Using a Novel Phage Coat Protein III Fusion System," Biochemical and Biophysical Research Communications, vol. 298, Issue 4, pp. 566-573 (2002).

Jeschke, U. et al., "Expression of the Thomsen-Friedenreich Antigen and of its Putative Carrier Protein Mucin 1 in the Human Placenta and in Trophoblast Cells In Vitro," Histochemistry and Cell Biology, vol. 117, No. 3, pp. 219-226 (2002).

Jones, M. et al. "Characterization of the cellular uptake and metabolic conversion of acetylated N-acetylmannosamine (ManNAc) analogues to sialic acids," Biotechnology and Bioengineering, 85 (4): 394-405 (2004).

Kalka-Moll, W. et al., "Zwitterionic Polysaccharides Stimluate T Cells by MHC Class II-Dependent Interactions," The Journal of Immunology, vol. 169, pp. 6149-6153 (2002).

Kanda Yutaka, et al., "Comparison of Cell Lines for Stable Production of Fucose-Negative Antibodies with Enhanced ADCC," Biotechnology and Bioengineering, Jul. 2006, vol. 94, No. 4, pp. 680-688.

Kaneko, Y., et al., "Anti-Inflammatory Activity of Immunogloubulin G Resulting from FC Sialylation," Science, American Association for the Advancement of Science, Aug. 2006, vol. 313, No. 5787, p. 671.

Karsten, U. et al., "A New Monoclonal Antibody (A78-GIA7) to the Thomsen-Friedenreich Pan-Tumor Antigen," Hybridoma, vol. 14, No. 1, pp. 37-44 (1995).

Karsten, U. et al., "Enhanced Binding of Antibodies to the DTR Motif of MUC1 Tandem Repeat Peptide is Mediated by Site-Specific Glycosylation," Cancer Research, vol. 48, pp. 2541-2549 (1998).

Keppler, O. et al. "UDP-GicNac 2-Epimerase: A Regulator of Cell Surface," Science 284: 1372-1376 (1999).

Klaamas, K., et al., "Expression of Tumor-Associated Thomsen-Friedenreich Antigen (T AG) in Helicobacter Pylori and Modulation of T AG Specific Immune Response in Infected Individuals," Immunological Investigations, vol. 31, No. 3/4, pp. 191-204(2002).

Kotera, Y. et al., "Comparative Analysis of Necrotic and Apoptotic Tumor Cells as a Source of Antigen(s) in Dendritic Cell-Based Immunization," Cancer Research, vol. 51, pp. 8105-8109 (2001).

Kozak, R. et al., "Nature of the Bifunctional Chelating Agent Used for Radioimmunotherapy with Yttrium-90 Monoclonal Antibodies: Critical Factors in Determining in Vivo Survival and Organ Toxicity," Cancer Research, vol. 49, pp. 2639-2644 (1989).

Kunz, H., "Synthetic Glycopeptides for the Development of Tumor-Selective Vaccines," Journal of Peptide Science, vol. 9, pp. 563-573 (2003).

Kurtenkov, O., et al., "Better Survival of Helicobacter Pylori Infected Patients With Early Gastric Cancer Is Related to a Higher Level of Thomsen-Friedenreich Antigen-Specific Antibodies," Immunological Investigations, vol. 32, No. 1-2, pp. 89-93(2003).

Lazar, E. et al., "Transforming Growth Factor Alpha: Mutation of Aspartic Acid 47 and Leucine 48 Results in Different . Biological Activities," Molecular and Cellular Biology, vol. 8, pp. 1247-1252 (1988).

Leffell, M., "An Overview of the Immune System: The Molecular Basis for Immune Responses," Human Immunology Handbook, Chapter 1, pp. 1-45 (1997).

Liao, K-W. et al., "Design of Transgenes for Efficient expression of Active Chimeric Proteins on Mammalian Cells," Biotechnology and Bioengineering, vol. 73, Issue 4, pp. 313-323 (2001).

(56) References Cited

OTHER PUBLICATIONS

Libyh, M. et al., "A Recombinant Human scFv Anti-Rh(D) Antibody with Multiple Valences Using a C-Terminal Fragment of C4-Binding Protein," Blood, vol. 90, No. 10, pp. 3978-3983 (1997).
Linardou, H. et al., "Deoxyribonuclease I (DNase I)," Cell Biophysics vols. 24/25, pp. 243-248 (1994).
Lozzio, C. et al., "Human Chronic Myelogenous Leukemia Cell-Line with Positive Philadelphia Chromosome," Blood, vol. 45, No. 3, pp. 321-334 (1975).
Luftig, R., Microbiology and Immunology, Lippincott-Raven Publishers, Philadelphia, pp. 228-229 (1998).
MacCallum, R. et al., "Antibody-Antigen Interactions: Contact Analysis and Binding Site Topography," Journal of Molecular Biology, vol. 262, Issue 5, pp. 732-745 (1996).
Mach, N. et al., "Cytokine-Secreting Tumor Cell Vaccines," Current Opinion Immunology, vol. 12, pp. 571-575 (2000).
Mantey, L. et al. "Efficient Biochemical Engineering of Cellular Sialic Acids Using an Unphysiological Sialic Acid Precursor in Cells Lacking UDP-N-acetylglucosamine 2-epimerase," FEBS Letters, 503, NR-1: 80-84 (2001).
Marshall, VM "Gut-Derived Organisms for Milk Fermentation," Journal of Chemical Technology and Biotechnology, 51 (4): 548-553 (1991).
Martin, A. et al., "Structural Families in Loops of Homologous Proteins: Automatic Classification, Modelling and Application to Antibodies," Journal of Molecular Biology, vol. 263, Issue 5, pp. 800-815 (1996).
Matsumoto-Takasaki et al, BioScience Trends. 2009; 3(3):87-95.
Matsuzaki, T., et al., "Antitumor Effect of Intrapleural Administration of Lactobacillus-casei in Mice," Cancer Immunology Immunotherapy, vol. 26, No. 3, pp. 209-214 (1988).
Matzinger, P., "Tolerance, Danger, and the Extended Family," Annual Review in Immunology, vol. 12, pp. 991-1045 (1994).
Mazmanian, S. et al., "The Love-Hate Relationship Between Bacterial Polysaccharides and the Host Immune System," Nature Reviews, vol. 6, pp. 849-858 (2006).
Melcher, A. et al., "Apoptosis or Necrosis for Tumor Immunotherapy: What's in a Name?," Journal of Molecular Medicine, vol. 77, pp. 824-833 (1999).
Melcher, A. et al., "Tumor Immunogenicity is Determined by the Mechanism of Cell Death Via Induction of Heat Shock Protein Expression," Nature Medicine, vol. 4, No. 5, pp. 581-587 (1998).
Mise, K. et al., "Effect of Heat Treatment on Tumor Cells and Antitumor Effector Cells," Cancer Research, vol. 59, pp. 6199-6202 (1990).
Mitchell, M. et al., "Active Specific Immunotherapy for Melanoma: Phase I Trial of Allogeneic Lysates and a Novel Adjuvant," Cancer Research, vol. 48, pp. 5883-5893 (1988).
Mivechi, N., "Heat Sensitivity, Thermotolerance, and Profile of Heat Shock Protein Synthesis of Human Myelogenous Leukemias," Cancer Research, vol. 49, pp. 1954-1958 (1989).
Mondovi, B. et al., "Increased Immunogenicity of Ehrlich Ascites Cells After Heat Treatment," Cancer, vol. 20, No. 4, pp. 885-888 (1972).
Morrison, S. et al., "Complement Activation and Fc Receptor Binding by IgG," Protein Engineering of Antibody Molecules for Prophylactic and Therapeutic Applications in Man, Clark, M., Ed., pp. 101-113 (1993).
MSNBC News Services, "Mixed Results on New Cancer Drug," Nov. 9, 2000.
Muramatsu et al., "Glycoprotein-Bound Large Carbohydrates of Early Embryonic Cells: Structural Characteristic of the Glycan Isolated from F9 Carcinoma Cells," J. Biochem. 94:799-810 (1983).
Natali, P. et al., "Heterogeneity in the Expression of HLA and Tumor Associated Antigens by Surgically Removed and Cultured Breast Carcinoma Cells," Cancer Research, vol. 43, pp. 660-668 (1983).
Nicaise, M. et al., "Affinity Transfer by CDR Grafting on a Nonimmunoglobulin Scaffold," Protein Science, vol. 13, Issue 7, pp. 1882-1891 (2004).

Novina, C. et al., "siRNA-Directed Inhibition of HIV-1 Infection," Nature Medicine, vol. 8, No. 7, pp. 681-686 (2002).
Nuttall, S. et al., "Design and Expression of Soluble CTLA-4 Variable Domain as a Scaffold for the Display of Functional Polypeptides," Proteins: Structure, Function, and Genetics, vol. 36, Issue 2, pp. 217-227 (1999).
Nygren, P-A. et al., "Scaffolds for Engineering Novel Binding Sites in Proteins," Current Opinion in Structural Biology, vol. 7, Issue 4, pp. 463-469 (1997).
Ohyama, C. et al., "Dual Roles of Sialyl Lewis X Oligosaccharides in Tumor Metastasis and Rejection by Natural Killer Cells," The EMBO Journal, vol. 18, No. 6, pp. 1516-1525 (1999).
Ohyama, C. et al., "Natural Killer Cells Attack Tumor Cells Expressing High Levels of Sialyl Lewis X Oligosaccharides," PNAS, vol. 99, No. 21, pp. 13789-13794 (2002).
Olsvik, O. et al., "Magnetic Separation Techniques in Diagnostic Microbiology," Clinical Microbiology Reviews, vol. 7, No. 1, pp. 43-54 (1994).
Ouagari, K. et al., "Glycophorin a Protects K562 Cells from Natural Killer Cell Attack," The Journal of Biological Chemistry, vol. 270, No. 45, pp. 26970-26975 (1994).
Owens, G. et al., "Identification of Two Short Internal Ribosome Entry Sites Selected from Libraries of Random Oligonucleotides," PNAS, vol. 98, No. 4, pp. 1471-1476 (2001).
Paddison, P. et al., "Short Hairpin RNAs (shRNAs) Induce Sequence-Specific Silencing in Mammalian Cells," Genes & Development, vol. 16, pp. 948-958 (2002).
Pahlsson, P. et al., "Biochemical Characterization of the O-Glycans on Recombinant Glycophorin a Expressed in Chinese Hamster Ovary Cells," Glycoconjugate Journal, vol. 11, pp. 43-50 (1994).
Panka, D. et al., "Variable Region Framework Differences Result in Decreased or Increased Affinity of Variant Anti-Digoxin Antibodies," PNAS, vol. 85, No. 9, pp. 3080-3084 (1988).
Paul, W., Ed., Fundamental Immunology, Second Edition, Raven Press, New York, pp. 1007-1009 (1989).
Peach, R. et al., "Complementarity Determining Region 1 (CDR1)- and CDR3-Analogous Regions in CTLA-4 and CD28 Determine the Binding to B7-1," Journal of Experimental Medicine, vol. 180, No. 6, pp. 2049-2058 (1994).
Peters, L. et al., "Preparation of Immuno-Therapeutic Autologous Tumor Cell Vaccines from Solid Tumors," Cancer Research, vol. 39, pp. 1353-1360 (1979).
Phillips, T., Analytical Techniques in Immunochemistry, Marcel Dekker, New York, pp. 307-310 (1992).
Price, M. et al., "Effect of Heat and Glutaraldehyde Upon the Immunogenicity of Meth a Sarcoma Cells," The British Journal of Cancer, vol. 40, pp. 663-665 (1979).
Price, M. et al., "Summary Report on the ISOBM TD-4 Workshop: Analysis of 56 Monoclonal Antibodies Against the MUC1 Mucin," Tumor Biology, vol. 19, Suppl. 1, pp. 1-20 (1998).
Raska, Milan et al., "Glycosylation patterns of HIV-1 gp120 Depends on he Type of Expressing Cells and Affect Anitbody Recognition," The Journal of Biological Chemistry, vol. 285(27):20860-20869 (2010).
Ravn et al, Cancer Immunol Immunother (2007) 56:1345-1357.
Restifo, N., "Building Better Vaccines: How Apoptotic Cell Death Can Induce Inflammation and Activate Innate and Adaptive Immunity," Current Opinion in Immunology, vol. 12, pp. 597-603 (2000).
Riemer AB et al. "Induction of IgG antibodies against the GD2 carbohydrate tumor antigen by vaccination with peptide mimotopes," European Journal of Immunology, 36(5): 1267-1274 (2006).
Romani, N. et al., "Proliferating Dendritic Cell Progenitors in Human Blood," Journal of Experimental Medicine, vol. 180, pp. 83-93 (1994).
Rooman, M. et al., "Amino Acid Sequence Templates Derived from Recurrent Turn Motifs in Proteins: Critical Evaluation of Their Predictive Power," Protein Engineering, vol. 3, No. 1, pp. 23-27 (1989).
Rudikoff, S. et al., "Single Amino Acid Substitution Altering Antigen-Binding Specificity," PNAS, vol. 79, No. 6, pp. 1979-1983 (1982).

(56) References Cited

OTHER PUBLICATIONS

Saerens, D. et al., "Identification of a Universal VHH Framework to Graft Non-Canonical Antigen-Binding Loops of Camel Single-Domain Antibodies," Journal of Molecular Biology, vol. 352, Issue 3, pp. 597-607 (2005).
Samali, A. et al., "Thermotolerance and Cell Death are Distinct Cellular Responses to Stress: Dependence on Heat Shock Proteins," FEBS Letters, vol. 461, pp. 306-310 (1999).
Santegoets, S. et al., "In Vitro Priming of Tumor-Specific Cytotoxic T Lymphocytes Using Allogeneic Dendritic Cells Derived from the Human Mutz-3 Cell Line," Cancer Immunology Immunotherapy, vol. 55, No. 12, pp. 1480-1490 (2006).
Sauter, B. et al., "Consequences of Cell Death: Exposure to Necrotic Tumor Cells, but Not Primary Tissue Cells or Apoptotic Cells, Induces the Maturation of Immunostimulatory Dendritic Cells," Journal of Experimental Medicine, vol. 191, No. 3, pp. 423-433 (2000).
Scheibel, T. et al., "Contribution of N- and C-Terminal Domains to the Function of Hsp90 in *Saccharomyces cerevisiae*," Molecular Microbiology, vol. 34, No. 4, pp. 701-713 (1999).
Schild, H. et al., "gp96—The Immune System's Swiss Army Knife," Nature Immunology, vol. 1, No. 2, pp. 100-101 (2000).
Schlom, J., "Monoclonal Antibodies: They're More and Less Than you Think," Molecular Foundations of Oncology, Broder, S., Ed., Chapter 6, pp. 95-134 (1991).
Schneider, D. et al., "Thermostability of Membrane Protein Helix-Helix Interaction Elucidated by Statistical Analysis," FEBS Letters, vol. 532, No. 1-2, pp. 231-236 (2002).
Schneider, F. et al., "Overexpression of Sialyltransferase CMP-Sialic Acid: Gal.beta.1 ,3BaINAc-R .alpha.6- Sialyltransferase is Related to Poor Patient Survival in Human Colorectal Carcinomas," Cancer Research, vol. 61, No. 11, pp. 4605-4611 (2001).
Selawry, O. et al., "Hyperthermia Tissue-Cultured Cells of Malignant Origin," Cancer Research, vol. 17, pp. 785-791 (1957).
Sensi, M. et al., "Clonal Expansion of Lymphocytes in Human Melanoma Metastases After Treatment with a Hapten-Modified Autologous Tumor Vaccine," Journal of Clinical Investigation, vol. 99, No. 4, pp. 710-717 (1997).
Shaif-Muthana, M. et al., "Dead or Alive: Immunogenicity of Human Melanoma Cells When Presented by Dendritic Cells," Cancer Research, vol. 60, pp. 6441-6447 (2000).
Shinkawa, T. et al. "The Absence of Fucose but Not the Presence of Galactose or Bisecting N-Acetylglucosamine of Human IgG1 Complex-type Oligosaccharides Shows the Critical Rile of Enhancing Antibody-dependent Cellular Cytotoxicity," The Journal ofBiological Chemistry, 278(5): 3466-3473 (2003).
Sigma-Aldrich catalog, Granulocyte Macrophage Colony-Stimulating Factor Human, dowloaded 2011.
Sivanandham, M. et al., "Cancer Vaccines: Clinical Applications," Principles and Practice of the Biologic Therapy of Cancer, Third Edition, Lippincott Williams & Wilkins, Philadelphia, Pennsylvania, pp. 632-647 (2000).
Skerra, A., "Alternative Non-Antibody Scaffolds for Molecular Recognition," Current Opinion in Biotechnology, vol. 18, Issue 4, pp. 295-304 (2007).
Skerra, A., "Engineered Protein Scaffolds for Molecular Recognition," Journal of Molecular Recognition, vol. 13, Issue 4, pp. 167-187 (2000).
Snippe, H. et al., "Adjuvant Directed Immune Specificity at the Epitope Level: Implications for Vaccine Development, A Model for Using Semliki Forest Virus Infection of Mice," Vaccine Design: The Role of Cytokine Networks, Gregoriadis, G. et al.,Eds., Plenum Press, New York pp. 155-166 (1997).
Somersan, S. et al., "Primary Tumor Tissue Lysates are Enriched in Heat Shock Proteins and Induce the Maturation of Human Dendritic Cells," The Journal of Immunology, vol. 167, pp. 4844-4852 (2001).
Springer, G., "Immunoreactive T and Tn Epitopes in Cancer Diagnosis, Prognosis and Immunotherapy," Journal of Molecular Medicine, vol. 75, pp. 594-602 (1997).
Stimmel, J. et al., "Yttrium-90 Chelation Properties of Tetraazatetraacetic Acid Macrocycles, Diethylenetriaminepentaacetic Acid Analogs, and a Novel Terpyridine Acyclic," Bioconjugate Chemistry, vol. 6, Issue 2, pp. 219-225 (1995). cited byapplicant.
Suzuki, T. et al., "A Comparison of the Genotoxicity of Ethylnitrosourea and Ethyl Methanesulfonate in lacZ Transgenic Mice (Muta.TM. Mouse)," Mutation Research, vol. 395, pp. 75-82 (1997).
Tachibana et al; (Cytotechnology, 1991, vol. 6, pp. 219-226).
Takahashi et al., "Antitumor Effects of the Intravesical Instillation of Heat Killed Cells of the Lactobacillus casei Strain Shirota on the Murine Orthotopic Bladder Tumor Mbt-2," Journal of Urology, vol. 166, No. 6, pp. 2506-2511 (2001).
Takano, Y., et al., "Lymph Node Metastasis-Related Carbohydrate Epitopes of Gastric Cancer With Submucosal Invasion," Surgery Today 2000, vol. 30, No. 12, pp. 1073-1082 (2000).
Thatcher, N. et al., "Anti-T Antibody in Malignant Melanoma Patients, Influence of Response Survival Following Chemotherapy—Changes in Serum Levels Following C parvum, BCG Immunization," Cancer, vol. 46, No. 6, pp. 1378-1382 (1980).
Todryk, S. et al., "Heat Shock Protein 70 Induced During Tumor Cell Killing Induces Th1 Cytokines and Targets Immature Dendritic Cell Precursors to Enhance Antigen Uptake," The Journal of Immunology, vol. 163, pp. 1398-1408 (1999).
Vajdos, F. et al., "Comprehensive Functional Maps of the Antigen-Binding Site of an Anti-ErbB2 Antibody Obtained with Shotgun Scanning Mutagenesis," Journal of Molecular Biology, vol. 320, Issue 2, pp. 415-428 (2002).
Van Rinsum, J. et al., "Specific Inhibition of Human Natural Killer Cell-Mediated Cytotoxicity by Sialic Acid and Sialo-Oligosaccharides," International Journal of Cancer, vol. 38, pp. 915-922 (1986).
Verma, I. et al., "Gene Therapy—Promises, Problems and Prospects," Nature, vol. 389, pp. 239-242 (1997).
Vermes, I. et al., "A Novel Assay for Apoptosis Flow Cytometric Detection of Phosphatidylserine Expression on Early Apoptotic Cells Using Fluorescein Labelled Annexin V," Journal of Immunological Methods, vol. 184, pp. 39-51 (1995).
Viswanatha, K. et al. "Engineering sialic acid synthetic ability into insect cells: identifying metabolic bottlenecks and devising strategies to overcome them," Biochemistry 42(51): 15215-15225 (2003).
Voshol, H. et al., "Cell Surface Glycoconjugates as Possible Targets for Human Natural Killer Cells: Evidence Against the Involvement of Glycolipids an N-Linked Carbohydrate Chains," Gylcobiology, vol. 3, No. 1, pp. 69-76 (1993).
Wang, Q. et al., "Second-Generation Adenovirus Vectors," Nature Medicine, vol. 2, No. 6, pp. 714-716 (1996).
U.S. Appl. No. 12/514,248, filed Nov. 25, 2009, Steffen Goletz.
U.S. Appl. No. 12/514,200, filed Nov. 11, 2009, Steffen Goletz.
U.S. Appl. No. 12/991,827, filed Jan. 28, 2011, Steffen Goletz.
U.S. Appl. No. 12/514,248, filed Oct. 1, 2015, N. Minnifield.
U.S. Appl. No. 12/514,248, filed Dec. 26, 2014, N. Minnifield.
U.S. Appl. No. 12/514,248, filed Apr. 11, 2013, N. Minnifield.
U.S. Appl. No. 12/514,248, filed Sep. 21, 2012, N. Minnifield.
U.S. Appl. No. 12/514,200, filed Jun. 21, 2013, B. Gangle.
U.S. Appl. No. 12/514,200, filed Feb. 22, 2013, B. Gangle.
U.S. Appl. No. 12/514,200, filed Sep. 18, 2012, B. Gangle.
U.S. Appl. No. 12/514,200, filed Nov. 30, 2011, B. Gangle.
U.S. Appl. No. 12/991,827, filed Jan. 30, 2014, K. Srivastava.
U.S. Appl. No. 12/991,827, filed Nov. 19, 2013, K. Srivastava.
U.S. Appl. No. 12/991,827, filed Mar. 18, 2013, K. Srivastava.
Wells, A. et al., "Heat Shock Proteins, Tumor Immunogenicity and Antigen Presentation: An Integrated View," Immunology Today, vol. 21, No. 3, pp. 129-132 (2000).
Werkmeister, J. et al., "Modulation of K562 Cells with Sodium Butyrate. Association of Impaired NK Susceptibility with Sialic Acid and Analysis of Other Parameters," International Journal of Cancer, vol. 32, pp. 71-78 (1983).
Wu, H. et al., "Humanization of a Murine Monoclonal Antibody by Simultaneous Optimization of Framework and CDR Residues," Journal of Molecular Biology, vol. 294, Issue 1, pp. 151-162 (1999).

(56) References Cited

OTHER PUBLICATIONS

Wu, S. et al., "Conformation of Complementarity Determining Region L1 Loop in Murine IgG .lamda. Light Chain Extends the Repertoire of Canonical Forms," Journal of Molecular Biology, vol. 229, Issue 3, pp. 597-601 (1993).

Yoshima, T. et al., "Heat Shock Factor 1 Mediates Hemin-Induced hsp70 Gene Transcription in K562 Erythroleukemia Cells," The Journal of Biological Chemistry, vol. 273, No. 39, pp. 25466-25471 (1998).

Yu, J-Y. et al., "RNA Interference by Expression of Short-Interfering RNAs and Hairpin RNAs in Mammalian Cells," Proceedings of the National Academy of Sciences, vol. 99, No. 9, pp. 6047-6052 (2002).

Zhang, S. et al., "Selection of Tumor Antigens as Targets for Immune Attack Using Immunohistochemistry: II. Blood Group-Related Antigens," International Journal of Cancer, vol. 73, pp. 50-56 (1997).

"Sequence 628 from Patent WO 2005/016962," (2005) XP002430727.

Agrawal, B. et al., "Cancer-Associated MUC1 Mucin Inhibits Human T-Cell Proliferation, which is Reversible by IL-2," Nature Medicine, vol. 4, No. 1, pp. 43-49 (1998).

Albert, M. et al., "Dendritic Cells Acquire Antigen from Apoptotic Cells and Induce Class I-Restricted CTLs," Nature, vol. 392, pp. 86-89 (1998).

Allison, A., "The Role of Cytokines in the Action of Immunological Adjuvants," Vaccine Design: The Role of Cytokine Networks, Gregoriadis, G. et al., Eds., NATO ASI Series A: Life Sciences, vol. 293, pp. 1-9, Plenum Press (1997).

Anderson, W., "Human Gene Therapy," Science, vol. 256, pp. 808-813 (1992).

Bagshawe, K. et al., "Antibody-Directed Enzyme Prodrug Therapy (ADEPT) for Cancer," Expert Opinion on Biological Therapy, vol. 4, No. 11, pp. 1777-1789(2004).

Bain et al, PLoS One, Sep. 2011, 6/9: e25007, 10 pages.

Baumeister and Goletz, "Voll Funktionsfahige Humane Dendritische Zelllinie," Laborwelt [online], vol. 6, 2005, pp. 1-6.

Baumeister et al, "GlycoExpress: a novel expression system for the optimal glycosylation of biotherapeutics," Specialty Chemicals Magazine, 25: 46-48 (2005).

Baumeister, "A novel expression system for production of higher active biotherapeutics with optimised glycosylation," PharmaChem, 5(4): 21-24 (2006).

Baumeister, H., "Glycoengineering—a Technology for Production of Glycoproteins," Journal of Biotechnology, Nov. 2004, pp. 10-11.

Benoist, H. et al., "Studies on the Susceptibility to Nk-Mediated Lysis and the Simultaneous Expression of Various Surface Molecules in Anthracyclin-Treated K562 Cells and in Four K562 Cell Clones," Immunology Letters, vol. 34, pp. 45-55 (1992).

Berd, D. et al., "Autologous Hapten-Modified Melanoma Vaccine as Postsurgical Adjuvant Treatment After Resection of Nodal Metastases," Journal of Clinical Oncology, vol. 15, No. 6, pp. 2359-2370 (1997).

Berthier-Vergnes, O. et al., "Induction of IgG Antibodies Directed to a M.sub.r 31,000 Melanoma Antigen in Patients Immunized with Vaccinia Virus Melanoma Oncolysates," Cancer Research, vol. 54, pp. 2433-2439 (1994).

Binder, R. et al. "Cutting Edge: Heat Shock Protein gp96 Induces Maturation and Migration of CD11c.sup.+ Cells in Vivo," The Journal of Immunology, vol. 165, pp. 6029-6035 (2000).

Boel, E. et al., "Functional Human Monoclonal Antibodies of All Isotypes Constructed from Phage Display Library-Derived Single-Chain Fv Antibody Fragments," Journal of Immunological Methods, vol. 239, Issues 1-2, pp. 153-166 (2000).

Bohm, C. et al., "Carbohydrate Recognition on MUC1-Expressing Targets Enhances Cytotoxicity of a T Cell Subpopulation," Scandinavian Journal of Immunology, vol. 46, pp. 27-34 (1997).

Bomford, R. et al., "The Control of the Antibody Isotype Response to Recombinant Human Immunodeficiency Virus gp120 Antigen by Adjuvants," Aids Research and Human Retroviruses, vol. 8, No. 10, pp. 1765-1771 (1992).

Bonig et al. "Gylcosylated vs non-glycosylated granulocyte colony-stimulating factor (G-CSF)—results of a prospective randomised mononcentre study," Bone Marrow Trans. 25: 259-264 (2001).

Bourdon, G., "Inhibition of Tumoral Graft Growth by Pretreatment with Normal or Heat-Modified Tumoral Cells," Annales D'Immunologie, vol. 132, No. 1, pp. 43-63 (1981).

Brechbiel, M. et al., "Synthesis of 1-(p-Isothiocyanatobenzyl) Derivatives of Dtpa and Edta. Antibody Labeling and Tumor-Imaging Studies," Inorganic Chemistry, vol. 25, No. 16, pp. 2772-2781 (1986).

Brummelkamp, T. et al., "A System for Stable Expression of Short Interfering RNAs in Mammalian Cells," Science, vol. 296, pp. 550-553 (2002).

Burgess, W. et al., "Possible Dissociation of the Heparin-Binding and Mitogenic Activities of Heparin-Binding (Acidic Fibroblast) Growth Factor-1 from its Receptor-Binding Activities by Site-Directed Mutagenesis of a Single Lysine Residue," TheJournal of Cell Biology, vol. 111, No. 5, pp. 2129-2138 (1990).

Butschak, G., et al., "Isolation and Characterization of Thomsen-Friedenreich-Specific Antibodies From Human Serum," Tumor Biology, vol. 23, No. 3, pp. 113-122 (2002).

Cao, Y. et al., "Expression of CD175 (Tn), CD175s (Sialosyl-Tn) and CD176 (Thomsen-Friedenreich Antigen) on Malignant Human Hematopoietic Cells," International Journal of Cancer, vol. 123, pp. 89-99 (2008).

Cao, Y. et al., "Immunodetection of Epithelial Mucin (MUC1, MUC3) and Mucin-Associated Glycotopes (Tf, Tn, and Sialosyl-Tn) in Benign and Malignant Lesions of Colonic Epithelium Apolar Localization Corresponds to Malignant Transformation," VirchowsArchiv, vol. 431, pp. 159-166 (1997).

Carbone, M. et al., "Multistep and Multifactorial Carcinogenesis: When Does a Contributing Factor Become a Carcinogen?," Seminars in Cancer Biology, vol. 14, pp. 399-405 (2004).

Casset, F. F et al., "A Peptide Mimetic of an Anti-CD4 Monoclonal Antibody by Rational Design," Biochemical and Biophysical Research Communications, vol. 307, Issue 1, pp. 198-205 (2003).

Cavaliere, R. et al., "Selective Heat Sensitivity of Cancer Cells. Biochemical and Clinical Studies," Cancer, vol. 20, No. 9, pp. 1351-1381 (1967).

Check, J. et al., "Protection Against Transplanted and Spontaneous Lymphoma by Inoculation of Heat-Altered Syngeneic Tumor Cells in Splenectomized Mice," Cancer, vol. 34, No. 1, pp. 197-203 (1974).

Chen, Y. et al., "Selection and Analysis of an Optimized Anti-Vegf Antibody: Crystal Structure of an Affinity-Matured Fab in Complex with Antigen," Journal of Molecular Biology, vol. 293, Issue 4, pp. 865-881 (1999).

Chen, Z. et al., "Efficient Antitumor Immunity Derived from Maturation of Dendritic Cells that had Phagocytosed ApoptoticlNecrotic Tumor Cells," International Journal of Cancer, vol. 93, No. 4, pp. 539-548 (2001).

Chothia, C. et al. "Canonical Structures for the Hypervariable Regions of Immunoglobulins," Journal of Molecular . Biology, vol. 196, Issue 4, pp. 901-917 (1987).

Chothia, C. et al., "Conformations of Immunoglobulin Hypervariable Regions," Nature, vol. 342, pp. 877-883 (1989).

Chothia, C. et al., "Structural Repertoire of the Human V.sub.h Segments," Journal of Molecular Biology, vol. 227, Issue 3, pp. 799-817 (1992).

Chothia, C. et al., "The Predicted Structure of Immunoglobulin D1.3 and its Comparison with the Crystal Structure," Science, vol. 233, pp. 755-758 (1986).

Clayman, C., Ed., The American Medical Association Encyclopedia of Medicine, Random House, New York, pp. 573-574, 576, and 1034 (1989).

Cox, J. et al., "Adjuvants—-A Classification and Review of Their Modes of Action," Vaccine, vol. 15, No. 3, pp. 248-256 (1997).

(56) References Cited

OTHER PUBLICATIONS

Cox, J. et al., "Development of an Influenza-ISCOM.TM. Vaccine," Vaccine Design: The Role of Cytokine Networks, Gregoriadis, G. et al., Eds., Plenum Press, New York, pp. 33-49 (1997).

Croce, M.V., et al., "The Use of Carbohydrate Antigens for the Preparation of Vaccines for Therapy in Breast Cancer," Drugs of Today, vol. 38, No. 11, pp. 759-768 (2002).

Cryz, S., Ed., Immunotherapy and Vaccines, pp. 3-11, VCH, Weinheim, Germany (1991).

Czuczman, M. et al., "Treatment of Patients with Low-Grade B-Cell Lymphoma with the Combination of Chimeric Anti-CD20 Monoclonal Antibody and Chop Chemotherapy," Journal of Clinical Oncology, vol. 17, No. 1, pp. 268-276 (1999).

Dai, J. et al., "Effect of Desialyation on Binding, Affinity, and Specificity of 56 Monoclonal Antibodies Against MUC1 Mucin," Tumor Biology, vol. 19, pp. 100-110 (1998).

Dall'Olio, F. et al., "Expression of .beta.-Galactoside .alpha.2,6-Sialyltransferase Does Not Alter the Susceptibility of Human Colon Cancer Cells to Nk-mediated Cell Lysis," Gycobiology, vol. 7, No. 4, pp. 507-513 (1997).

De' Pascalis, R. et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Innmunology,vol. 169, pp. 3076-3084 (2002).

Dermer, G., "Another Anniversary for the War on Cancer," BiolTechnology, vol. 12, p. 320 (1994).

Dickson, J., "Hyperthermia in the Treatment of Cancer," Lancet, vol. 1, pp. 202-205 (1979).

Dictionary of Immunology, Herbert, W. et al., Eds., Third Edition, Blackwell Scientific Publications, Oxford, pp. 3, 7, 46, 87-88, 94, 97, 105, and 116 (1985).

Dorai, H., et al., "The Effect of Dihydrofolate Reductase-Mediated Gene Amplification on the Expression of Transfected Immunoglobulin Genes," Journal of Immunology (Baltimore, Md. 1950), Dec. 15, 1987, vol. 139, No. 12, pp. 4232-4241.

Dressel, R. et al., "Heat Shock Protein 70 is Able to Prevent Heat Shock-Induced Resistance of Target Cells to Ctl," the Journal of Immunology, vol. 164, pp. 2362-2371 (2000).

Adluri, Sucharita et al., "Immunogenicity of synthetic Tf-Klh (keyhole limpet hemocyanin) and sTn-Klh conjugates in colorectal carcinoma patients," Cancer Immunol. Immunother., vol. 41:185-192 (1995).

Altschul, Stephen F. et al., "Gapped Blast and Psi-Blast: a new generation of protein database search programs," Nucleic Acids Research, vol. 25(17):3389-3402 (1997).

Chun, Jongsik et al., "EzTaxon: a web-based tool for the identification of prokaryotes based on 16S ribosomal RNA gene sequences," International Journal of Systemic and Evolutionary Microbiology, vol. 57:2259-2261 (2007).

Clausen, Kenrik et al., "Monoclonal Antibodies Directed to the Blood Group a Associated Structure, Galactosyl-A: Specificity and Relation to the Thomsen-Friedenreich Antigen," Molecular Immunology, vol. 25(2):199-204 (1988).

De Ley, J. et al., "The Quantitative Measurement of DNA Hybridization from Renaturation Rates," Eur. J. Biochem., vol. 12:133-142 (1970).

Giuffre, G. et al., "Detection of Tn, sialosyl-Tn and T antigens in hereditary nonpolyposis colorectal cancer," Virchows Arch, vol. 429:345-352 (1996).

Goletz, S. et al., "Thomsen-Friednenreich Antigen: The 'Hidden' Tumor Antigen," Glycobiology and Medicine, John S. Axford (Ed.), Kluwer Academic/Plenum Publishers, New York, Chapter 10, pp. 147-162 (2003).

Huss, Volker A.R. et al., "Studies on the Spectrophotometric Determination of DNA Hybridization from Renaturation Rates," System Appl. Microbiol., vol. 4:184-192 (1983).

Jeschke, Udo et al., "Binding of galectin-1 (gal-1) to the Thomsen-Friedenreich (TF) antigen on trophoblast cells and inhibition of proliferation of trophoblast tumor cells in vitro by gal-1 or an anti-TF antibody," Histochem Cell Biol, vol. 126:437-444 (2006).

Chassard, Christophe et al., "*Bacteroides xylanisolvens* sp. nov., a xylan-degrading bacterium isolated from human faeces," International Journal of Systematic and Evolutionary Microbiology, vol. 58:1008-1013 (2008).

Gambert, Ulrike et al., "Chemoenzymatic synthesis of the Thonnsen-Friedenreich anitgen determinant," Carbohydrate Research, vol. 299:85-89 (1997).

Goletz, S. et al., "Thomsen-Friedenreich Antigen: The 'Hidden' Tumor Antigen," Glycobiology and Medicine, John S. Axford (Ed.), Kluwer Acacemic/Plenum Publishers, New York, Chapter 10, pp. 147-162 (2003).

Henderson, Gemma et al., "Occurrence of the human tumor-specific antigen structure Galbeta1-3GalNAcalpha-(Thomsen-Freidenreich) and related structures on gut bacteria: Prevalence, immunochemical analysis and structure confirmation," Glycobiology, vol. 21(10):1277-1289 (2011).

Maclean, G.D. et al., "Active Immunization of Human Ovarian Cancer Patients Against a Common Carcinoma (Thomsen-Friedenreich) Determinant Using a Synthetic Carbohydrate Antigen," Journal of Immunotherapy, vol. 11:292-305 (1992).

Slovin, Susan F. et al., "Thomsen-Friedenreich (TF) antigen as a target for prostate cancer vaccine: clinical trial results with TF cluster (c)-KLH plus QS21 conjugate vaccine in patients with biochemically relapsed prostate cancer," Cancer Immunol. Immunother., vol. 54:694-702 (2005).

Ulsemer, Philippe et al., "Preliminary Safety Evaluation of a New Bacteroides xylanisolvens Isolate," Applied and Environmental Microbiology, vol. 78(2):528-535 (2012).

International Preliminary Report on Patentability for Application No. PCT/EP2012/066360, 8 pages, dated Feb. 25, 2014.

International Search Report for Application No. PCT/EP2012/066360, 6 pages, dated Nov. 5, 2012.

Duk, M. et al., "Purification of Human Anti-TF (Thomsen-Friedenreich) and Anti-Tn Antibodies by Affinity Chromatography on Glycophorin a Derivatives and Characterization of the Antibodies by Microtiter Plate Elisa," Archivum Immunologiae etTherapiae Experimentalis, vol. 46, pp. 69-77 (1998).

Elbashir, S. et al., "Duplexes of 21-Nucleotide RNAs Mediate RNA Interference in Cultured Mammalian Cells," Nature, vol. 411, pp. 494-498 (2001).

Euhus, D. et al., "Appraisal of Anti-Idiotypic Antibodies in the Treatment of Solid Tumors in Humans," Surgery, Gynecology & Obstetrics, vol. 175, pp. 89-96 (1992).

European Search Report for Application No. 11 17 6193.8, dated Apr. 16, 2012.

European Search Report for Application No. 11 17 6200.1, dated Apr. 12, 2012.

Feng, H. et al., "Stressed Apoptotic Tumor Cells Express Heat Shock Proteins and Elicit Tumor-Specificity Immunity," Blood, vol. 97, No. 11, pp. 3505-3512 (2001).

Ferencik, M., Handbook of Immunochemistry, First Edition, Chapman & Hall, London, pp. 115-116 (1993).

Fiebig, H. et al., "Clonogenic Assay with Established Human Tumour Xenografts: Correlation of in Vitro to in Vivo Activity as a Basis for Anticancer Drug Discovery," European Journal of Cancer, vol. 40, Issue 6, pp. 802-820 (2004).

Fogolin et al. "Choice of the adequate quantification method for recombinant human GM-CSF produced in different host systems," Electronic J. of Biotech. 5: 243-250 (2002).

Franco, A., "CTL-Based Cancer Preventive/Therapeutic Vaccines for Carcinomas: Role of Tumour-Associated Carbohydrate Antigens," Scandinavian Journal of Immunology, vol. 61, No. 5, pp. 391-397 (2005).

Freshney, R., Culture of Animal Cells: a Manual of Basic Technique and Specialized Applications, Alan R. Liss Inc., New York, p. 4 (1983).

Fujiwara, H. et al., "Establishment of a Tumor-Specific Immunotherapy Model Utilizing TNP-Reactive Helper T Cell Activity and its Application to the Autochthonous Tumor System," The Journal of Immunology, vol. 133, No. 1, pp. 509-514 (1984).

(56) References Cited

OTHER PUBLICATIONS

Fukuda, M. et al. "Structures of novel sialyated O-linked oligosaccharides isolated from human erythrocyte glycophorins," The Journal of Biological Chemistry, 262(25): 11952-11957 (1987).

Gallucci, S. et al., "Danger Signals: SOS to the Immune System," Current Opinion in Immunology, vol. 13, pp. 114-119 (2001).

Gallucci, S. et al., "Natural Adjuvants: Endogenous Activators of Dendritic Cells," Nature Medicine, vol. 5, No. 11, pp. 1249-1255 (1999).

Geneseq, "DHFR—Synuclein Fusion Protein GST-ATSalpha Seq. ID No. 81," (2005) XP002430726.

Giovanella, B. et al., "Effects of Elevated Temperatures and Drugs on the Viability of L1210 Leukemia Cells," Cancer Research, vol. 30, pp. 1623-1631 (1970).

Goletz et al, Advances in Experimental Medicine and Biology, 2003, 535:147-162.

Goletz et al, Glycobiology, Nov. 2011, 21111 :1525 abstract only.

Goletz, Glycobiology, Nov. 2011,21/11 :1524 abstract only.

Goletz, S. et al., "Binding Patterns of 33 TD-4 (MUC1) Antibodies Towards Single-Chain Fragments and Peptides Mimicking the Conformation of the MUC1 PDTRP Epitope," Tumor Biology, vol. 21, Suppl. 1, p. 142 (2000).

Gollasch, H. et al., "Identification of Immunogenic Peptide-Mimics for the Thomsen-Friedenreich-Glycoantigen," Annals of Hematology, vol. 77, No. Supp. 2, p. S84 XP-000960533 (1998).

Gough, M. et al., "Macrophages Orchestrate the Immune Response to Tumor Cell Death," Cancer Research, vol. 61, No. 9, pp. 7240-7247 (2001).

Green, D. et al., "Activation-Induced Cell Death in T Cells," Immunological Reviews, vol. 193, Issue 1, pp. 70-81 (2003).

Gura, T., "Systems for Identifying New Drugs are Often Faulty," Science, vol. 278, pp. 1041-1042 (1997).

Hanisch et al, Histol. Histopathol., 1997, 12:263-281.

Hargrove et al. 1980. Growth Response of Weanling Rats to Heated, Aged, Fractionated, and Chemically Treated Yogurts. Journal of Dairy Science, vol. 63,pp. 1065-1072.

Herrera, A. et al., "Efficiency of Erythropoietin's Signal Peptide for HIV.sub.MN-1 gp 120 Expression," Biochemical and Biophysical Research Communications, vol. 273, Issue 2, pp. 557-559 (2000).

Hinoda, Y. et al., "Circulating Tumor-Associated Antigens Detected by Monoclonal Antibodies Against the Polypeptide Core of Mucin-Comparison of Antigen MUSE11 with CA15-3," Gastroenterologia Japonica, vol. 27, No. 3, pp. 390-395 (1992).

Hinoda, Y. et al., "Primary Structure of the Variable Regions of a Monoclonal Antibody MUSE11 Recognizing the Tandem Repeat Domain of a Mucin Core Protein, MUC1," Journal of Clinical Laboratory Analysis, vol. 7, pp. 100-104 (1993).

Holm, P. et al., "Functional Mapping and Single Chain Construction of the Anti-Cytokeratin 8 Monoclonal Antibody TS1," Molecular Immunology, vol. 44, Issue 6, pp. 1075-1084 (2007).

Hong, Y. et al. "Lec3 Chinese Hamster Ovary Mutants Lack UPD-N-acetylglucosamine 2-EPimerase Activity Because of Mutations in the Epimerase Domain of the Gne Gene," J. Biol. chem 278(52): 53045-53054 (2003).

Hosse, R. et al., "A New Generation of Protein Display Scaffolds for Molecular Recognition," Protein Science, vol. 15, Issue 1, pp. 14-27 (2006).

Hseih, L. et al., "Controlling Chemical Reactivity with Antibodies," Science, vol. 260, pp. 337-339 (1993).

Huang, Q. et al., "Heat-Induced Gene Expression as a Novel Targeted Cancer Gene Therapy Strategy," Cancer Research, vol. 60, pp. 3435-3439 (2000).

Hufton, S. et al., "Development and Application of Cytotoxic T Lymphocyte-Associated Antigen 4 as a Protein Scaffold for the Generation of Novel Binding Ligands," FEBS Letters, vol. 475, Issue 3, pp. 225-231 (2000).

Ichiyama, "Induction of Non-HLA Restricted Anti-Tumor Effector Cells with Strong Cytoxic Activity Using MUC1/B7 Cotransfected K562 Cells," Cell Resource Center for Biomedical Research, Institute of Development, Aging, and Cancer, Tohoku University,Sendai, Japan, vol. 51, No. 3-4, pp. 93-110, XP-001182213 (2000).

International Search Report for International Application No. PCT/EP2009/003401, dated Sep. 10, 2009.

International Search Report for PCT Application No. PCT/EP2003/009140 (WO2004/018659) dated Feb. 9, 2004, 8 pages.

International Search Report for PCT Application No. PCT/EP2004/009281 (WO2005/017130) dated Apr. 14, 2005, 6 pages.

International Search Report for PCT Application No. PCT/EP2005/01593 (WO 2005/080585) dated Jul. 15, 2005.

International Search Report for PCT Application No. PCT/EP2007/007877 (WO 2008/028686 A3) dated Apr. 18, 2008.

International Search Report for PCT Application No. PCT/EP2007/009765 (WO 2008/055702 Al) dated Apr. 15, 2008.

International Search Report for PCT Application No. PCT/EP2007/009766 (WO 2008/055703 A2) dated Oct. 7, 2008.

International Search Report for PCT/DE20031003994 (WO2004/050707) dated Aug. 10, 2004, 8 pages.

Irazoqui et al, Current Cancer Drug Targets, 2003, 3:433-443.

Irazoqui et al, Immunology and Cell Biology, 2005, 83:405-412.

Isner, J. et al., "Clinical Evidence of Angiogenesis After Arterial Gene Transfer of phVEGF.sub.165 in Patient with Ischaemic Limb," The Lancet, vol. 348, pp. 370-374 (1996).

Jacobs, C. et al. "Substrate specificity of the sialic acid biosynthetic pathway," Biochemistry 40(43): 12864-12874 (2001).

U.S. Appl. No. 12/514,248, filed Apr. 20, 2016, N. Minnifield.

Goletz, S., "Turning Glycomics into Health," Glycotope, The GlycoEngineering Company, Bio 2006 Annual Convention in Chicago, Presentation Slides, 12 pages (2006).

Saitou, Naruya et al., "The Neighbor-joining Method: A New Method for Reconstructing Phylogenetic Trees," Mol. Biol. Evol., vol. 4(4):406-425 (1987).

Shigeoka, Hironori et al., "Inhibition of Liver Metastases from Neuraminidase-Treated Colon 26 Cells by an Anti-Thomsen-Friedenreich-Specific Monoclonal Antibody," Tumor Biol., vol. 20:139-146 (1999).

Springer, Georg F. et al., "Origin of Anti-Thomsen-Friedenreich (T) and Tn Agglutinins in Man and in White Leghorn Chicks," British Journal of Haematology, vol. 47:453-460 (1981).

Springer, G.F. et al., "Precursors of the Blood Group MN Antigens as Human Carcinoma-Associated Antigens," Transfusion, vol. 19(3)233-249 (1979).

Stackebrandt, E. et al., "Taxonomic Note: A Place for DNA—DNA Reassociation and 16S rRNA Sequence Analysis in the Present Species Definition in Bacteriology," International Journal of Systematic Bacteriology, vol. 44(4):846-849 (1994).

Stackebrandt, Erko et al., "Taxonomic parameters revisited: tarnished gold standards," Microbiology Today, vol. 33:152-155 (2006).

Tamura, Koichiro et al., "MEGA4: Molecular Evolutionary Genetics Analysis (MEGA) Software Version 4.0," Mol. Biol. Evol., vol. 24(8):1596-1599 (2007).

Zhang, Zheng et al., "A Greedy Algorithm for Aligning DNA Sequences," Journal of Computational Biology, vol. 7 (1/2):203-214 (2000).

\* cited by examiner

Structure #1

Structure #2

Structure #3

Structure #4

Structure #5

A

B

C

D

SEQUENCE LISTING

```
<160> NUMBER OF SEQ ID NOS: 21

<210> SEQ ID NO 1
<211> LENGTH: 5
<212> TYPE: PRT
<213> ORGANISM: Artificial
<220> FEATURE:
<223> OTHER INFORMATION: CDR H1

<400> SEQUENCE: 1

Asn Tyr Trp Leu Gly
1               5

<210> SEQ ID NO 2
<211> LENGTH: 17
<212> TYPE: PRT
<213> ORGANISM: Artificial
<220> FEATURE:
<223> OTHER INFORMATION: CDR H2
```

-continued

```
<400> SEQUENCE: 2

Asp Ile Tyr Pro Gly Gly Gly Tyr Thr Asn Tyr Asn Glu Lys Phe Lys
1               5                   10                  15

Gly

<210> SEQ ID NO 3
<211> LENGTH: 10
<212> TYPE: PRT
<213> ORGANISM: Artificial
<220> FEATURE:
<223> OTHER INFORMATION: CDR H3

<400> SEQUENCE: 3

Tyr Asp Ala Ala Gly Pro Trp Phe Ala Tyr
1               5                   10

<210> SEQ ID NO 4
<211> LENGTH: 16
<212> TYPE: PRT
<213> ORGANISM: Artificial
<220> FEATURE:
<223> OTHER INFORMATION: CDR L1

<400> SEQUENCE: 4

Arg Ser Ser Gln Ser Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Artificial
<220> FEATURE:
<223> OTHER INFORMATION: CDR L2

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial
<220> FEATURE:
<223> OTHER INFORMATION: CDR L3

<400> SEQUENCE: 6

Phe Gln Gly Ser His Val Pro Tyr Thr
1               5

<210> SEQ ID NO 7
<211> LENGTH: 5
<212> TYPE: PRT
<213> ORGANISM: Artificial
<220> FEATURE:
<223> OTHER INFORMATION: CDR H1

<400> SEQUENCE: 7

Asn Tyr Trp Leu Gly
1               5

<210> SEQ ID NO 8
<211> LENGTH: 17
<212> TYPE: PRT
<213> ORGANISM: Artificial
<220> FEATURE:
<223> OTHER INFORMATION: CDR H2
```

<400> SEQUENCE: 8

Asp Ile Tyr Pro Gly Gly Ser Tyr Thr Asn Tyr Asn Glu Lys Phe Lys
1               5                   10                  15

Gly

<210> SEQ ID NO 9
<211> LENGTH: 8
<212> TYPE: PRT
<213> ORGANISM: Artificial
<220> FEATURE:
<223> OTHER INFORMATION: CDR H3

<400> SEQUENCE: 9

Tyr Asp Asn His Tyr Phe Asp Tyr
1               5

<210> SEQ ID NO 10
<211> LENGTH: 16
<212> TYPE: PRT
<213> ORGANISM: Artificial
<220> FEATURE:
<223> OTHER INFORMATION: CDR L1

<400> SEQUENCE: 10

Arg Ser Ser Gln Ser Leu Leu His Ser Asn Gly Asn Thr Tyr Leu His
1               5                   10                  15

<210> SEQ ID NO 11
<211> LENGTH: 7
<212> TYPE: PRT
<213> ORGANISM: Artificial
<220> FEATURE:
<223> OTHER INFORMATION: CDR L2

<400> SEQUENCE: 11

Lys Val Ser Asn Arg Phe Ser
1               5

<210> SEQ ID NO 12
<211> LENGTH: 9
<212> TYPE: PRT
<213> ORGANISM: Artificial
<220> FEATURE:
<223> OTHER INFORMATION: CDR L3

<400> SEQUENCE: 12

Ser Gln Ser Thr His Val Pro Tyr Thr
1               5

<210> SEQ ID NO 13
<211> LENGTH: 573
<212> TYPE: PRT
<213> ORGANISM: Artificial
<220> FEATURE:
<223> OTHER INFORMATION: heavy chain mIgM

<400> SEQUENCE: 13

Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

```
Gly Asp Ile Tyr Pro Gly Gly Gly Tyr Thr Asn Tyr Asn Glu Lys Phe
         50                  55                  60

Lys Gly Lys Ala Thr Leu Thr Ala Asp Thr Ser Ser Thr Ala Tyr
 65              70                  75                  80

Met Gln Leu Ser Ser Leu Thr Ser Glu Asp Ser Ala Val Tyr Phe Cys
                 85                  90                  95

Ala Tyr Asp Ala Ala Gly Pro Trp Phe Ala Tyr Trp Gly Gln Gly
            100                 105                 110

Thr Thr Val Thr Val Ser Glu Ser Gln Ser Phe Pro Asn Val Phe Pro
            115                 120                 125

Leu Val Ser Cys Glu Ser Pro Leu Ser Asp Lys Asn Leu Val Ala Met
        130                 135                 140

Gly Cys Leu Ala Arg Asp Phe Leu Pro Ser Thr Ile Ser Phe Thr Trp
145                 150                 155                 160

Asn Tyr Gln Asn Asn Thr Glu Val Ile Gln Gly Ile Arg Thr Phe Pro
                165                 170                 175

Thr Leu Arg Thr Gly Gly Lys Tyr Leu Ala Thr Ser Gln Val Leu Leu
            180                 185                 190

Ser Pro Lys Ser Ile Leu Glu Gly Ser Asp Glu Tyr Leu Val Cys Lys
        195                 200                 205

Ile His Tyr Gly Gly Lys Asn Arg Asp Leu His Val Pro Ile Pro Ala
210                 215                 220

Val Ala Glu Met Asn Pro Asn Val Asn Val Phe Val Pro Pro Arg Asp
225                 230                 235                 240

Gly Phe Ser Gly Pro Ala Pro Arg Lys Ser Lys Leu Ile Cys Glu Ala
                245                 250                 255

Thr Asn Phe Thr Pro Lys Pro Ile Thr Val Ser Trp Leu Lys Asp Gly
                260                 265                 270

Lys Leu Val Glu Ser Gly Phe Thr Thr Asp Pro Val Thr Ile Glu Asn
            275                 280                 285

Lys Gly Ser Thr Pro Gln Thr Tyr Lys Val Ile Ser Thr Leu Thr Ile
            290                 295                 300

Ser Glu Ile Asp Trp Leu Asn Leu Asn Val Tyr Thr Cys Arg Val Asp
305                 310                 315                 320

His Arg Gly Leu Thr Phe Leu Lys Asn Val Ser Ser Thr Cys Ala Ala
                325                 330                 335

Ser Pro Ser Thr Asp Ile Leu Thr Phe Thr Ile Pro Pro Ser Phe Ala
            340                 345                 350

Asp Ile Phe Leu Ser Lys Ser Ala Asn Leu Thr Cys Leu Val Ser Asn
            355                 360                 365

Leu Ala Thr Tyr Glu Thr Leu Asn Ile Ser Trp Ala Ser Gln Ser Gly
370                 375                 380

Glu Pro Leu Glu Thr Lys Ile Lys Ile Met Glu Ser His Pro Asn Gly
385                 390                 395                 400

Thr Phe Ser Ala Lys Gly Val Ala Ser Val Cys Val Glu Asp Trp Asn
                405                 410                 415

Asn Arg Lys Glu Phe Val Cys Thr Val Thr His Arg Asp Leu Pro Ser
            420                 425                 430

Pro Gln Lys Lys Phe Ile Ser Lys Pro Asn Glu Val His Lys His Pro
            435                 440                 445

Pro Ala Val Tyr Leu Leu Pro Pro Ala Arg Glu Gln Leu Asn Leu Arg
450                 455                 460

Glu Ser Ala Thr Val Thr Cys Leu Val Lys Gly Phe Ser Pro Ala Asp
```

```
            465                 470                 475                 480
    Ile Ser Val Gln Trp Leu Gln Arg Gly Gln Leu Leu Pro Gln Glu Lys
                        485                 490                 495

Tyr Val Thr Ser Ala Pro Met Pro Glu Pro Gly Ala Pro Gly Phe Tyr
                        500                 505                 510

Phe Thr His Ser Ile Leu Thr Val Thr Glu Glu Trp Asn Ser Gly
                        515                 520                 525

Glu Thr Tyr Thr Cys Val Val Gly His Glu Ala Leu Pro His Leu Val
                        530                 535                 540

Thr Glu Arg Thr Val Asp Lys Ser Thr Gly Lys Pro Thr Leu Tyr Asn
    545                 550                 555                 560

Val Ser Leu Ile Met Ser Asp Thr Gly Gly Thr Cys Tyr
                        565                 570

<210> SEQ ID NO 14
<211> LENGTH: 448
<212> TYPE: PRT
<213> ORGANISM: Artificial
<220> FEATURE:
<223> OTHER INFORMATION: heavy chain cIgG

<400> SEQUENCE: 14

Gln Val Gln Leu Lys Glu Ser Gly Ala Glu Leu Val Arg Pro Gly Thr
    1               5                   10                  15

Ser Val Lys Ile Ser Cys Lys Ala Ser Gly Tyr Thr Phe Thr Asn Tyr
                        20                  25                  30

Trp Leu Gly Trp Val Lys Gln Arg Pro Gly His Gly Leu Glu Trp Ile
                        35                  40                  45

Gly Asp Ile Tyr Pro Gly Gly Gly Tyr Thr Asn Tyr Asn Glu Lys Phe
                        50                  55                  60

Lys Gly Lys Ala Thr Leu Thr Ala Asp Thr Ser Ser Ser Thr Ala Tyr
    65                  70                  75                  80

Met Gln Leu Ser Ser Leu Thr Ser Glu Asp Ser Ala Val Tyr Phe Cys
                        85                  90                  95

Ala Tyr Tyr Asp Ala Ala Gly Pro Trp Phe Ala Tyr Trp Gly Gln Gly
                        100                 105                 110

Thr Thr Val Thr Val Ser Gly Ser Thr Lys Gly Pro Ser Val Phe Pro
                        115                 120                 125

Leu Ala Pro Ser Ser Lys Ser Thr Ser Gly Gly Thr Ala Ala Leu Gly
                        130                 135                 140

Cys Leu Val Lys Asp Tyr Phe Pro Glu Pro Val Thr Val Ser Trp Asn
    145                 150                 155                 160

Ser Gly Ala Leu Thr Ser Gly Val His Thr Phe Pro Ala Val Leu Gln
                        165                 170                 175

Ser Ser Gly Leu Tyr Ser Leu Ser Ser Val Val Thr Val Pro Ser Ser
                        180                 185                 190

Ser Leu Gly Thr Gln Thr Tyr Ile Cys Asn Val Asn His Lys Pro Ser
                        195                 200                 205

Asn Thr Lys Val Asp Lys Lys Val Glu Pro Lys Ser Cys Asp Lys Thr
                        210                 215                 220

His Thr Cys Pro Pro Cys Pro Ala Pro Glu Leu Leu Gly Gly Pro Ser
    225                 230                 235                 240

Val Phe Leu Phe Pro Pro Lys Pro Lys Asp Thr Leu Met Ile Ser Arg
                        245                 250                 255

Thr Pro Glu Val Thr Cys Val Val Val Asp Val Ser His Glu Asp Pro
```

```
                260                 265                 270
Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 15
<211> LENGTH: 571
<212> TYPE: PRT
<213> ORGANISM: Artificial
<220> FEATURE:
<223> OTHER INFORMATION: heavy chain cIgM

<400> SEQUENCE: 15

Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
            100                 105                 110

Thr Thr Val Thr Val Ser Gly Ser Ala Ser Ala Pro Thr Leu Phe Pro
        115                 120                 125

Leu Val Ser Cys Glu Asn Ser Pro Ser Asp Thr Ser Ser Val Ala Val
    130                 135                 140

Gly Cys Leu Ala Gln Asp Phe Leu Pro Asp Ser Ile Thr Leu Ser Trp
145                 150                 155                 160

Lys Tyr Lys Asn Asn Ser Asp Ile Ser Ser Thr Arg Gly Phe Pro Ser
                165                 170                 175

Val Leu Arg Gly Gly Lys Tyr Ala Ala Thr Ser Gln Val Leu Leu Pro
```

```
                    180                 185                 190
Ser Lys Asp Val Met Gln Gly Thr Asp Glu His Val Val Cys Lys Val
                195                 200                 205

Gln His Pro Asn Gly Asn Lys Glu Lys Asn Val Pro Leu Pro Val Ile
210                 215                 220

Ala Glu Leu Pro Pro Lys Val Ser Val Phe Pro Pro Arg Asp Gly
225                 230                 235                 240

Phe Phe Gly Asn Pro Arg Lys Ser Lys Leu Ile Cys Gln Ala Thr Gly
                245                 250                 255

Phe Ser Pro Arg Gln Ile Gln Val Ser Trp Leu Arg Glu Gly Lys Gln
                260                 265                 270

Val Gly Ser Gly Val Thr Thr Asp Gln Val Gln Ala Glu Ala Lys Glu
                275                 280                 285

Ser Gly Pro Thr Thr Tyr Lys Val Thr Ser Thr Leu Thr Ile Lys Glu
                290                 295                 300

Ser Asp Trp Leu Gly Gln Ser Met Phe Thr Cys Arg Val Asp His Arg
305                 310                 315                 320

Gly Leu Thr Phe Gln Gln Asn Ala Ser Ser Met Cys Val Pro Asp Gln
                325                 330                 335

Asp Thr Ala Ile Arg Val Phe Ala Ile Pro Pro Ser Phe Ala Ser Ile
                340                 345                 350

Phe Leu Thr Lys Ser Thr Lys Leu Thr Cys Leu Val Thr Asp Leu Thr
                355                 360                 365

Thr Tyr Asp Ser Val Thr Ile Ser Trp Thr Arg Gln Asn Gly Glu Ala
                370                 375                 380

Val Lys Thr His Thr Asn Ile Ser Glu Ser His Pro Asn Ala Thr Phe
385                 390                 395                 400

Ser Ala Val Gly Glu Ala Ser Ile Cys Glu Asp Asp Trp Asn Ser Gly
                405                 410                 415

Glu Arg Phe Thr Cys Thr Val Thr His Thr Asp Leu Pro Ser Pro Leu
                420                 425                 430

Lys Gln Thr Ile Ser Arg Pro Lys Gly Val Ala Leu His Arg Pro Asp
                435                 440                 445

Val Tyr Leu Leu Pro Pro Ala Arg Glu Gln Leu Asn Leu Arg Glu Ser
                450                 455                 460

Ala Thr Ile Thr Cys Leu Val Thr Gly Phe Ser Pro Ala Asp Val Phe
465                 470                 475                 480

Val Gln Trp Met Gln Arg Gly Gln Pro Leu Ser Pro Glu Lys Tyr Val
                485                 490                 495

Thr Ser Ala Pro Met Pro Glu Pro Gln Ala Pro Gly Arg Tyr Phe Ala
                500                 505                 510

His Ser Ile Leu Thr Val Ser Glu Glu Trp Asn Thr Gly Glu Thr
                515                 520                 525

Tyr Thr Cys Val Val Ala His Glu Ala Leu Pro Asn Arg Val Thr Glu
                530                 535                 540

Arg Thr Val Asp Lys Ser Thr Gly Lys Pro Thr Leu Tyr Asn Val Ser
545                 550                 555                 560

Leu Val Met Ser Asp Thr Ala Gly Thr Cys Tyr
                565                 570

<210> SEQ ID NO 16
<211> LENGTH: 219
<212> TYPE: PRT
<213> ORGANISM: Artificial
```

<220> FEATURE:
<223> OTHER INFORMATION: light chain mIgM

<400> SEQUENCE: 16

Asp Ile Gln Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 17
<211> LENGTH: 219
<212> TYPE: PRT
<213> ORGANISM: Artificial
<220> FEATURE:
<223> OTHER INFORMATION: light chain cIgG/M

<400> SEQUENCE: 17

Asp Ile Gln Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu

|     | 115 |     |     |     | 120 |     |     |     | 125 |     |     |
|-----|-----|-----|-----|-----|-----|-----|-----|-----|-----|-----|-----|

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 18
<211> LENGTH: 571
<212> TYPE: PRT
<213> ORGANISM: Artificial
<220> FEATURE:
<223> OTHER INFORMATION: heavy chain mIgM

<400> SEQUENCE: 18

Gln Val Gln Leu Lys Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Ser Tyr Thr Asn Tyr Asn Glu Lys Phe
        50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Asp Asn His Tyr Phe Asp Tyr Trp Gly Gln Gly Thr Thr
            100                 105                 110

Leu Thr Val Ser Glu Ser Gln Ser Phe Pro Asn Val Phe Pro Leu Val
        115                 120                 125

Ser Cys Glu Ser Pro Leu Ser Asp Lys Asn Leu Val Ala Met Gly Cys
    130                 135                 140

Leu Ala Arg Asp Phe Leu Pro Ser Thr Ile Ser Phe Thr Trp Asn Tyr
145                 150                 155                 160

Gln Asn Asn Thr Glu Val Ile Gln Gly Ile Arg Thr Phe Pro Thr Leu
                165                 170                 175

Arg Thr Gly Gly Lys Tyr Leu Ala Thr Ser Gln Val Leu Leu Ser Pro
            180                 185                 190

Lys Ser Ile Leu Glu Gly Ser Asp Glu Tyr Leu Val Cys Lys Ile His
        195                 200                 205

Tyr Gly Gly Lys Asn Arg Asp Leu His Val Pro Ile Pro Ala Val Ala
    210                 215                 220

Glu Met Asn Pro Asn Val Asn Val Phe Val Pro Arg Asp Gly Phe
225                 230                 235                 240

Ser Gly Pro Ala Pro Arg Lys Ser Lys Leu Ile Cys Glu Ala Thr Asn
                245                 250                 255

Phe Thr Pro Lys Pro Ile Thr Val Ser Trp Leu Lys Asp Gly Lys Leu

```
            260                 265                 270
Val Glu Ser Gly Phe Thr Thr Asp Pro Val Thr Ile Glu Asn Lys Gly
            275                 280                 285

Ser Thr Pro Gln Thr Tyr Lys Val Ile Ser Thr Leu Thr Ile Ser Glu
            290                 295                 300

Ile Asp Trp Leu Asn Leu Asn Val Tyr Thr Cys Arg Val Asp His Arg
305                 310                 315                 320

Gly Leu Thr Phe Leu Lys Asn Val Ser Ser Thr Cys Ala Ala Ser Pro
            325                 330                 335

Ser Thr Asp Ile Leu Thr Phe Thr Ile Pro Pro Ser Phe Ala Asp Ile
            340                 345                 350

Phe Leu Ser Lys Ser Ala Asn Leu Thr Cys Leu Val Ser Asn Leu Ala
            355                 360                 365

Thr Tyr Glu Thr Leu Asn Ile Ser Trp Ala Ser Gln Ser Gly Glu Pro
            370                 375                 380

Leu Glu Thr Lys Ile Lys Ile Met Glu Ser His Pro Asn Gly Thr Phe
385                 390                 395                 400

Ser Ala Lys Gly Val Ala Ser Val Cys Val Glu Asp Trp Asn Asn Arg
            405                 410                 415

Lys Glu Phe Val Cys Thr Val Thr His Arg Asp Leu Pro Ser Pro Gln
            420                 425                 430

Lys Lys Phe Ile Ser Lys Pro Asn Glu Val His Lys His Pro Pro Ala
            435                 440                 445

Val Tyr Leu Leu Pro Pro Ala Arg Glu Gln Leu Asn Leu Arg Glu Ser
            450                 455                 460

Ala Thr Val Thr Cys Leu Val Lys Gly Phe Ser Pro Ala Asp Ile Ser
465                 470                 475                 480

Val Gln Trp Leu Gln Arg Gly Gln Leu Leu Pro Gln Glu Lys Tyr Val
            485                 490                 495

Thr Ser Ala Pro Met Pro Glu Pro Gly Ala Pro Gly Phe Tyr Phe Thr
            500                 505                 510

His Ser Ile Leu Thr Val Thr Glu Glu Glu Trp Asn Ser Gly Glu Thr
            515                 520                 525

Tyr Thr Cys Val Val Gly His Glu Ala Leu Pro His Leu Val Thr Glu
            530                 535                 540

Arg Thr Val Asp Lys Ser Thr Gly Lys Pro Thr Leu Tyr Asn Val Ser
545                 550                 555                 560

Leu Ile Met Ser Asp Thr Gly Gly Thr Cys Tyr
            565                 570

<210> SEQ ID NO 19
<211> LENGTH: 219
<212> TYPE: PRT
<213> ORGANISM: Artificial
<220> FEATURE:
<223> OTHER INFORMATION: light chain mIgM

<400> SEQUENCE: 19

Asp Ile Val Ile Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
```

```
            50                  55                  60
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 20
<211> LENGTH: 20
<212> TYPE: DNA
<213> ORGANISM: Artificial
<220> FEATURE:
<223> OTHER INFORMATION: 16S rRNA primer

<400> SEQUENCE: 20
agagtttgat cmtggctcag                                                     20

<210> SEQ ID NO 21
<211> LENGTH: 18
<212> TYPE: DNA
<213> ORGANISM: Artificial
<220> FEATURE:
<223> OTHER INFORMATION: 16S rRNA primer

<400> SEQUENCE: 21
gwattaccgc ggckgctg                                                       18
```

MICROORGANISMS CARRYING A TUMOR ANTIGEN

RELATED APPLICATIONS

This application is a 35 U.S.C. 371 national stage filing of International Application No. PCT/EP2012/066360, filed on Aug. 22, 2012, which claims priority to European Patent Application No. 11178322.1, filed on Aug. 22, 2011 and U.S. Application No. 61/526,054, filed Aug. 22, 2011. The contents of the aforementioned applications are hereby incorporated by reference.

FIELD OF THE INVENTION

The present invention relates to antigen-presenting microorganisms. In particular, microorganisms of the species *Bacteroides xylanisolvens* carrying the core-1 antigen on their surface are provided. Furthermore, the present invention provides the use of these microorganisms in medicine as well as products containing said microorganisms.

BACKGROUND OF THE INVENTION

Aberrant glycosylation is a typical hallmark of cancer cells. Carbohydrate tumor antigens on glycoproteins and glycolipids are therefore targets for active and passive immunotherapy. These highly abundant antigens are de novo expressed or upregulated due to changes in the complex glycosylation apparatus of tumor cells. Various lipid or protein bound carbohydrate tumor antigens are described, e.g. GM2, GD2, GD3, fucosylated GM1, Globo H, Le$^y$ and the mucin core structures Tn, Sialyl-Tn and the Thomson Friedenreich antigen.

Thomsen-Friedenreich antigen (TF) is a known carbohydrate structure described as a tumor antigen in a series of reports. TF exists in two forms, TF alpha and TF beta, which can be linked to proteins or glycolipids.

Core-1 is the disaccharide Gal-β1,3-GalNAc which is in particular O-glycosidically linked in an alpha-anomeric configuration to the hydroxy amino acids serine or threonine of proteins in carcinoma cells. Core-1 corresponds to the TF-alpha structure of Thomsen-Friedenreich and is linked only to proteins on tumors. Hence, the terms core-1 and Thomsen-Friedenreich do not necessarily refer to identical structures.

Core-1 is masked by other carbohydrate components in healthy and benign-diseased tissue but is uncovered in a majority of carcinomas and in some non-epithelial malignancies. Therefore, core-1 is a specific pan-carcinoma antigen.

Core-1 is an important tumor antigen. Core-1 is expressed on over 60% of primary colon carcinomas and over 90% of liver metastases from colon cancer as well as on the majority of the carcinomas of other major indications including breast, lung, ovarian, prostate, and other gastrointestinal cancers such as gastric, and pancreatic carcinomas. Core-1 is an independent prognostic marker for patients with colon carcinomas, the mortality rate increases and the medium survival decreases in accordance with the increasing intensity of core-1 expression. The development of liver metastases correlates with the expression of core-1. Patients with core-1 positive primary carcinomas develop liver metastases in nearly 60% of the cases, while the risk for liver metastasis with core-1-negative tumors is significantly lower (less than 20%). Besides mediating metastasis into the liver core-1 may also play a role in the metastasis via the endothelium.

The exceptionally high pan-carcinomic specificity, prognostic relevance and direct involvement in liver metastasis render Thomsen-Friedenreich and particularly core-1 a prime target for cancer immunotherapy.

As a result of the wide distribution of the core-1, it is advantageous to provide a core-1 positive microorganism having a cell surface structure corresponding to core-1 which can be used as pharmaceutical, for example, in the prevention and treatment of cancer, in particular for vaccination.

There were attempts to provide a therapy approach based on Thomsen-Friedenreich. E.g. Shigoeka et al. (1999) describe the inhibition of liver metastasis from neuramidase treated Colon 26 cells by an anti-Thomsen-Friedenreich specific monoclonal antibody in a mouse model. However, due to the difficulties in generating highly specific anti-TF antibodies and because of their nature as IgM isotypes with comparably lower intrinsic affinities of single binding domains, TF-specific antibodies were not further developed so far. Further, some anti-TF-antigen antibodies are not clinically useful because they cause undesirable proliferation of tumor cells. Also WO 2006/012626 describes the therapeutic use of anti-TF antigen antibodies. Binding of TF-specific antibodies has been shown to inhibit the proliferation of tumor cells (Jeschke et. al. (2006)).

Furthermore, there were also attempts to develop vaccines based on Thomsen-Friedenreich. Most of them focused on the induction of antibody responses. E.g. Livingston and Lloyd (2000) used non-natural TF-conjugates, wherein synthetic TF was randomly coupled to KLH. This conjugates raised a humoral immune response against synthetic TF but not against TF on natural ligands (Adluri et al. (1995)). They were thus not TF specific as they would not recognize TF on a tumor structure.

Springer and Desai used vaccination with a T/Tn vaccine composed of types 0 and MN red blood cell derived glycoproteins which resulted in improved breast cancer patient survival, although only small amounts of IgM were made. However, IgM represents a less mature immune response and many previous studies relating to antibodies to TF-Ag involve IgM antibodies, therefore more pronounced highly TF specific immune responses would be needed and preferably an IgG response.

Few reports are known which describe microorganisms supposedly positive for TF. E.g. Springer et al. (Brit J Haematol 47 (1981), 453-460; Transfusion 19 (1979), 233-249) report on an aerobic microorganism (*E. coli* 086) which can generate a polyclonal antibody response in chickens and humans which might also recognize TF on human erythrocytes. Springer used adsorption of anti-T and hemagglutination assays with sialidase-treated T erythrocytes in order to determine roughly the specificity of the immune response. However, sialidase-treatment of human erythrocytes results in demasking of several carbohydrate epitopes, among them but not exclusively TF and in particular core-1. Therefore, the reaction tested by Springer does not show a specificity for TF and in particular core-1 due to cross-reactivities. A respective non-specific microorganism has only a limited suitability as a vaccine due to its unspecificity as it would not raise a strong immune response which is specifically directed against TF but against similar TF-like structures and hence potentially also increasingly against non-tumor tissues or cells of the body. Furthermore, tests have shown that *E. coli* 086 is not positive for core-1 expression because it is not bound by core-1 specific antibodies.

WO 2008/055703 discloses core-1 positive microorganisms, in particular, microorganisms of the species *Bacte-*

*roides ovatus* expressing a core-1 antigen on their cell surface such as AG6 and MU1 and their use as pharmaceuticals. Expression of a core-1 antigen was confirmed by binding of core-1 specific antibodies to said microorganisms. Furthermore, WO 2008/055703 discloses the use of respective microorganisms in therapy.

When using core-1 positive microorganisms as pharmaceuticals it is desirous that the core-1 positive microorganism not only expresses a core-1 antigen, but that the microorganism shows a high core-1 antigen expression in order to effectively stimulate a core-1 specific immune response. Furthermore, it is desirous that the core-1 positive microorganism that is chosen for use as pharmaceutical has a stable, and preferably homogeneous high core-1 antigen expression. A stable, high core-1 antigen expression ensures that the product containing the core-1 positive microorganism exhibits less variability what is important for the product quality, in particular in the pharmaceutical field. A stable, high core-1 antigen expression is also important in order to fulfill the regulatory requirements.

Therefore, it is the object of the present invention to provide alternative core-1 positive microorganisms, in particular microorganisms having a stable, high core-1 antigen expression on their cell surface.

SUMMARY OF THE INVENTION

The present inventors have found core-1 positive microorganisms of the species *Bacteroides xylanisolvens*. A microorganism is core-1 positive and accordingly, expresses a core-1 antigen on its surface, if a core-1 specific antibody upon contact specifically binds said microorganism.

*Bacteroides xylanisolvens* is a novel species of the genus *Bacteroides*, which was described for the first time by Chassard et al ("*Bacteroides xylanisolvens* sp. Nov., a xylan-degrading bacterium isolated from human faeces"; International Journal of Systematic and Evolutionary Microbiology (2008); 58, 1008-1013). It is a xylan-degrading bacterium which can be isolated from human feces and thus, is a human commensal microorganism. It is a Gram-negative *bacillus* bacterium which in general has a low pathogenicity. *Bacteroides xylanisolvens* was deposited as DSM 18836 at the Deutsche Sammlung von Mikroorganismen and Zellkulturen (DSMZ), Inhoffenstraβe 7B, 38124 Braunschweig (DE) and is publicly available therefrom. *Bacteroides xylanisolvens* (DSM 18836) does not express a core-1 antigen, as was shown by experiments with core-1 specific antibodies. Said core-1 specific antibodies did not recognize and thus did not bind *Bacteroides xylanisolvens* (DSM 18836) which proves that it does not express a core-1 antigen and hence, is not core-1 positive. Therefore, it was very surprising for the inventors that they were able to identify core-1 positive microorganisms of the species *Bacteroides xylanisolvens*. Furthermore, the inventors have found that core-1 positive microorganisms of the species *Bacteroides xylanisolvens* show an advantageous core-1 antigen expression profile, because the core-1 antigen is expressed not only in high amounts, but the expression is also very stable and furthermore, homogenous. As discussed in the introduction, a stable, high core-1 antigen expression is an important advantage, in particular when using a core-1 positive microorganism in the field of pharmaceuticals. For example, products manufactured with microorganisms having a stable and homogeneous, high core-1 expression have a constant, high core-1 content. Therefore, less microorganisms are needed for producing a product with the desired core-1 level and these microorganisms provide for a constant product quality and less deficient products. Therefore, due to the special characteristics with respect to the core-1 antigen expression, the core-1 positive microorganism of the present invention is especially suitable for use in the pharmaceutical field. The same applies to core-1 positive lysates and/or fractions of said microorganism.

Therefore, the core-1 positive microorganisms of the present invention or core-1 positive lysates or fractions thereof can be used, for example, in the prophylaxis and treatment of diseases associated with a core-1 expression, in particular cancer wherein the cancer cells such as e.g. tumor cells express core-1. When administered to a patient, the core-1 positive microorganisms of the present invention or the core-1 positive lysates or fractions thereof are capable of stimulating an immune response against core-1 which then also turns against the core-1 positive cells of the disease. Due to the high, stable core-1 antigen expression profile, the induced and/or enhanced immune response is very strong. The stable, high core-1 antigen expression of the microorganisms according to the invention furthermore provides for a constant core-1 activity/expression without significant batch-to-batch variations when using the same amount of core-1 positive microorganisms according to the present invention or core-1 positive lysates or fractions thereof. This also improves the quality of the final products, respectively leads to less deficient products, because the microorganisms of the present invention have a stable, high core-1 antigen expression and accordingly, provide a rather constant amount of the core-1 antigen. The high, homogenous amount of core-1 antigen that is provided by the microorganism according to the present invention also allows to reduce the amount of microorganisms necessary for eliciting an immune response.

Furthermore, the microorganisms according to the present invention have no pathogenicity and thus, can be administered without a high risk of causing adverse side effects, in particular when administered to human beings. Additionally, due to the low pathogenicity, there are no serious restrictions for the manufacture, distribution and marketing of the microorganisms according to the present invention by the statutory regulations, which thus can be fulfilled with little effort. In particular, *Bacteroides xylanisolvens* microorganisms are classified as biological agent of risk group 1 according to the European Directive 2000/54/EC and the German "Biostoffverordnung". Risk group 1 is the lowest of four risk groups and concerns biological agents that are unlikely to cause human disease. Many other microorganisms, also including microorganisms of other *Bacteroides* species are classified in higher risk groups (e.g. *Bacteroides ovatus* is a biological agent of risk group 2). Additionally, as demonstrated in the examples the microorganisms according to the present invention in particular are negative for plasmid DNA material, the most important virulence factors and most of the relevant extracellular enzymes and pathogenic factors, and do not attach to epithelial cells of the human colon. Furthermore, the microorganisms according to the present invention showed no adverse effects in toxicological studies in mice and no adverse effect of any nature in human taking daily doses of up to $8.5*10^{11}$ CTC1 over three weeks. Thus, the microorganisms according to the present invention fulfill a very high safety standard and may be consumed by humans without a risk of unwanted side effects. Furthermore, the microorganisms according to the present invention preferably is sensitive to various antibiotics and thus, may be easily and effectively be eliminated, if necessary.

Additionally, the stable and homogeneous core-1 expression of the microorganisms according to the invention can be used as marker for the product quality. Since natural microorganisms, in particular microorganisms which are undesired in final products, generally do not express core-1, the core-1 content can be used as specific marker for the desired microorganisms according to the present invention. In particular, the core-1 content can be used as marker for the homogeneity of cultures of microorganisms containing the microorganism according to the present invention, and/or can be used as marker for the amount of microorganisms according to the present invention in a culture. Moreover, compared to other core-1 positive microorganisms, the production of the microorganisms according to the present invention having a stable and homogeneous, high core-1 expression is improved since sufficient amounts of core-1 positive microorganisms are obtained in shorter time and with less culturing steps. Furthermore, no production steps for enrichment of core-1 positive microorganisms are necessary. In particular, production of the core-1 positive microorganisms according to the present invention may be performed using a simple batch culture without a feeding phase or using only one feeding phase.

Therefore, in a first aspect, the present invention provides a core-1 positive microorganism of the species *Bacteroides xylanisolvens* or a core-1 positive lysate or fraction thereof, wherein said microorganism or lysate or fraction thereof is recognized by at least one core-1 specific antibody.

In a second aspect, the present invention provides a composition, comprising core-1 positive microorganisms or a core-1 positive lysate or fraction thereof according to the first aspect of the present invention. According to one embodiment, said composition is a cell culture.

In a third aspect, the present invention provides the microorganism according to the first aspect of the invention or the composition according to the second aspect of the invention for use in medicine.

According to a fourth aspect, a pharmaceutical composition is provided, comprising a core-1 positive microorganism or a core-1 positive lysate or fraction thereof according to the first aspect of the invention and/or a composition according to the second aspect of the present invention.

According to a fifth aspect, the present invention provides a method for manufacturing a core-1 positive product, comprising the following steps:
  a) providing a core-1 positive microorganism according to the first aspect of the present invention;
  b) optionally processing said core-1 positive microorganism in order to obtain a core-1 positive lysate or fraction thereof;
  c) using said core-1 positive microorganism and/or said core-1 positive lysate or fraction thereof in the manufacture of the core-1 positive product.

Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

The present inventors have found core-1 positive microorganisms of the species *Bacteroides xylanisolvens*. Therefore, in a first aspect, the present invention is directed to a core-1 positive microorganism of the species *Bacteroides xylanisolvens* or a core-1 positive lysate or fraction thereof, wherein said microorganism or lysate or fraction thereof is recognized by at least one core-1 specific antibody. As discussed above, it was surprisingly found that microorganisms of the species *Bacteroides xylanisolvens* exist that express a core-1 antigen and furthermore, that these microorganisms show an advantageous core-1 antigen expression profile in that they show a stable, high core-1 antigen expression which is e.g. not achieved by core-1 positive microorganisms of other *Bacteroides* species, such as e.g. *Bacteroides ovatus*.

The core-1 positive microorganism according to the present invention carries a core-1 antigen. The term "core-1 antigen" as used herein in particular refers to an antigen which is recognized and thus specifically bound by a core-1-specific antibody. Binding by a core-1 specific antibody can be tested by bringing the core-1 specific antibody under appropriate binding conditions into contact with the core-1 antigen, respectively the core-1 antigen carrying microorganism and/or the core-1 antigen carrying lysate or fraction thereof. Suitable core-1 specific antibodies are known in the prior art (see e.g. WO 2008/055703) and are also described herein. Preferably, the core-1 antigen of the microorganism according to the present invention is bound by at least two core-1 specific antibodies, wherein each of said core-1 specific antibodies recognizes different epitopes of the core-1 antigen. Preferably, the core-1 antigen is present on the surface of the microorganism according to the present invention in an exposed form. Exposed in particular means that the core-1 antigen is accessible from the surrounding medium and thus, can be bound by a core-1 specific antibody upon contact. An exposed core-1 antigen is e.g. not embedded in and thus masked by other structures, in particular other carbohydrate structures. The core-1 antigen that is present on the core-1 positive microorganism according to the present invention is not necessarily identical to the natural core-1 that is found on proteins on tumors (for a description of natural core-1, see above). For the present invention it is only decisive that the core-1 antigen on the microorganism according to the present invention is bound by a core-1 specific antibody because this ensures that said core-1 antigen is capable of mimicking the core-1 structure, thereby being capable of stimulating a core-1 specific immune response. Preferably, the core-1 antigen of the microorganism according to the present invention is or comprises a carbohydrate structure. According to a preferred embodiment, the core-1 antigen expressed by the microorganism according to the present invention comprises the core-1 disaccharide structure Gal-beta1,3-GalNAc. The core-1 antigen is usually linked to a backbone structure, preferably a saccharide structure, in particular an oligo- or polysaccharide structure. Preferably, the linkage between the core-1 disaccharide structure Gal-beta1,3-GalNAc and the backbone structure is alpha-anomeric. Beta-anomeric is another option. Preferably, it is a glycosidic linkage. The (preferably alpha-anomeric) glycosidic linkage can e.g. be established between the Gal-beta1,3-GalNAc structure of the core-1 antigen and a GalNAc molecule of the backbone structure. According to a preferred embodiment, the core-1 antigen is present within the branching structure of capsular polysaccharides of the microorganism according to the present invention.

According to the present invention, a microorganism of the species *Bacteroides xylanisolvens* in particular refers to a microorganism which belongs to the genus *Bacteroides* and which preferably has one or more of the following characteristics:
a) in a DNA-DNA hybridization assay, it shows a DNA-DNA relatedness of at least 30%, preferably at least 50%, at least 70%, at least 80%, at least 90%, preferably at least 95%, more preferred at least 98% or at least 99% with the *Bacteroides xylanisolvens* deposited as DSM 18836 or DSM 25004;
b) it displays a level of 16S rRNA gene sequence similarity of at least 95%, preferably at least 97%, at least 98%, preferably at least 99%, more preferably at least 99.5% with the *Bacteroides xylanisolvens* deposited as DSM 18836 or DSM 25004;
c) it has one or more of the following characteristics:
  i) as the *Bacteroides xylanisolvens* deposited as DSM 18836, it is not able to degrade starch;
  ii) it has the ability to use and/or metabolize mannitol, in particular D-mannitol, melezitose and/or sorbitol, in particular D-sorbitol, and/or to produce acid from glycerol;
  iii) it expresses a glutamyl glutamic acid arylamidase activity;
  iv) it is unable to produce indole;
  v) it does not show catalase activity; and/or
d) it has one or more of the following characteristics:
  i) it is an anaerobic microorganism;
  ii) it is non-spore-forming;
  iii) it is non-motile; and/or
  iv) it is Gram negative.

Preferably, at least two or at least three, and more preferred all of the above defined criteria a) to d) are fulfilled.

The term "DNA-DNA relatedness" in particularly refers to the percentage similarity of the genomic or entire DNA of two microorganisms as measured by the DNA-DNA hybridization/renaturation assay according to De Ley et al. (1970) Eur. J. Biochem. 12, 133-142 or Huβ et al. (1983) Syst. Appl. Microbiol. 4, 184-192. In particular, the DNA-DNA hybridization assay preferably is performed by the DSMZ (Deutsche Sammlung von Mikroorganismen and Zellkulturen GmbH, Braunschweig, Germany) Identification Service. In one embodiment, the DNA-DNA hybridization assay is performed as described in example 1.3, below.

The term "16S rRNA gene sequence similarity" in particular refers to the percentage of identical nucleotides between a region of the nucleic acid sequence of the 16S ribosomal RNA (rRNA) gene of a first microorganism and the corresponding region of the nucleic acid sequence of the 16S rRNA gene of a second microorganism. Preferably, the region comprises at least 100 consecutive nucleotides, more preferably at least 200 consecutive nucleotides, at least 300 consecutive nucleotides or at least 400 consecutive nucleotides, most preferably about 480 consecutive nucleotides. In one embodiment, the region of the nucleic acid sequence of the 16S rRNA gene is flanked by the sequences of SEQ ID NOs: 20 and 21 or their complementary sequences, respectively.

The term "core-1 expression level" as used herein in particular refers to the amount of core-1 antigens present in the microorganism according to the present invention and in particular refers to the amount of core-1 antigens on the surface of said microorganism. The core-1 antigen expression can be e.g. determined by binding of core-1 specific antibodies (such as e.g. Nemod-TF1 and/or Nemod-TF2 (Glycotope GmbH, Berlin); other suitable core-1 specific antibodies are described below) and measuring the amount of bound antibodies, in particular using an ELISA method, for example a method as described herein in example 2. The more core-1 specific antibody is bound, the higher the core-1 expression. Generally, the core-1 antigen expression level is determined using a defined number of cells/microorganisms. In particular, in case two or more expression levels are compared to each other, a similar number of cells/microorganisms is used for determining each expression level or the expression levels are adjusted to the same number of cells/microorganisms mathematically. Furthermore, when comparing core-1 expression levels of different samples, the microorganisms in these samples preferably were cultured under similar conditions and in particular identical conditions. For example, *Bacteroides* microorganisms such as *Bacteroides xylanisolvens* and in particular the microorganisms according to the invention are cultivated in Wilkins-Chalgren (WC) medium (Oxoid Ltd., UK) under anaerobic conditions at 37° C. overnight.

The average core-1 antigen expression level is preferably determined by plating a sample of a culture, picking single colonies after incubation and determining the core-1 antigen expression level of picked colonies. E.g. the average core-1 antigen expression can be determined by randomly picking 10 colonies of the plated culture, determining the core-1 expression level for each colony (see above), adding the obtained values and dividing the added values by 10. The average core-1 expression level may also be correspondingly determined by measuring the expression level of one or more samples of one or more cultures without prior plating and picking of a single colony. In this case, for example several samples of one culture or one sample each of several cultures comprising the microorganisms to be analyzed, wherein said samples should contain approx. the same number of cells/microorganisms, are analyzed and the core-1 antigen expression level of these samples is determined, e.g. by using an ELISA assay as described herein. From the obtained individual values, the average value is determined. The core-1 antigen expression level is preferably determined by using an ELISA assay. A suitable ELISA test for determining the core-1 antigen expression is described in example 2. According to one embodiment, the core-1 positive microorganism according to the present invention preferably achieves on average an absorbance value of at least 0.2, at least 0.25, preferably at least 0.3 and more preferably at least 0.35 in an ELISA assay, using at least one core-1 specific antibody, when performing an ELISA assay as described in example 2, below. A core-1 positive microorganism having a respective high core-1 antigen expression level is advantageous as it is capable of inducing a strong immune response.

Furthermore, the microorganism according to the invention preferably exhibits an average core-1 antigen expression on its surface which is at least 60%, preferably at least 70%, more preferably at least 80%, at least 85%, preferably at least 90%, most preferred at least 95% of the average core-1 expression of Coreotics (DSM 25004) when cultured under the same conditions.

As discussed above, the microorganism according to the present invention is in particular characterized by a stable core-1 antigen expression. Preferably, the following stability degrees are achieved. According to one embodiment, in a culture of the microorganism according to the present invention, at least 30%, preferably at least 50%, at least 70%, at least 80%, at least 85%, preferably at least 90% and more preferred at least 95% of the microorganisms according to the invention have a core-1 antigen expression level which is at least 50%, preferably at least 60%, at least 70%, more preferred at least 75% and most preferred at least 80% of the average core-1 expression level of all microorganisms according to the invention in said cell culture. Preferably, at least 95% of the microorganisms according to the invention in the culture have a core-1 expression level which is at least 75%, preferably at least 80% of the average core-1 expression level of all microorganisms according to the invention in the culture. In essence, only a small number of the microorganisms in the culture do not show a significant core-1 antigen expression. According to one embodiment, at least 30%, preferably at least 50%, at least 70%, at least 80%, at least 85%, preferably at least 90% and more preferred at least 95% of the microorganisms according to the invention in the culture have a core-1 antigen expression level which is at least 50%, preferably at least 60%, at least 70%, at least 75%, more preferred at least 80% of the average core-1 expression level of Coreotics deposited as DSM 25004. Preferably, at least 95% of the microorganisms according to the invention in the culture have a core-1 expression level which is at least 75%, preferably at least 80% of the average core-1 expression level of Coreotics deposited as DSM 25004. The core-1 expression level, respectively the stability of the core-1 expression of a microorganism in a culture can, for example, be determined by plating a sample of the culture, picking single colonies after incubation and determining the core-1 expression level of the picked colonies. In particular, if for example at least 90% of the microorganisms of the culture shall have a specific expression level, then at least 9 out of 10 colonies analyzed as described above shall have the specified expression level. The core-1 expression levels of different clones or cultures are preferably determined under similar conditions, more preferably under identical conditions. In particular, the different clones or cultures are preferably cultivated under similar or identical conditions, for example as described above.

Furthermore, the microorganism according to the present invention is also characterized by a homogeneous expression of the core-1 antigen. Preferably, the following homogeneity degrees are achieved. In a cell culture, preferably, at least 30%, preferably at least 50%, at least 70%, at least 80%, at least 85%, preferably at least 90% and more preferred at least 95% of the microorganisms according to the invention in said cell culture have a core-1 antigen expression level which is in the range of from 60% to 150%, from 70% to 140%, preferably from 70% to 130%, from 75% to 125%, from 80% to 120%, or form 85% to 115%, and most preferably from 90% to 110% of the average core-1 antigen expression level of all microorganisms according to the invention in said cell culture. In particular, at least 95% of the microorganisms according to the invention in said cell culture have a core-1 expression level which is in the range of from 75% to 125%, preferably 80% to 125% of the average core-1 expression level of all microorganisms according to the invention in the culture. In essence, only a small number of the microorganisms in the culture show a core-1 antigen expression which greatly varies from the average core-1 expression in the culture. According to one embodiment, at least 30%, preferably at least 50%, at least 70%, at least 80%, at least 85%, preferably at least 90% and more preferred at least 95% of the microorganisms according to the invention in said culture have a core-1 antigen expression level which is in the range of from 60% to 150%, from 70% to 140%, preferably from 70% to 130%, from 75% to 125%, from 80% to 120%, or form 85% to 115%, and most preferably from 90% to 110% of the average core-1 antigen expression of Coreotics deposited as DSM 25004. Preferably, at least 95% of the microorganisms according to the invention in said cell culture have a core-1 expression level which is in the range of from 75% to 125%, preferably 80% to 125% of the average core-1 expression level of Coreotics deposited as DSM 25004. The homogeneity is preferably determined as described above with respect to the stable core-1 antigen expression.

The core-1 antigen expression level is preferably determined as described above.

Figure 4:
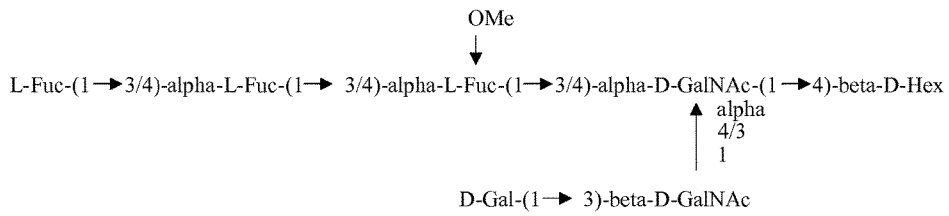
Figure 4:
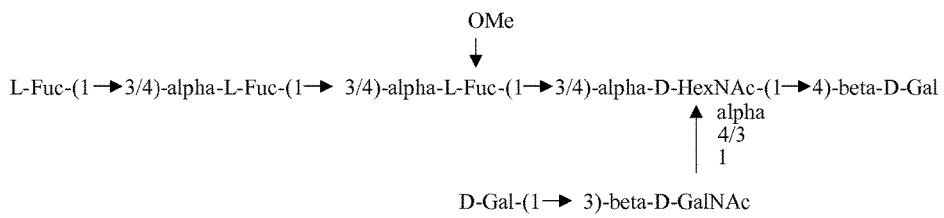
Figure 4:
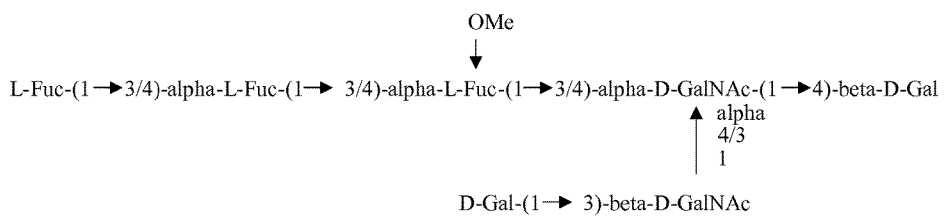
Figure 4:
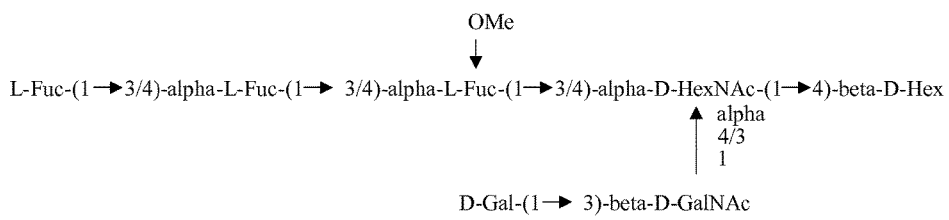
Figure 4:
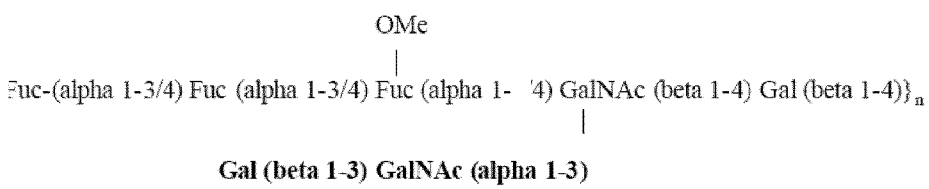

According to one embodiment, the core-1 antigen of the microorganism according to the present invention comprises at least one carbohydrate structure selected from the group consisting of structures #1, #2, #3, #4 and #5 of FIG. 4, analogous structures thereof, and/or repeating units thereof. Said analogous structures comprise the core-1 carbohydrate structure Galβ1,3-GalNAc and preferably consist of the same number and in particular the same type and/or positioning of the monosaccharide units of structures #1, #2, #3, #4 and #5 of FIG. 4. However, the analogous structures may in particular differ from structures #1, #2, #3, #4 and #5 of FIG. 4 in the linkages (alpha- or beta-anomeric linkages, position of the attachment) and modifications (methylation, acetylation) of the monosaccharide units. These analogous structures in particular include structures identical to those of FIG. 4 except that the Galβ1,3-GalNAc disaccharide is attached via an alpha or beta linkage to position 3 or 4 of the monosaccharide unit of the remaining saccharide structure and/or that one or more of the fucose units may be methylated (not necessarily the third fucose unit as shown in FIG. 4). Preferably, analogous structures of the structures of FIG. 4 have the following formula:

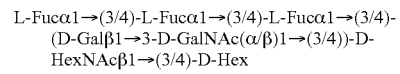

wherein the hexose units (Hex and HexNAc) preferably are galactose units (Gal and GalNAc, respectively), and wherein one or more of the fucose units may be methylated.

According to one embodiment, said core-1 antigen comprises the core-1 carbohydrate structure Galbeta 1,3-GalNAc which is preferably bound in an alpha-anomeric configuration to a backbone structure, preferably a carbohydrate structure. However, the structure Galbeta 1,3-GalNAc may alternatively be bound in a beta-anomeric configuration to the backbone structure. Preferably, the core-1 carbohydrate structure Galbeta 1,3-GalNAc is present as a branching component within a repeating unit of an oligo- or polysaccharide. This exposed presentation of the core-1 antigen on the microorganism according to the present invention has advantageous effects on the induced immune response.

As the microorganism according to the present invention expresses a core-1 antigen on its cell surface, it is thus recognized and accordingly bound by at least one core-1 specific antibody if said core-1 specific antibody is contacted with the core-1 positive microorganism under appropriate binding conditions. Binding can be tested e.g. by using an ELISA test. Suitable binding conditions are e.g. described in example 2.

Core-1 specific antibodies are described and defined in WO 2008/055703 and WO 2004/050707, herein incorporated by reference. Core-1 specific antibodies in particular specifically bind core-1, which in particular is the disaccharide Gal-β1,3-GalNAc which is β-glycosidically linked in an alpha-anomeric configuration to the hydroxy amino acids serine or threonine of proteins in carcinoma cells. The term core-1 specific antibody in particular refers to an antibody that recognizes core-1 only, or, less preferred, that recognizes core-1 and core-2 (Galbeta1-3(GlcNAcbeta1-6)Gal- NAcalpha). The core-1 specific antibodies preferably do not exhibit any cross-reactivity with other derivatives and anomers of said carbohydrate structures such as given in Example 7 of WO 2004/050707 under the binding conditions described therein. A core-1 specific antibody as used herein in particular specifically binds to Galβ1-3GalNAcα1-polyacrylamide (TFα-PAA, TFa-PAA, TFalpha-PAA, Core-1-PAA) but not to any of the substances of list no. 1:

List No. 1
GlcNAcβ1-2Galβ1-3GalNAcα-PAA (GlcNAcβ1-2' TF)
Fucα1-2Galβ1-3GalNAcα-PAA (H type 3)
GalNAcα1-3Galβ-PAA ($A_{di}$)
Galα1-3-GalNAcβ-PAA ($T_{alpha\beta}$)

which can be obtained e.g. from Lectinity holdings, Inc. Alternatively, all structures can be generated by one skilled in the art, who also can select another suitable polyacrylamide for conjugation or another suitable carrier molecule as well as the suitable conjugation methods for coupling of the according carbohydrate structures and the synthesis of the necessary intermediates.

Preferably, said core-1 specific antibody has one ore more of the following characteristics:

a) it binds to asialoglycophorin (carrying core-1) but not glycophorin (not carrying core-1), and this binding is preferably periodate sensitive;
b) it binds to TFalpha-PAA and less or not to TFbeta-PAA (Galbeta 1-3GalNAcbeta1-polyacrylamide) and which binds to asialoglycophorin and not to glycophorin and this binding is preferably periodate sensitive;
c) it binds to TFalpha-PAA and less or not to TFbeta-PAA and which binds to asialoglycophorin and not to glycophorin and which binds to at least one human tumor cell line out of NM-D4 [DSM ACC2605], NM-F9 [DSM ACC2606], and whereby the binding is preferably periodate sensitive; and/or
d) it has one or more of the binding characteristics a) to c) but it does not bind to the trisaccharide core-2 coupled to PAA, such as e.g. NEMOD-TF1.

Preferably, at least two, more preferred at least three, most preferred all of the above defined criteria a) to d) are fulfilled.

Said core-1 specific antibody can be a whole antibody from any animal or human such as murine, rat, human, camel, humanized or chimaeric antibody of different antibody classes such as but not limited to IgM, IgG, IgG1, IgG2, IgG3, IgG4, IgA, IgE, IgD or any fragment of an antibody as long as it comprises the binding specificity against core-1, such as Fab, F(ab)$_2$, single chain Fv, or single domain antibodies. Those antibodies can also contain at least one additional amino acid or mutations or polypeptide sequences, such as tags, linkers or multimerization domains and they can also originate from other sources than animals, such plants and such as selection from synthetic antibody libraries using for example phage display or ribosome display or by recombinant construction. The term "antibody" also includes antibodies such as heavy chain antibodies, i.e. antibodies only composed of one or more, in particular two heavy chains, and nanobodies, i.e. antibodies only composed of a single monomeric variable domain, as well as fragments or derivatives of an antibody.

"Specific binding" preferably means that the antibody binds stronger to a target such as an epitope for which it is specific (here: core-1) compared to the binding to another target. An agent binds stronger to a first target compared to a second target if it binds to the first target with a dissociation constant ($K_d$) which is lower than the dissociation constant for the second target. Preferably, the dissociation constant for the target to which the agent binds specifically is more than 2-fold, preferably more than 5-fold, more preferably more than 10-fold, even more preferably more than 20-fold, 50-fold, 100-fold, 200-fold, 500-fold or 1000-fold lower than the dissociation constant for the target to which the agent does not bind specifically. Preferably, the dissociation constant for the target, here core-1, is in the μM or nM range. In preferred embodiments, the dissociation constant of the binding of the antibody to its specific target, here core-1, is 10 μM or less, preferably 5 μM or less, 2 μM or less, or 1 μM or less, more preferably 500 nM or less, 200 nM or less, 100 nM or less, 50 nM or less, or nM or less, and most preferably 10 nM or less. The dissociation constant preferably is determined at standard conditions, e.g. at 20° C. or room temperature and physiological buffer conditions, e.g. in saline or an aqueous solution containing 150 mM NaCl and 10 mM Tris/HCl pH 7.

Suitable core-1 binding antibodies are described e.g. in WO2004/050707 and WO 2008/055703. Examples are HB-T1 (IgM) [obtainable from DakoCytomation GmbH, Hamburg; Giuffre G, Vitarelli E, Tuccari G, Ponz de Leon M, Barresi G: Detection of Tn, sialosyl-Tn and T antigens in hereditary nonpolyposis colorectal cancer. Virchows Arch 429:345-352 (1996)], HH8 (IgM) [Clausen H, Stroud M, Parker J, Springer G, Hakomori S: Monoclonal antibodies directed to the blood group A associated structure, galactosyl-A: specificity and relation to the Thomsen-Friedenreich antigen. Mol Immunol 25:199-204 (1988)], Nemod-TF1 [Glycotope GmbH, Berlin; Goletz S, Cao Y, Danielczyk A, Ravn P, Schoeber U, Karsten U. Thomsen-Friedenreich antigen: the "hidden" tumor antigen. Adv Exp Med. Biol. 2003; 535: 147-62], and Nemod-TF2 [Glycotope GmbH, Berlin; Goletz S, Cao Y, Danielczyk A, Ravn P, Schoeber U, Karsten U: Thomsen-Friedenreich antigen: the "hidden" tumor antigen. Adv Exp Med Biol. 2003; 535: 147-62].

Particularly suitable for determining that a microorganism is core-1 positive and/or for determining the level of core-1 antigen expression is the use of the antibodies mIgM-Karo2, mIgM-Karo4, cIgG-Karo4 and/or cIgM-Karo4 disclosed on pages 16 to 18 of the sequence listing of WO2004/050707, herein incorporated by reference, or the use of antibodies having a corresponding binding specificity and affinity.

According to one embodiment, the core-1 positive microorganism according to the present invention or the core-1 positive lysate or fraction thereof is bound by a core-1 specific antibody which comprises one of the following sets of complementarity-determining regions (CDRs):

Set 1:
heavy chain CDRs: SEQ ID NO: 1 (CDR-H1); SEQ ID NO: 2 (CDR-H2); SEQ ID NO: 3 (CDR-H3); and
light chain CDRs: SEQ ID NO: 4 (CDR-L1); SEQ ID NO: 5 (CDR-L2); SEQ ID NO: 6 (CDR-L3)

Set 2:
heavy chain CDRs: SEQ ID NO: 7 (CDR-H1); SEQ ID NO: 8 (CDR-H2); SEQ ID NO: 9 (CDR-H3); and
light chain CDRs: SEQ ID NO: 10 (CDR-L1); SEQ ID NO: 11 (CDR-L2); SEQ ID NO: 12 (CDR-L3)

The antibody having Set 1 of CDRs as defined above preferably comprises a heavy chain comprising the amino acid sequence according to SEQ ID NO: 13 and/or a light chain comprising the amino acid sequence according to SEQ ID NO: 16, or a heavy chain comprising the amino acid sequence according to SEQ ID NO: 14 or 15 and/or a light chain comprising the amino acid sequence according to SEQ ID NO: 17. The antibody having Set 2 of CDRs as defined above preferably comprises a heavy chain comprising the amino acid sequence according to SEQ ID NO: 18 and/or a light chain comprising the amino acid sequence according to SEQ ID NO: 19.

Commercially available, particularly suitable core-1 specific antibodies are e.g. Nemod-TF1 and Nemod-TF2 (available from Glycotope GmbH, Berlin). These antibodies are highly specific for core-1.

Antibodies comprising the CDR Set 1 and antibodies comprising the CDR Set 2 are both specific for core-1, however, these antibodies bind core-1 from two different angles and thus bind different epitopes. Similarly, also Nemod-TF1 and Nemod-TF2 both specifically bind the core-1 carbohydrate structure but bind different epitopes. Binding of the core-1 positive microorganism according to the present invention or the core-1 positive lysate or fraction thereof by at least two different core-1 specific antibodies which recognize different epitopes on the core-1 carbohydrate structure ensures that the core-1 antigen is present in an exposed, accessible form on the cell surface. Thus, according to one embodiment, the core-1 positive microorganism according to the present invention or the core-1 positive lysate or fraction thereof is bound by an antibody having Set 1 of CDRs as defined above as well as by an antibody having Set 2 of CDRs as defined above and/or the core-1 positive microorganism according to the present invention or the core-1 positive lysate or fraction thereof is bound by Nemod-TF1 and Nemod-TF2.

According to one embodiment, the microorganism according to the present invention is not bound by the antibody A68-B/A11 (Glycotope, Berlin) which binds TFbeta.

According to one embodiment, binding of the at least one core-1 specific antibody to the core-1 positive microorganism according to the present invention or the core-1 positive lysate or fraction thereof is periodate sensitive, in that the binding of the core-1 specific antibody is reduced or even absent after periodate treatment. A periodate treatment leads to the partial degradation of the surface carbohydrate moieties. Thus, with a core-1 positive microorganism which carries the core-1 antigen in an exposed and thus non-hidden (respectively non-masked) form, a periodate treatment destroys the structure of core-1 antigens present on the cell surface which results in that core-1 specific antibodies can no longer bind after the periodate treatment because the core-1 antigen is no longer present, respectively intact. On the other hand, microorganisms which do not carry a core-1 antigen, in particular a core-1 carbohydrate antigen, but merely carry core-1-like carbohydrate antigens wherein the core-1 antigen is e.g. masked by further saccharide units and which, accordingly, are not bound by core-1 specific antibodies without a prior treatment, can reveal a core-1 antigen after periodate treatment. The binding of the at least one core-1 specific antibody to the microorganism according to the present invention preferably is periodate sensitive, i.e. a treatment with periodate results in that the core-1 specific antibody does no longer bind the periodate treated microorganism or shows at least a reduced binding after periodate treatment. According to one embodiment, the lysate or fraction of the microorganism according to the present invention has the same characteristics.

A periodate treatment according to the invention in particular refers to the exposure of the material to be treated to a solution containing periodate at a concentration effective for at least partial oxidation of saccharide units. For example, a periodate treatment may be effected by incubating the material to be treated for 5 min in a solution of 50 mM sodium acetate buffer following by incubation for 1 h in a solution of 10 mM sodium periodate. After washing again with a solution of 50 mM sodium acetate buffer, the action of periodate is stopped through incubation for 30 min in dark in a solution of 50 mM sodium borohydride.

Furthermore, the core-1 antigen on the surface of the microorganism according to the present invention or the lysate or fraction thereof preferably is accessible from the surrounding medium, in particular is accessible for a core-1 specific antibody in the surrounding medium and thus is exposed on the cell surface.

The microorganism according to the invention in particular is an isolated microorganism which preferably is not present in its natural environment. In particular, the microorganism is not present inside the human body, preferably it is not present inside a human or animal body. According to one embodiment, the microorganism according to the invention has been isolated from a composition comprising microorganisms which are either not core-1 positive and/or do not belong to the species *Bacteroides xylanisolvens*. According to one embodiment, the microorganism according to the present invention is present in or is obtained from a culture comprising at least 70%, at least 80%, at least 90%, preferably at least 95%, 97%, 99%, most preferred about 100% of microorganisms according to the present invention.

The term "a microorganism" as used herein may refer to only one unicellular organism as well as to numerous single unicellular organisms. For example, the term "a microorganism of the species *Bacteroides xylanisolvens*" may refer to one single *Bacteroides xylanisolvens* bacterial cell of the species *Bacteroides xylanisolvens* as well as to multiple bacterial cells of the species *Bacteroides xylanisolvens*. The terms "a microorganism of the species *Bacteroides xylanisolvens*" and "a *Bacteroides xylanisolvens* microorganism" are used synonymously herein. Preferably, the term "a microorganism" refers to numerous bacterial cells. In particular, said term refers to at least $10^3$ bacterial cells, preferably at least $10^4$ bacterial cells, at least $10^5$ or at least $10^6$ bacterial cells.

The *Bacteroides xylanisolvens* microorganism according to the present invention preferably is capable of producing short chain fatty acids (SCFAs). Short chain fatty acids (SCFAs) produced as end products of microbial carbohydrate fermentation may have health promoting properties. As an example, propionate was reported to have potential cholesterol reducing effects and anti-lipogenic effects. It may further stimulate satiety and along with acetate and butyrate present an anti-carcinogenic effect. In preferred embodiments, the microorganism according to the invention is capable of producing one or more SCFAs selected from the group consisting of propionate, acetate, succinate, formate and lactate. Preferably, it is capable of producing propionate and/or acetate. In preferred embodiments, these SCFAs are also present in the compositions according to the present invention which contain the microorganism according to the invention or a lysate or fraction thereof. In certain embodiments wherein the microorganism according to the invention is to be administered to the patient in a viable form, said microorganism is still capable of producing said SCFAs inside the patient's body after administration.

In preferred embodiments, the *Bacteroides xylanisolvens* microorganism according to the present invention is capable of surviving the conditions in, in particular the passage through the stomach, and preferably also the conditions in, in particular the passage through at least a part of the intestine of a human being after ingestion. In particular, surviving the conditions in the stomach of a human being refers to the survival for at least 180 min of at least 50%, preferably at least 60%, at least 70%, at least 80% or at least 85% of the *Bacteroides xylanisolvens* microorganisms according to the present invention in a composition comprising the microorganisms in gastric juice. Furthermore, surviving the conditions in the intestine of a human being refers to the survival for at least 240 min of at least 50%, preferably at least 60%, at least 70%, at least 80%, at least 85%, at least 90% or at least 95% of the *Bacteroides xylanisolvens* microorganisms according to the present invention in a composition comprising the microorganisms in intestinal juice. In preferred embodiments, the microorganisms according to the invention still comprise at least one core-1 antigen on their surface after said treatment. More preferably, they still comprise an amount of core-1 antigen on their surface which is at least 50%, preferably at least 60%, at least 70%, at least 80%, at least 90% or at least 95% of the amount of core-1 antigen on their surface at the beginning of the treatment. Furthermore, the microorganisms according to the invention are capable of expressing core-1 on their surface, in particular as described herein, after the above-described treatments. Thus, the core-1 expression of the microorganisms according to the invention is not affected by the conditions in the human gastrointestinal tract and said microorganisms still comprise a high and stable core-1 antigen density on their surface and—if used in a viable form—are still capable of expressing core-1 after oral administration. Therefore, the microorganisms according to the invention are especially advantageous for the use as therapeutic agent in oral formulations.

In preferred embodiments, the *Bacteroides xylanisolvens* microorganism according to the present invention has one or more of the following safety characteristics:
 (i) it is sensitive to the antibiotics metronidazole, meropenem and/or clindamycin;
 (ii) it does not contain the plasmid RP4 (DSM 3876) and/or the plasmid pSC101 (DSM 6202);
 (iii) it does not contain the β-lactamase genes cfiA and/or cfxA;
 (iv) it does not contain the virulence factors polysaccharide A of *Bacteroides fragilis* and/or enterotoxin Bft of *Bacteroides fragilis* and/or "Ton B-Linked outer membrane protein" encoded by the gene ompW;
 (v) it does not show any extracellular DNase activity, extracellular chondroitinase activity, extracellular hyaluronidase activity and/or extracellular neuraminidase activity; and/or
 (vi) it does not attach to epithelial cells of the human colon.

In a preferred embodiment, the *Bacteroides xylanisolvens* microorganism according to the present invention is
a) Coreotics, deposited on Jul. 12, 2011 under the accession number DSM 25004 according to the requirements of the Budapest Treaty at the Deutsche Sammlung von Mikroorganismen and Zellkulturen (DSMZ), Inhoffenstraβe 7B, 38124 Braunschweig (DE) by the Glycotope GmbH, Robert-Rössle-Str. 10, 13125 Berlin (DE), (DSM 25004),
b) a microorganism derived from Coreotics or
c) a Coreotics homolog.

Coreotics (DSM 25004) belongs to the species *Bacteroides xylanisolvens*. Preferably, Coreotics is a strictly anaerobic, non-spore-forming, non-motile and Gram negative rod-shaped bacterium of 0.4-0.5 μm width and generally 1-2 μm length which in particular grows colonies on Wilkins-Chalgren agar which after 18 h are 2-3 mm in diameter with a circular, milky, raised and convex surface. Coreotics exhibits a highly stable, homogeneous, strong core-1 expression on its cell surface. As is shown in example 2, the core-1 antigen expression values determined for 10 different colonies of Coreotics, show OD values in an ELISA assay (see example 2) with little variability in their core-1 antigen expression. Thereby, a constant, homogenous and high amount of core-1 antigen is provided when using Coreotics, e.g. in pharmaceutical compositions. This expression profile is unique and also shows that Coreotics has considerable advantages over other core-1 antigen expressing microorganisms such as e.g. the *Bacteroides ovatus* AG6 DSM 18726 (disclosed in WO 2008/055703), which shows e.g. a higher variability in their core-1 expression than Coreotics. Also encompassed are core-1 positive lysates and fractions of Coreotics.

A microorganism derived from Coreotics and/or a Coreotics homolog preferably has one or more of the following characteristics:
a) it belongs to the species of *Bacteroides xylanisolvens* as defined above;
b) in a DNA-DNA hybridization assay, it shows a DNA-DNA relatedness of at least 30%, preferably at least 50%, at least 70%, at least 80%, at least 90%, or at least 95%, more preferred at least 98% or at least 99% with Coreotics deposited as DSM 25004 and/or the *Bacteroides xylanisolvens* deposited as DSM 18836;
c) it displays a level of 16S rRNA gene sequence similarity of at least 95%, preferably at least 97%, at least 98%, or at least 99%, more preferably at least 99.5%, and most preferably about 100% with Coreotics deposited as DSM 25004 and/or the *Bacteroides xylanisolvens* deposited as DSM 18836;
d) it shows a core-1 antigen expression which has one, two, preferably three, more preferably four, most preferably all of the following characteristics:
 i) it has an average core-1 antigen expression of at least 50%, preferably at least 60%, at least 70%, at least 75%, at least 80%, at least 85%, or at least 90%, more preferably at least 95% of the average core-1 expression of Coreotics deposited as DSM 25004;
 ii) it achieves on average an absorbance value of at least 0.25, preferably at least 0.3 and more preferably at least 0.35 in an ELISA assay as described in example 2;
 iii) it expresses on the cell surface at least one carbohydrate structure selected from the group consisting of structures #1, #2, #3, #4 and #5 of FIG. 4, analogous structures thereof, and/or repeating units thereof;
 iv) in a cell culture, at least 50%, preferably at least 60%, at least 70%, at least 80%, at least 90%, or at least 95%, more preferred about 100% of said microorganisms have a core-1 antigen expression level which is at least 75%, preferably at least 80% of the average core-1 antigen expression of Coreotics deposited as DSM 25004; and/or
 v) in a cell culture, at least 50%, preferably at least 60%, at least 70%, at least 80%, at least 90%, or at least 95%, more preferred about 100% of said microorganisms have a core-1 antigen expression level which is in the range of from 70% to 150%, from 75% to 125%, preferably from 80% to 115%, most preferably from 90% to 110% of the average core-1 antigen expression of Coreotics deposited as DSM 25004;
e) it has one or more of the safety characteristics disclosed above;
f) it survives the conditions in the stomach and/or intestine of a human being and in particular is capable of expressing core-1 after surviving said conditions; and/or
g) it is capable of producing short chain fatty acids, in particular propionate.

Preferably, at least two, more preferably at least three, at least four, at least five or at least six, and most preferred all of the above defined criteria a) to f) are fulfilled.

In a second aspect, the present invention provides a composition comprising core-1 positive microorganisms or a core-1 positive lysate or fraction thereof according to the first aspect of the invention. The comprised core-1 positive microorganisms according to the present invention may be identical or different. With respect to the characteristics of the core-1 positive microorganism of the species *Bacteroides xylanisolvens* according to the first aspect of the present invention, it is referred to the above disclosure. The same applies with respect to core-1 positive lysates, fractions and/or fragments thereof.

Preferably, 80% or more, more preferably 85% or more, 90% or more, 95% or more, 98% or more or 99% or more, and most preferably about 100% of the microorganisms in the composition are core-1 positive microorganisms of the species *Bacteroides xylanisolvens* according to the first aspect of the invention.

In preferred embodiments, the core-1 positive microorganisms in the composition according to the present invention are characterized by a stable core-1 antigen expression. Preferably, the following stability degrees are obtained. According to one embodiment, at least 30%, preferably at least 50%, at least 70%, at least 80%, at least 85%, preferably at least 90% and more preferred at least 95% of the core-1 positive microorganisms in the composition have a core-1 antigen expression level which is at least 50%, preferably at least 60%, at least 70%, more preferred at least 75%, at least 80% of the average core-1 expression level of all core-1 positive microorganisms in said composition. Preferably, at least 95% of the core-1 positive microorganisms in the composition have a core-1 expression level which is at least 75% of the average core-1 expression level of all core-1 positive microorganisms in the composition. According to one embodiment, at least 30%, preferably at least 50%, at least 70%, at least 80%, at least 85%, preferably at least 90% and more preferred at least 95% of the core-1 positive microorganisms in the composition have a core-1 antigen expression level which is at least 50%, preferably at least 60%, at least 70%, at least 75%, at least 80% of the average core-1 expression level of Coreotics deposited as DSM 25004. Preferably, at least 95% of the core-1 positive microorganisms in the composition have a core-1 expression level which is at least 75% of the average core-1 expression level of Coreotics deposited as DSM 25004. Preferably, said core-1 positive microorganisms are of the species *Bacteroides xylanisolvens*.

According to a preferred embodiment, the core-1 positive microorganisms in the composition according to the present invention are characterized by a homogeneous expression of the core-1 antigen. Preferably, the following homogeneity degrees are achieved. Preferably, at least 30%, preferably at least 50%, at least 70%, at least 80%, at least 85%, preferably at least 90% and more preferred at least 95% of the core-1 positive microorganisms in the composition have a core-1 antigen expression level which is in the range of from 60% to 150%, from 70% to 140%, preferably from 70% to 130%, from 75% to 125%, from 80% to 120%, or form 85% to 115%, and most preferably from 90% to 110% of the average core-1 antigen expression of all core-1 positive microorganisms in the composition. In particular, at least 95% of the core-1 positive microorganisms in the composition have a core-1 expression level which is in the range of from 75% to 125% of the average core-1 expression level of all core-1 positive microorganisms in the composition. According to one embodiment, at least 30%, preferably at least 50%, at least 70%, at least 80%, at least 85%, preferably at least 90% and more preferred at least 95% of the core-1 positive microorganisms in the composition have a core-1 antigen expression level which is in the range of from 60% to 150%, from 70% to 140%, preferably from 70% to 130%, from 75% to 125%, from 80% to 120%, or form 85% to 115%, and most preferably from 90% to 110% of the average core-1 antigen expression of Coreotics deposited as DSM 25004. In particular, at least 95% of the core-1 positive microorganisms according to the invention in the composition have a core-1 expression level which is in the range of from 75% to 125% of the average core-1 expression level of Coreotics deposited as DSM 25004. Preferably, said core-1 positive microorganisms are of the species *Bacteroides xylanisolvens*.

Means to determine the core-1 antigen expression level as well as the stability and homogeneity are described above.

According to one embodiment, the composition according to the second aspect is a cell culture. Preferred values for a cell culture comprising the core-1 positive microorganisms according to the present invention are described above in conjunction with the first aspect according to the present invention.

According to one embodiment, the microorganism or the microorganisms in the composition are present in a viable, non-reproductive, non-viable or lysed form. According to one embodiment, only core-1 positive fractions of said microorganisms are used in said composition according to the second aspect of the present invention.

Preferably, the composition comprises at least $10^3$ microorganism according to the present invention, more preferably at least $10^4$, at least $10^5$ or at least $10^6$ microorganism according to the present invention; or the core-1 positive lysates or fractions of this amount of microorganisms according to the present invention.

In a third aspect, the present invention provides the core-1 positive microorganism or the core-1 positive lysates or fractions thereof according to the first aspect of the invention or the composition according to the second aspect of the invention for use in medicine. The core-1 positive microorganism, lysate or fraction thereof and/or the composition according to the present invention is preferably used for inducing and/or enhancing an immune response against core-1. The induced or enhanced immune response may be a humoral and/or a cellular immune response and in particular involves the induction of an antibody titer against core-1. Thereby, core-1 positive tumors, cancers, gastrointestinal disorders and/or core-1 positive diseases can be treated and/or prevented. The induced and/or enhanced core-1 specific immune response functions as a shield against e.g. core-1 positive cancer cells in particular for the prevention, reduction or spread of core-1 positive tumors or metastasis. The core-1 positive microorganism or the core-1 positive lysates or fractions thereof according to the first aspect of the invention or the composition according to the second aspect of the invention can also be used as vaccine against cancer. Suitable other therapeutic uses of core-1 positive microorganisms are also described in WO 2008/055703, herein incorporated by reference.

In particular, the core-1 positive microorganism or the core-1 positive lysates or fractions thereof according to the first aspect of the invention or the composition according to the second aspect of the invention can be administered to a patient having cancer or being at risk of developing cancer. According to one embodiment, the core-1 positive microorganism according to the invention expressing a core-1 antigen on its surface or the core-1 positive lysate or fraction thereof is capable of eliciting a specific immune response against a core-1 antigen in the patient. The immune response may be a humoral and/or cellular immune response, and preferably includes a cellular immune response, in particular a response of the adaptive immune system, preferably including the formation of memory cells of the immune system.

The cancer preferably is a cancer comprising tumor cells carrying the core-1 carbohydrate antigen on their surface (core-1 positive cancer). Preferably, the cancer is a colon carcinoma or a metastasis of a colon carcinoma.

The term "patient" as used herein in particular refers to a human being, a nonhuman primate or another animal, in particular a mammal such as a cow, horse, pig, sheep, goat, dog, cat or a rodent such as a mouse and rat. Preferably, the patient is a human being.

The term "cancer" according to the invention in particular comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are colon carcinomas, colorectal carcinomas, and metastases of the cancer types or tumors described above. The term cancer according to the invention also comprises cancer metastases. The term "tumor" in particular refers to a group of cells or tissue that is formed by misregulated cellular proliferation. Tumors may show partial or complete lack of structural organization and functional coordination with the normal tissue, and usually form a distinct mass of tissue, which may be either benign or malignant. The term "metastasis" in particular refers to the spread of cancer cells from its original site to another part of the body. The formation of metastasis is a very complex process and normally involves detachment of cancer cells from a primary tumor, entering the body circulation and settling down to grow within normal tissues elsewhere in the body. When tumor cells metastasize, the new tumor is called a secondary or metastatic tumor, and its cells normally resemble those in the original tumor. This means, for example, that, if breast cancer metastasizes to the lungs, the secondary tumor is made up of abnormal breast cells, not of abnormal lung cells. The tumor in the lung is then called metastatic breast cancer, not lung cancer.

In accordance with the present invention the term "core-1 positive disease" in particular refers to any disease which is associated with a eukaryotic cell, tumor cell, cancer or other biological material which is characterised by the occurrence of the core-1 tumor antigen (see above).

The present invention also provides in a fourth aspect a pharmaceutical composition, comprising
  i) a core-1 positive microorganism or a core-1 positive lysate or fraction thereof according to the first aspect according to the present invention (details of the core-1 positive microorganism according to the present invention are described above; it is referred to the above disclosure)
  and/or
  ii) a composition according to the second aspect of the present invention (details of the respective composition are described above; it is referred to the above disclosure).

The term "pharmaceutical composition" particularly refers to a composition that is suitable for administering to a human or animal, i.e., a composition containing components which are pharmaceutically acceptable. Preferably, the pharmaceutical composition comprises as active compound the core-1 positive microorganism or a core-1 positive lysate or fraction thereof according to the first aspect and/or the composition according to the second aspect thereof together with a carrier, diluent or pharmaceutical excipient such as buffer, preservative and tonicity modifier. Suitable pharmaceutical uses are described above; it is referred to the above disclosure. The pharmaceutical composition may be administered orally, but may also be administered by any other suitable route of administration.

The pharmaceutical composition according to the invention preferably comprises the core-1 positive microorganism in an amount or concentration resulting in a daily dose of about $10^4$ to about $10^{13}$ microorganisms for the patient. Preferably, the daily dose does not exceed $2.8*10^{12}$ microorganisms, preferably $2.3*10^{12}$ microorganisms, and/or is at least $10^7$ microorganisms, preferably at least $10^9$ microorganisms. In particular, the daily dose is in the range of about $10^{10}$ to about $10^{12}$ microorganisms. The pharmaceutical composition preferably is in the form of single unit doses each comprising a daily dose of the core-1 positive microorganism as described above. For pharmaceutical compositions comprising a core-1 positive lysate or fraction of the core-1 positive microorganism, the amount or concentration of the core-1 positive lysate or fraction in the composition equals that of the core-1 positive microorganism in the composition as described above. In particular, the core-1 positive lysate or fraction in the composition is obtained from an amount or concentration of core-1 positive microorganism as described above.

The core-1 positive microorganism according to the invention and the core-1 positive microorganisms in the composition according to the invention may be used in a viable, non-reproductive, non-viable or lysed form. In certain embodiments, the core-1 positive microorganism is used in a viable form. In particular, when used in a viable form, the microorganism is still capable of producing short chain fatty acids such as propionate in the body of the patient, thereby providing a further health benefit as described above. Preferably, the microorganism are used in a non-pathogenic form, a non-reproductive, non-viable or lysed form. Furthermore, also core-1 positive fractions of said microorganisms may be used. According to the invention, the core-1 positive lysates or fractions of the microorganisms comprise at least one core-1 antigen which preferably is accessible for core-1 specific antibodies as described above and/or is periodate sensitive as described above.

One specific advantage of the core-1 positive microorganism and the pharmaceutical compositions according to the present invention is their ability to induce an antibody titer against core-1 in the human or animal body. This anti-core-1 antibody titer in particular provides a general protection against core-1 positive diseases, in particular cancer comprising core-1 positive tumor or cancer cells. Thus, in preferred embodiments the core-1 positive microorganism according to the invention or the core-1 positive lysate or fragment or fraction thereof or the pharmaceutical compositions according to the present invention are capable of inducing an antibody titer against the core-1 antigen in the human or animal body when administered. The induced antibody titer preferably is at least detectable by common detection methods and preferably is sufficient to reduce the risk of acquiring a core-1 positive disease, in particular cancer comprising core-1 positive tumor or cancer cells.

According to a fifth aspect, the present invention provides a method for manufacturing a core-1 positive product, comprising the following steps:
a) providing a core-1 positive microorganism according to the first aspect of the present invention;
b) optionally processing said core-1 positive microorganism in order to obtain a core-1 positive lysate or fraction thereof;
c) using said core-1 positive microorganism and/or said core-1 positive lysate or fraction thereof in the manufacture of the core-1 positive product.

The product can be any product and includes but is not limited to pharmaceutical products. With respect to the manufacturing of respective products and the details of the core-1 positive microorganisms according to the present invention, it is also referred to the above disclosure. The core-1 positive microorganism according to the first aspect of the present invention can be used in viable or non-viable form. The manufactured product can also be processed further.

The term "fraction of a core-1-positive microorganism" and similar terms as used herein in particular refer to preparations or purifications of smaller parts of said microorganisms such as e.g. a cell wall preparation, envelope preparation, lysates, lipopolysaccharide preparation, preparation of capsules, or capsule polysaccharide preparations of core-1 positive components of said core-1 positive microorganism according to the present invention. Said fractions should comprise at least one core-1 positive component of said core-1 positive microorganism in order to be able to elicit the desired immune response. They can be obtained from preparations or purifications from at least one core-1 positive microorganism according to the present invention. Said preparations and purifications can be obtained by methods known to those skilled in the art such as single or sequential cell fractionation(s), phenol water extractions, ether extractions, enzyme digestions such as digestions with lysozyme or chromatographic methods. Furthermore, the term fraction of a core-1 positive microorganism also comprises artificially produced core-1 positive components which are also found on core-1 positive microorganisms of the present invention.

According to one embodiment, the core-1 positive product that is produced according to the method according to the fifth aspect is an antigen presenting cell, preferably a dendritic cell. In this case, step c) of the method according to the fifth aspect of the present invention preferably comprises loading said antigen presenting cell with the core-1 positive microorganism according to the present invention and/or the core-1 positive lysate or fraction thereof. Preferably, the antigen presenting cell is human. Preferably, the antigen presenting cells are dendritic cells obtained from the leukemia cell line MUTZ-3 (DSM ACC295) or cells derived from MUTZ-3, such as NEMOD-DC (see WO 2003/023023).

In WO 2008/055703 it is described that core-1 positive microorganisms and lysates and/or fractions thereof are capable of activating human T-cells in a core-1 specific manner when presented by a functional antigen presenting cell, in particular a dendritic cells in vitro, thereby opening up new therapeutic opportunities (see WO2008/055703, in particular page 77, lines 26 to page 85, line 20, herein incorporated by reference).

Therefore, according to a sixth aspect of the present invention there is provided a method of manufacturing a functional antigen presenting cell, preferably a dendritic cell, against core-1, which comprises the following steps:
a) providing a core-1 positive microorganism according to the first aspect of the present invention (see also claims 1 to 5)
b) optionally processing said core-1 positive microorganism in order to obtain a core-1 positive lysate or fraction thereof;
c) bringing into contact a suitable amount of at least one antigen presenting cell, preferably a dendritic cell, with a suitable amount of
    i) said core-1 positive microorganism and/or
    ii) said core-1 positive lysate or fraction thereof,
thereby obtaining a functional antigen presenting cell, preferably a dendritic cell, against core-1.

The contacting in step c) occurs for a suitable time and under suitable conditions to generate at least one functional antigen presenting cell, preferably a dendritic cell, against core-1. Preferably, the antigen presenting cell that is contacted in step c) with the core-1 positive compounds is an immature antigen presenting cell such as an immature dendritic cell which is then matured to obtain the functional antigen presenting cell against core-1. Details of said contacting step c) are also described in WO 2008/055703; it is referred to the respective disclosure.

That a functional antigen presenting cell against core-1 has been obtained can be tested by using core-1 specific antibodies as were described above. Functional antigen presenting cells against core-1 are loaded with the core-1 antigen of the used core-1 positive microorganism according to the present invention (or the core-1 positive lysate or fraction thereof, see above). Thus, the core-1 antigen can be detected by core-1 specific antibodies on the respectively loaded antigen presenting cells. The obtained functional antigen presenting cell against core-1 (which can also be a mixture of antigen presenting cells, preferably dendritic cells), can activate T-cells, in particular primary human T-cells, specifically against core-1 and thus, can stimulate a specific cellular immune response against core-1. T-cell activation can be tested e.g. by a cellular immune response test as described in WO 2008/055703.

According to a seventh aspect, there is provided a method of producing an activated T cell, T cells, a T cell clone or a T cell line against core-1 comprising
a) obtaining at least one functional antigen presenting cell, preferably a dendritic cell, against core-1 using the method according to the sixth aspect of the invention;
b) bringing into contact a suitable amount of the functional antigen presenting cell against core-1 with a suitable amount of at least one T cell or a mixture of T cells or a mixture of cells comprising at least one T cell; and
c) cultivating said T cell or mixture of T cells together with said loaded functional antigen presenting cells against core-1 to activate and/or prime a T cell or T cells against core-1.

Details of a corresponding production method that can also be used in conjunction with the present invention are also described in WO 2008/055703; it is referred to the respective disclosure.

Also provided is a functional antigen presenting cell, preferably a dendritic cell, against core-1, an activated T cell or T cells against core-1, a cell composition comprising T cells against core-1, a T cell line against core-1, or a T cell clone against core-1 produced by a method according to the sixth or the seventh aspect according to the present invention, which induces a humoral and/or a cellular immune response against core-1 positive cells and/or diseases.

Respective cells are suitable for manufacturing a medicament for prophylaxis or therapy of core-1 positive diseases, such as in particular core-1 positive tumors.

The invention also pertains to the use of a core-1 positive microorganism and/or a core-1 positive lysate or fraction thereof according to the first aspect of the invention in vivo or in vitro for inducing or enhancing a core-1 specific immune response and/or for generating functional antigen presenting cells, preferably dendritic cells, and/or activated T cells, T cell lines or T cell clones or antibodies against core-1.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

FIGURES

FIG. 1 shows a restriction analysis of the microorganism Coreotics according to the invention and different reference microorganisms. The results support that Coreotics is of the species *Bacteroides xylanisolvens*.

Figure 2:
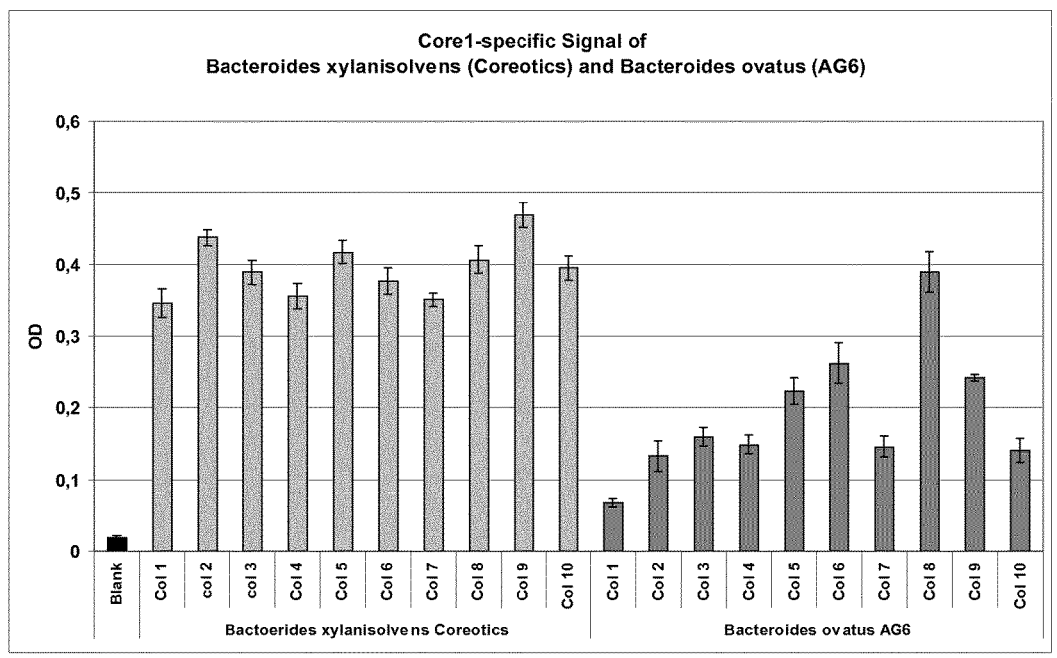

FIG. 2 shows an antigen ELISA binding study of Coreotics (DSM 25004) and AG6 (DSM 18726) using core-1 specific antibodies. Different Coreotics or AG6 colonies were plated in microtiter wells and bound by a core-1 specific antibody. The binding was visualized using a peroxidase-coupled secondary antibody. The ELISA assay shows that Coreotics has a stable and homogeneous expression of the core-1 antigen while AG6 has a less stable and accordingly less homogenous core-1 expression. The average core-1 antigen expression of AG6 was also lower than that of Coreotics.

Figure 3:
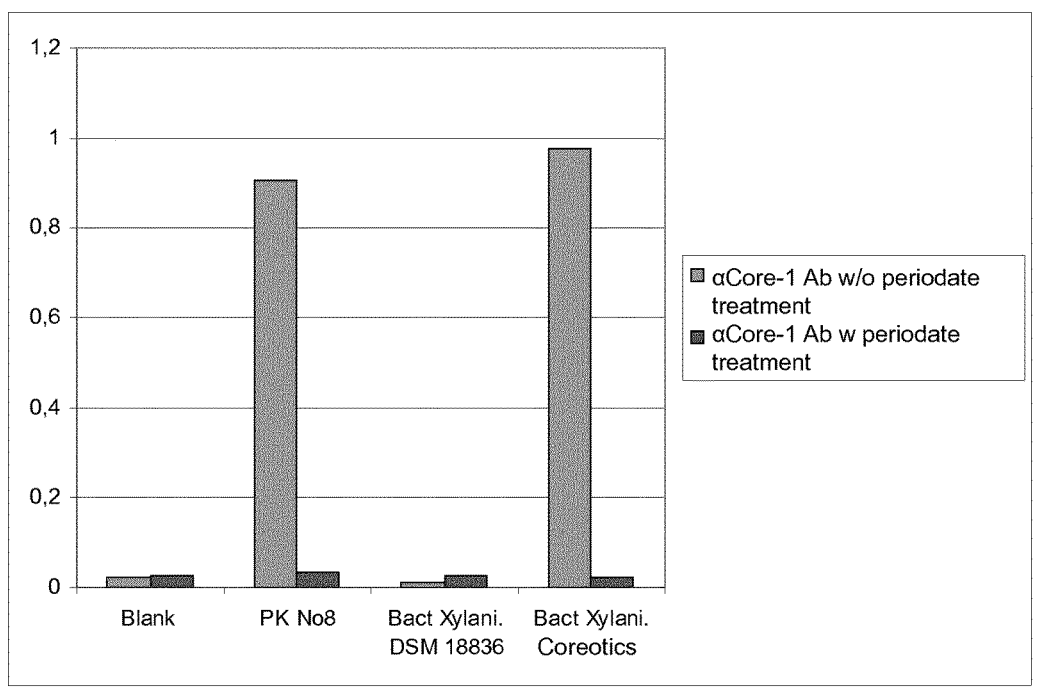

FIG. 3 shows the binding of an anti-core-1 antibody to Coreotics (DSM 25004) using an ELISA assay. A preceding periodate treatment abolished the antibody binding. The same results were obtained for a core-1 positive control (PK). Reference strain *Bacteroides xylanisolvens* DSM 18836 did not show any anti-core-1 antibody binding.

FIG. 4 shows different carbohydrate structures carrying a core-1-like disaccharide motif which may be present on the cell surface of Coreotics microorganisms.

Figure 5:
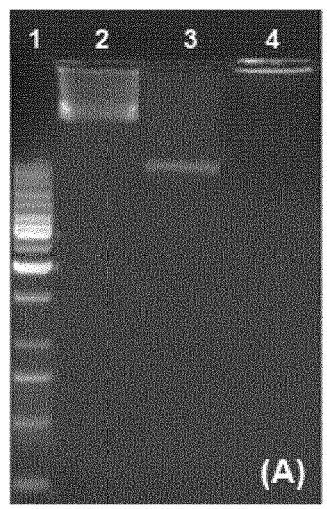
Figure 5:
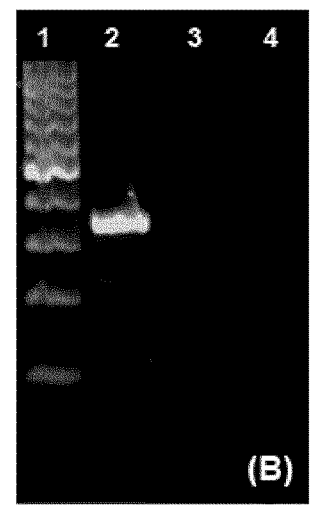
Figure 5:
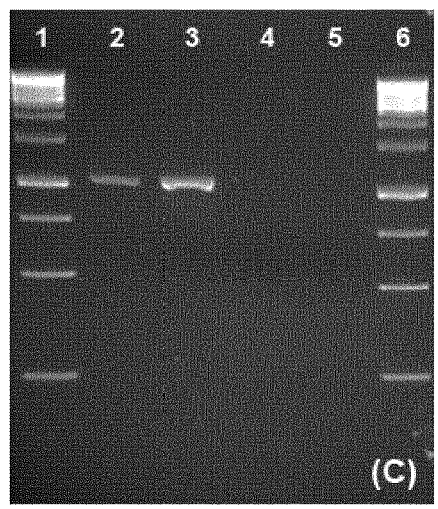
Figure 5:
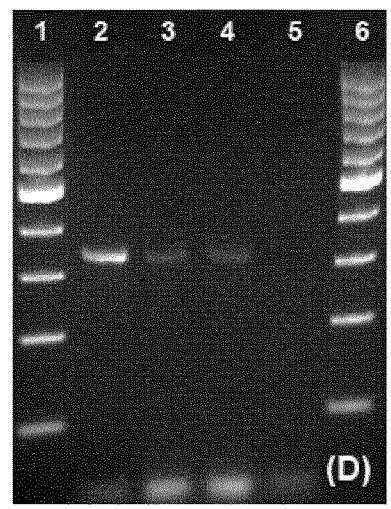

FIG. 5 shows the determination of plasmid and R-lactamase genes cfiA, cfxA and cepA. (A) Plasmid: 20 µg of each isolated plasmid DNA was loaded. Lanes: 1, 1 kb DNA ladder; 2, *E. coli* DSM 3876; 3, *E. coli* DSM 6202; 4, *Bacteroides xylanisolvens* DSM 25004. (B) cfiA gene: Lanes: 1, 100 bp DNA ladder; 2, *Bacteroides fragilis* TAL 3636; 3, *Bacteroides xylanisolvens* DSM 25004; 4, negative control. (C) cfxA gene: Lanes: 1 and 6, 1 kb DNA ladder; 2, *Bacteroides ovatus* MN7; 3, *Bacteroides ovatus* MN23; 4, *Bacteroides xylanisolvens* DSM 25004; 5, negative control. (D) cepA gene: Lanes: 1 and 6, 100 bp DNA ladder; 2, *Bacteroides fragilis* DSM 1396; 3, *Bacteroides ovatus* MN23; 4, *Bacteroides xylanisolvens* DSM 25004; Lane 5, negative control.

Figure 6:
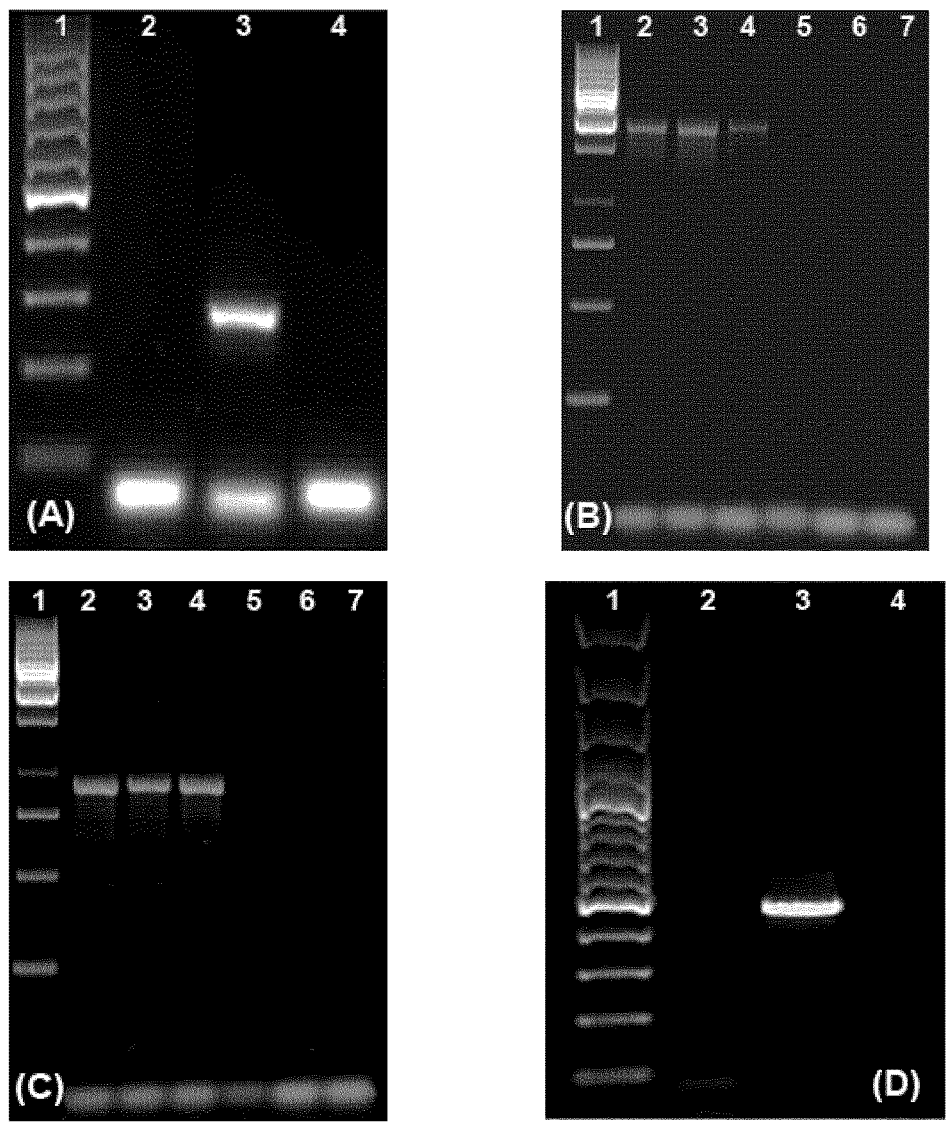

FIG. 6 shows the determination of virulence encoding genes bft, wcfR, wcfS, and ompW. (A) bft gene: Lanes: 1, 100 bp DNA ladder; 2, *Bacteroides xylanisolvens* DSM 25004; 3, *Bacteroides fragilis* ATCC 43858; 4, negative control. (B) wcfR gene: Lanes: 1, 1 kb DNA ladder; 2, *Bacteroides fragilis* DSM 1396; 3, *Bacteroides fragilis* ATCC 43858; 4, *Bacteroides fragilis* DSM 2151; 5, *Bacteroides xylanisolvens* DSM 25004; 6, *Bacteroides fragilis* TAL 3636; 7, negative control. (C) wcfS gene: Lanes: Lanes: 1, 1 kb DNA ladder; 2, *Bacteroides fragilis* DSM 1396; 3, *Bacteroides fragilis* ATCC 43858; 4, *Bacteroides fragilis* DSM 2151; 5, *Bacteroides xylanisolvens* DSM 25004; 6, *Bacteroides fragilis* TAL 3636; 7, negative control. (D) ompW gene: Lanes: 1, 100 bp DNA ladder; 2, *Bacteroides xylanisolvens* DSM 25004; 3, *Bacteroides caccae* DSM 19024; 4, negative control.

Figure 7:
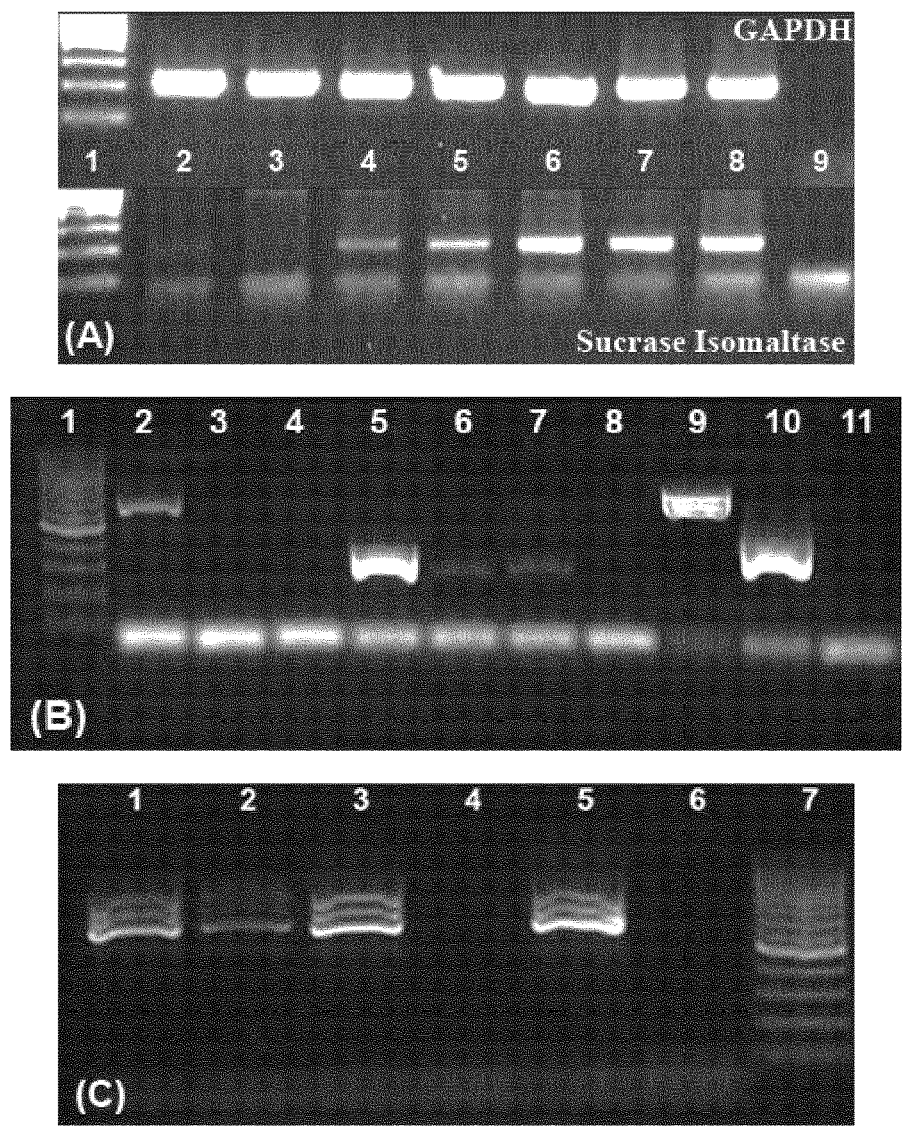

FIG. 7 shows the molecular analysis of the binding of strain DSM 25004 to Caco-2 cells. (A) GAPDH and sucrose isomaltase. Lanes: 1, 100 bp DNA ladder (Bioline); 2, $1^{th}$ day; 3, $3^{th}$ day; 4, $6^{th}$ day; 5, $8^{th}$ day; 6, $10^{th}$ day; 7, $13^{th}$ day; 8, $14^{th}$ day, 9, negative control. (B) Detection of strain DSM 25004 and *Bacteroides fragilis* DSM 1396. Lanes: 1, 100 bp DNA Ladder; 2, strain DSM 25004 after $1^{th}$ wash step; 3, strain DSM 25004 after $6^{th}$ wash step; 4, strain DSM 25004+Caco-2 cells; 5, *Bacteroides fragilis* DSM 1396 after $1^{th}$ wash step; 6, *Bacteroides fragilis* DSM 1396 after $6^{th}$ wash step; 7, *Bacteroides fragilis* DSM 1396+Caco-2 cells; 8, Caco-2 cells; 9, Strain DSM 25004; 10, *Bacteroides fragilis* DSM 1396; 11, negative control. (C) Detection of *Lactobacillus acidophilus*. Lanes: 1, *Lactobacillus acidophilus* DSM 9126 after $1^{th}$ wash step; 2, *Lactobacillus acidophilus* DSM 9126 after $6^{th}$ wash step; 3, *Lactobacillus acidophilus* DSM 9126+Caco-2 cells; 4, Caco-2 cells; 5, *Lactobacillus acidophilus* DSM 9126; 6, negative control; 7, 100 bp DNA Ladder.

Figure 8:
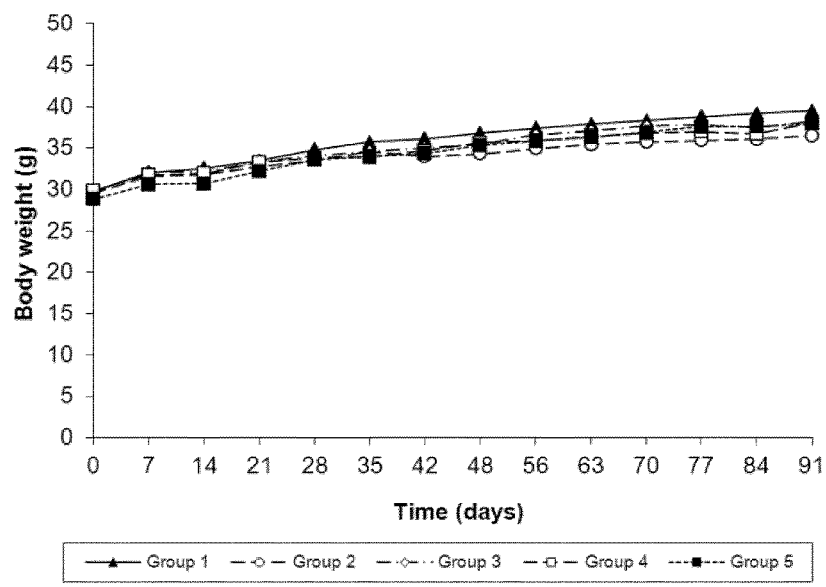
Figure 8:
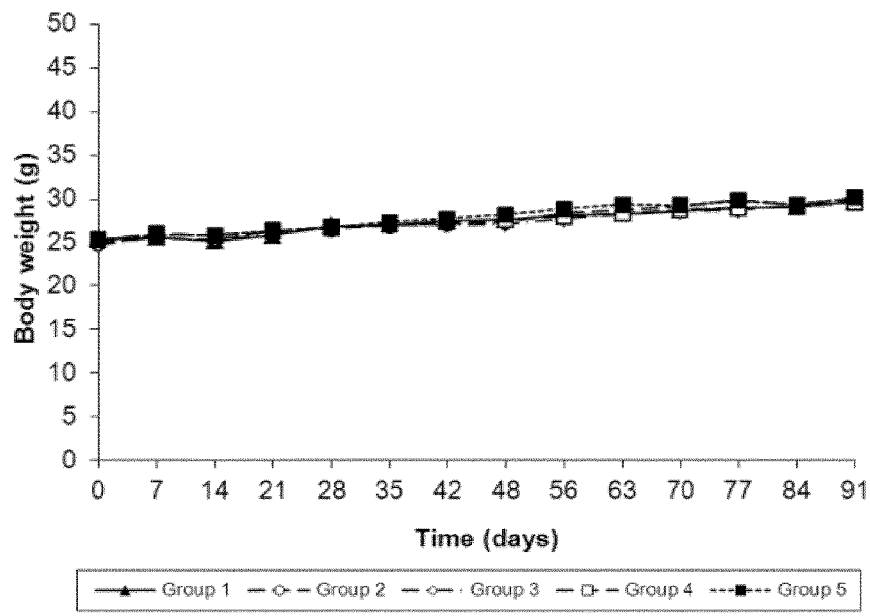
Figure 8:
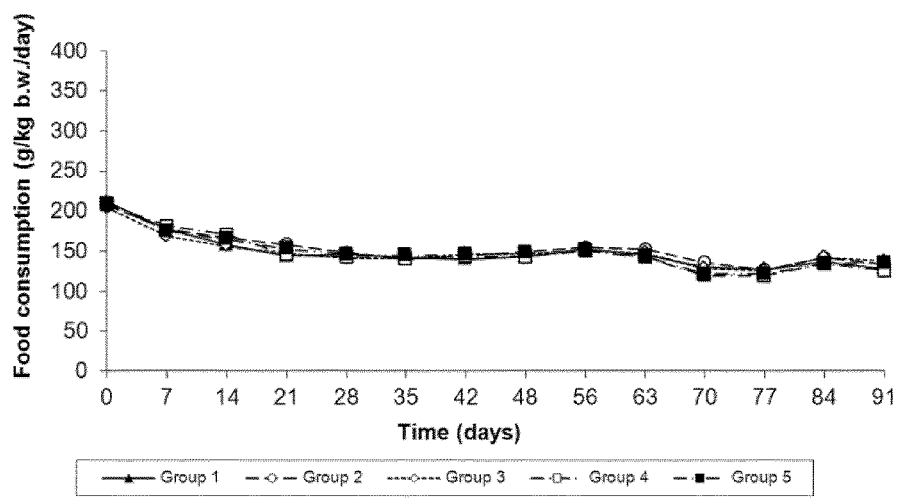
Figure 8:
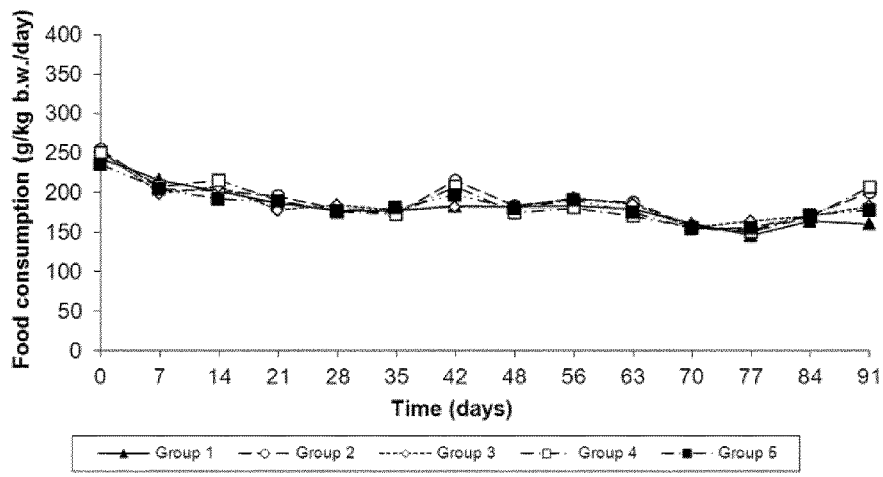

FIG. 8 shows the body weight and food consumption of mice during 90 days oral toxicity study. (A) Body weights of male Crl: NMRI mice. (B) Body weights of female Crl: NMRI mice. (C) Food consumption of male Crl: NMRI mice. (D) Food consumption of female Crl: NMRI mice. Mean values per group: Group1 (O), Group2 ($1 \times 10^6$), Group3 ($1 \times 10^7$), Group4 ($1 \times 10^8$) CFU's *Bacteroides xylanisolvens* DSM 25004 and Group5 ($1 \times 10^{11}$) *Bacteroides xylanisolvens* DSM 25004 pasteurized/animal/day. Statistical significance indicated by $P \leq 0.01$. Values accorded to Dunnett's test.

Figure 9:
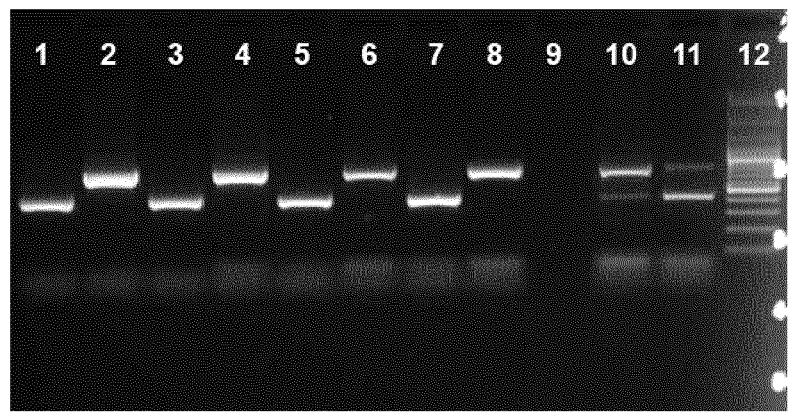

FIG. 9 shows the detection of contamination in injected solutions by multiplex species specific PCR. Lanes: 1, positive control (*Bacteroides xylanisolvens* DSM 25004); 2, Solution 2 ($1 \times 10^9$ *Bacteroides fragilis* RMA 6791/ml); 3, Solution 3 ($1 \times 10^9$ *Bacteroides xylanisolvens* DSM 25004/ml); 4, Solution 4 ($1.5 \times 10^8$ *Bacteroides fragilis* RMA 6791/ml); 5, Solution 5 ($1.5 \times 10^8$ *Bacteroides xylanisolvens* DSM 25004/ml); 6, Solution 6 ($5 \times 10^6$ *Bacteroides fragilis* RMA 6791/ml); 7, Solution 7 ($5 \times 10^6$ *Bacteroides xylanisolvens* DSM 25004/ml), 8, positive control (*Bacteroides fragilis* RMA 6791); 9, Solution 1 (control group). Contamination controls: Lane 10, mixture of 90% *Bacteroides fragilis* RMA 6791 and 10% *Bacteroides xylanisolvens* DSM 25004; Lane 11, mixture of 10% *Bacteroides fragilis* RMA 6791 and 90% *Bacteroides xylanisolvens* DSM 25004. Lane 12, 1 kb DNA Ladder (Fermentas).

Figure 10:
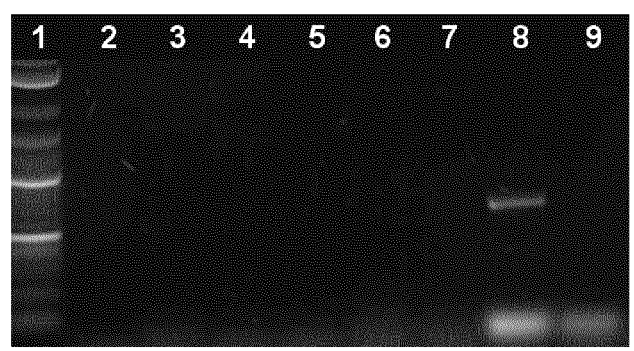
Figure 10:
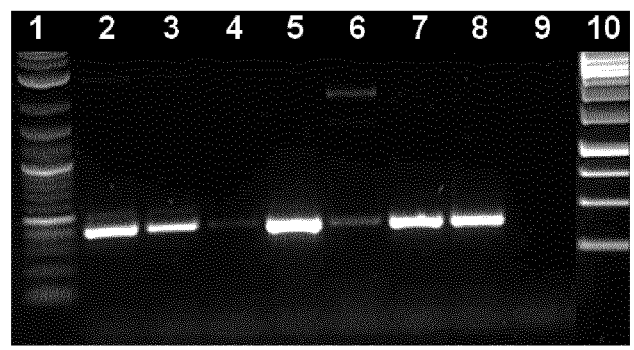

FIG. 10 shows the species specific PCR of isolated DNA from punctured abscesses. (A) Detection of *Bacteroides xylanisolvens* in abscesses of animals, which injected with *Bacteroides xylanisolvens* DSM 25004. Lanes: 1, 100 bp DNA Ladder (Fermentas); 2-3, Group 3 ($4.6 \times 10^9$ *Bacteroides xylanisolvens* DSM 25004/kg bw); 4-5, Group 5 ($6.9 \times 10^8$ *Bacteroides xylanisolvens* DSM 25004/kg bw); 6-7, Group 7 ($2.3 \times 10^7$ *Bacteroides xylanisolvens* DSM 25004/kg bw); 8, positive control (*Bacteroides xylanisolvens* DSM 25004); 9, negative control (water). (B) Detection of *Bacteroides fragilis* in abscesses of animals, which injected with *Bacteroides fragilis* RMA 6791. Lanes: 1, 100 bp DNA Ladder (Fermentas); 2-3, Group 2 ($4.6 \times 10^9$ *Bacteroides fragilis* RMA 6791/kg bw); 4-5, Group 4 ($6.9 \times 10^8$ *Bacteroides fragilis* RMA 6791/kg bw); 6-7, Group 6 ($2.3 \times 10^7$ *Bacteroides fragilis* RMA 6791/kg bw), 8, positive control (*Bacteroides fragilis* RMA 6791); 9, negative control (Water); 10, 1 kb DNA Ladder (fermentas).

EXAMPLES

Example 1: The Core-1 Positive Microorganism is a Distinct Strain of the Species *Bacteroides xylanisolvens*

1.1 Selective Enrichment and Isolation of Bacteria from Human Faecal Samples

For enrichment of core-1 positive bacteria from human faecal samples, magnetic beads coated with monoclonal antibodies specific for core-1 were prepared according to the manufacturer's recommendations (Dynal Biotech ASA, Oslo, Norway). Faecal samples from healthy human subjects who had not taken antibiotics during the last three months were used in the study. The faecal samples were diluted in reduced PBS ($PBS_{red}$: 8.5 g NaCl, 0.3 g $KH_2PO_4$, 0.6 g $Na_2HPO_4$, 0.1 g peptone and 0.25 g cysteine.HCl per L, pH 7.0), homogenized and centrifuged (300×g, 1 min, 21° C.). The supernatant was washed once (8000×g, 5 min, 21° C.) and re-suspended in $PBS_{red}$. A 20 µl volume of the bacterial suspension was added to 180 µl of $PBS_{red}$ and 5 µl of the antibody-coated magnetic beads, and the mixture incubated for 30 min at room temperature. Subsequently the beads were suspended in 1 ml $PBS_{red}$ and washed three times. Aliquots (100 µl) were spread on selective and non selective agar plated. Colonies were suspended in $PBS_{red}$ to McFarland turbidity standards 3 to 5 (Smibert and Krieg 1994), and a 20 µl aliquot of this suspension was again added to anti-core-1-antibody-coated beads. Colonies were picked randomly from agar plates and re-streaked several times on non-selective media. Colonies were cultured in appropriate broth medium under appropriate conditions. The cultures were partially frozen and partially fixed. The fixed cultures were used to assay the binding of the antibodies NM-TF1, NM-TF2 and B/A11-68 to each strain. Only the strain Coreotics did present an antibody binding profile similar to an immuno-accessible human core-1 structure, a strong and periodate sensitive binding of NM-TF1 and NM-TF2 and no binding of B/A11-68. The probable taxonomic affiliation of Coreotics to a bacteria species was characterized using biochemical assays (rapid ID 32A and API 20A biochemical Kits (Biomérieux, Marcy l'Etoile, France). As a result, Coreotics could be classified as belonging to the *Bacteroides* spp. group. To run further taxonomic analysis, a pure culture of Coreotics was obtained by plating a Coreotics culture on selective media and subsequently Step 1: selecting colonies presenting a homogeneous cell population under microscope,
Step 2: Out of step 1: selecting colonies presenting an adequate Core-1 expression (profile described above),
Step 3: Out of colonies selected in step 2: cultivating over night followed by plating of 200 to 500 colony forming units (cfu), and
Step 4: Selecting plates presenting a homogeneous population of colonies.

The selection process (steps 1 to 4) was repeated several times. After several purification rounds, the pure Coreotics strain was submitted to taxonomic analysis.

1.2 Taxonomic Analysis 1: 16S rRNA Sequence Similarity

The 16S rRNA gene sequence (480 bases) of strain Coreotics were amplified by PCR using universal primers 27f (5'-AGAGTTTGATCMTGGCTCAG-3' (SEQ ID NO: 20)) and 519r (5'-GWATTACCGCGGCKGCTG-3' (SEQ ID NO: 21)). PCR products were purified by using the High Pure PCR Product Purification Kit (Roche, Indianapolis, USA) and the DNA concentration and product size estimated by using a Low DNA Mass Ladder (Invitrogen, Carlsbad, USA). PCR products were sequenced using a DYEnamic™ ET Dye Terminator Cycle Sequencing Kit (Amersham Bioscience) and ABI PRISM 3100 capillary sequencer (Applied Biosystems) according to the manufacturer's specifications. The identification of phylogenetic neighbors was initially carried out by the BLAST (Altschul et al., 1997) and megaBLAST (Zhang et al., 2000) programs against the database of type strains with validly published prokaryotic names (Chun et al. 2007). The 50 sequences with the highest scores were then selected for the calculation of pairwise sequence similarity using global alignment algorithm, which was implemented at the EzTaxon server (www.eztaxon.org; Chun et al., 2007). The resulting multiple-sequence alignment was corrected manually by using the program MEGA version 5 (Tamura, 2007) to remove the alignment gaps and ambiguous bases and a phylogenetic tree was constructed according to the neighbor-joining method (Saitou & Nei, 1987) with the program MEGA version 5 (Tamura, 2007).

The 16S rRNA sequence analysis of strain Coreotics showed that this strain clustered with *Bacteroides xylanisolvens* DSM 18836 (100% 16S rRNA sequence similarity), with *Bacteroides ovatus* ATCC 8483 (97.5%), with *Bacteroides thetaiotaomicron* ATCC 29148 (94.2%) and with *Bacteroides finegoldii* DSM 17565 (92.2%). It is generally recognized that similarity values of 97% in 16S rRNA gene sequence divergence are significant for species delineation (Stackebrandt & Goebel, 1994). However, Stackebrandt & Ebers (2006) have made the recommendation that this value can be increased to 98.7-99% without sacrificing the quality and precision of a 'species' description, and as an aid to taxonomists.

1.3 Taxonomic Analysis 2: Whole Genome DNA-DNA Hybridization

DNA-DNA hybridization is considered the gold standard in taxonomy. The whole genome of the Coreotics strain was submitted to hybridization with the whole genome of *Bacteroides xylanisolvens* DSM 18836, *Bacteroides ovatus* DSM 1896, *Bacteroides thetaiotaomicron* DSM 2079 and *Bacteroides finegoldii* DSM 17565 (those analysis were run at and by the DMSZ (German Collection of Microorganisms and Cell Cultures). Briefly, 3 g biomaterial of each strain to be compared were used for DNA-preparation. Purity of the isolated DNA was analyzed and the DNA was sheared using a French press and denatured at high temperature (100° C., 10 min). The DNA is preferably sheared into fragments having a size of between 200 and 600 kDa, the main fraction being about 450+/−100 kDa. Renaturation of the DNA of each strain as well as of a mixture of DNA of both strains in equal concentrations (the final DNA concentrations in the samples is essentially identical and preferably lies between about 20 and 100 µg/ml, in particular about 30 µg/ml) was measured spectrophotometrically using the absorbance at 260 nm. Renaturation was initiated by quickly cooling the solution to a temperature 25° C. below the melting temperature of the DNA and the measurements were performed for 30 min. The DNA relatedness was calculated from the different slopes of the renaturation curves of the DNA of each of the single bacterial strain and the mixture of DNA of both strains. In particular, the renaturation rates v' were determined as decrease in absorbance/min (ΔA/t), and the degree of binding (D), i.e. the DNA relatedness, was calculated according to the formula given by De Ley et al. (see above):

$$D = \frac{4v'_m - (v'_A + v'_B)}{2\sqrt{v'_A v'_B}} 100$$

wherein D is the degree of binding (%), $v'_m$ is the renaturation rate of the mixture, $v'_A$ is the renaturation rate of the DNA of the first strain, and $v'_B$ is the renaturation rate of the DNA of the second strain.

Results of the whole genome hybridisation are shown in Table 1:

TABLE 1

| Reference strain | DNA relatedness to Coreotics |
|---|---|
| *Bacteroides xylanisolvens* DSM 18836 | 98.65% |
| *Bacteroides ovatus* DSM 1896 | 26.9% |
| *Bacteroides thetaiotaomicron* DSM 2079 | 28.65% |
| *Bacteroides finegoldii* DSM 17565 | 25.2% |

1.4 Taxonomic Analysis 3: Microbiological and Biochemical Characterization

The strain DSM 25004 could be identified to be strictly anaerobic, non-spore-forming, non-motile and Gram-negative. The short rods or rod-shaped cells were 0.4-0.5 μm in width and variable in length; generally in the range 1-2 μm. The grown colonies on Wilkins-Chalgren agar (Oxoid) after 18 h were 2-3 mm in diameter, with a circular, milky, raised, and convex surface. Initial biochemical analysis showed a 91% similarity to *Bacteroides ovatus* species (Databank Biomérieux). In contrast to *Bacteroides ovatus*, the strain DSM 23964 was unable to utilize starch, to produce indole, and it did not show catalase activity. The biochemical identification of isolated bacteria and their constitutive enzymes and substrate utilization profiles were performed by using rapid ID 32A and API 20A biochemical kits (Biomérieux, Marcy l'Etoile, France) according to the manufacturer's instructions. The results of chemotaxonomic analyses of strain *Bacteroides xylanisolvens* Coreotics, *Bacteroides xylanisolvens* DSM 18836, *Bacteroides finegoldii* DSM 17565, *Bacteroides ovatus* DSM 1896, *Bacteroides thetaiotaomicron* DSM 2079 and *Bacteroides fragilis* DSM 1396 are summarized in Table 2. Both strains *Bacteroides xylanisolvens* Coreotics and *Bacteroides xylanisolvens* DSM 18836 had identical biochemical profiles. *Bacteroides xylanisolvens* Coreotics could be differentiated from *Bacteroides ovatus* DSM 1896 by utilization of glycerol, D-sorbitol, D-mannitol and D-melezitose. In addition, *Bacteroides xylanisolvens* Coreotics showed glutamyl glutamic acid arylamidase activity, in contrast to the results for *Bacteroides ovatus* DSM 1896. On the other site, *Bacteroides ovatus* DSM 1896 was able to expressing leucine arylamidase activity, whereas *Bacteroides xylanisolvens* Coreotics did not. Therefore, *Bacteroides xylanisolvens* Coreotics could be differentiated from *Bacteroides finegoldii* DSM 17565, *Bacteroides thetaiotaomicron* DSM 2079 and *Bacteroides fragilis* DSM 1396 (Table 2). In contrast to the results for *Bacteroides xylanisolvens* Coreotics and *Bacteroides xylanisolvens* DSM 18836, *Bacteroides thetaiotaomicron* DSM 2079 showed a large number of positive results in tests for enzyme activities.

TABLE 2

| Biochemical characteristic | 1 | 2 | 3 | 4 | 5 | 6 |
|---|---|---|---|---|---|---|
| Indole formation | − | − | − | + | + | − |
| Enzymatic activities | | | | | | |
| N-Acetyl-β-Glucosaminidase | + | + | + | − | + | + |
| Glutamic acid Decarboxylase | + | + | + | − | + | + |
| α-Fucosidase | + | + | − | + | + | + |
| Indol production | − | − | − | + | + | + |
| Arginine arylamidase | − | − | − | − | + | − |
| Phenylalanine arylamidase | − | − | − | − | + | + |
| Leucine arylamidase | − | − | − | + | + | + |
| Tyrosine arylamidase | − | − | − | − | + | + |
| Glycine arylamidase | − | − | − | − | + | − |
| Histidine arylamidase | − | − | − | − | + | + |
| Glutamyl glutamic acid arylamidase | + | + | + | − | + | + |
| Serine arylamidase | − | − | − | − | + | − |
| Acid production from: | | | | | | |
| D-Mannitol | + | + | − | − | − | − |
| Salicin | + | + | + | + | − | − |
| Esculin hydrolysis | + | + | + | + | + | − |
| Glycerol | + | + | − | − | − | − |
| D-Melezitose | + | + | − | − | − | − |
| D-Sorbitol | + | + | − | − | + | − |
| D-Trehalose | + | + | − | + | + | − |
| Catalase activities | − | − | + | + | + | + |

Strains: 1: *Bacteroides xylanisolvens* Coreotics; 2: *Bacteroides xylanisolvens* DSM 18836; 3: *Bacteroides finegoldii* DSM 17565; 4: *Bacteroides ovatus* DSM 1896; 5: *Bacteroides thetaiotaomicron* DSM 2079; 6: *Bacteroides fragilis* DSM 1396. Characteristics are scored as: '+': positive reaction; '−': negative reaction.

1.5 Randomly Amplified Polymorphic DNA (RAPD) Pattern and Genotype Analysis

To test whether Coreotics is a distinct strain of the species *Bacteroides xylanisolvens*, a RAPD assay was performed. Four different random primers were used in separate reactions (using only one primer in each reaction) for amplification of template DNA. The PCR reaction mixture (50 μl) contained: Taq Buffer (16 mM $(NH_4)_2SO_4$, 67 mM Tris HCl), 2.5 mM $MgCl_2$, 0.25 mM each dNTP, 1 μM primer, 2.5 units Taq DNA polymerase and 2 μl of template DNA. The PCR program was: 95° C. for 5 min, 35 cycles of 95° C. for 1 min, 50° C. for 1 min and 72° C. for 1 min, and finally 72° C. for 6 min. Band patterns for all primers were analyzed on 1% agarose gels. Thus, for each template DNA, four different band patterns (one for each primer) were obtained.

The core-1-positive Coreotics was subjected to the RAPD analysis and the results were compared to that of reference bacteria of the species *Bacteroides xylanisolvens* (DSM 18836), *Baceroides finegoldii* (DSM 17565) and *Bacteroides ovatus* (DSM 1896) (see FIG. 1 for one exemplary primer). The results demonstrate that Coreotics is a distinct strain which is not identical to the known *Bacteroides xylanisolvens* strain DSM 18836.

1.6 Summary

The results of the 16S rRNA sequence similarity, the whole genome DNA-DNA hybridization and the biochemical characterization demonstrated that the isolated microorganism Coreotics is of the species *Bacteroides xylanisolvens*. Furthermore, the RAPD analysis showed that Coreotics is a specific and distinct *Bacteroides xylanisolvens* strain which is different from the known *Bacteroides xylanisolvens* strains.

Example 2: Stable and Homogeneous Expression of the Core-1 Antigen 2.1 Core-1 Expression of Coreotics Compared to AG6

Fixed bacterial cells were adjusted to a cell concentration of $1*10^7$ cell/ml with PBS. 50 µl were applied in duplicate to the wells of a PolySorp microtitre plate (Nunc, Wiesbaden, Germany) and coated overnight at 37° C. Prior to all further incubation steps, the plates were washed three times with 200 µl Tris-buffered saline with Tween 20 (8.78 g NaCl, 6.06 g Tris per L, and 0.05% [v/v] Tween 20, pH 7.6). The further method steps were performed at room temperature. Residual binding sites were blocked by incubating the wells with 200 µl of 2% bovine serum albumin (BSA) in PBS for 20 min. A monoclonal antibody specific for core-1 (Nemod-TF1) was applied as primary antibody in 50 µl 1% BSA containing PBS and incubated for 1 h at room temperature. The plates were washed three times with 200 µl Tris-buffered saline with Tween 20 before incubation with secondary antibody. The secondary antibody (peroxidase-rabbit-anti-mouse IgG/IgM P0260, DAKO, Hamburg, Germany) was diluted 1/5000 in 1% BSA in PBS, and 50 µl were applied per well and incubated for 1 h at room temperature. The plates were washed again three times with 200 µl Tris-buffered saline with Tween 20 and developed for 5 to 20 min in the dark by adding 100 µl of developing solution (1 mg/ml tetramethylbenzidine in 1% [v/v] DMSO in 50 µM sodium acetate buffer) to each well. Subsequently, 50 µl of 2.5 M $H_2SO_4$ was added to stop the reaction, and the absorbance ($E_{450/630}$) was measured in an ELISA Reader (Dynex Technologies Inc., Chantilly, Va., USA). A fixed culture of AG6 DSM 18726, disclosed in WO 2008/055703) also adjusted to a cell concentration of $1*10^7$ cell/ml with PBS served as positive control. Alternatively, asialoglycophorin and glycophorin (100 ng/well in PBS, Sigma-Aldrich, Taufkirchen, Germany) served as positive and negative controls for the core-1 antigen, respectively. The assays were performed in duplicate on at least two separate occasions.

ELISA assays of ten different Coreotics (DSM 25004) and 10 different AG6 (DSM 18726, disclosed in WO 2008/055703) colonies revealed that Coreotics (*Bacteroides xylanisolvens*) exhibits a very stable and homogeneous high core-1 expression on their cell surface while AG6 (*Bacteroides ovatus*) shows a higher variability and a lower average core-1 expression (see FIG. 2).

2.2 Core-1 Expression of Coreotics Compared to *B. xylanisolvens* Reference Strain The core-1 expression was analyzed by binding of the core-1 specific antibody Nemod-TF1 (Glycotope GmbH, Germany) in ELISA experiments. A strong TF1 binding could be identified for the positive control (PK) and the strain Coreotics. This revealed the presence of core-1 structures on their surface. The pre-treatment with periodate completely abolished the binding of the anti-core-1 antibody. The reference strain *Bacteroides xylanisolvens* DSM 18836 did not present any binding of the core-1 specific antibody. The results are shown in FIG. 3.

Example 3: Effect of Simulated Gastric Juice and Heat Treatments on the Core-1 Expression To simulate the passage through gastrointestinal tract, Coreotics bacteria were submitted to the action of simulated gastric and intestinal juices. The survivor rate for the Coreotics strain in gastric juice was above 90% after 180 min and above 96% after 240 min exposure to intestinal juice. Interestingly, none of the treatment had any effect on the core-1 antigen exposure on the surface of the strain Coreotics. Also pasteurization did not influence the core-1 antigen density that stayed stable over 12 months when stored at room temperature, 4 or −20° C.

Example 4: Production of Short Chain Fatty Acids

Based on HPLC analyses, it was demonstrated that the *Bacteroides xylanisolvens* strain CTC1 is able to produce short chain fatty acids (SCFAs) like propionate and acetate as well as other substances like succinate, formate and lactate. Depending on the growth conditions and medium composition the concentration of metabolic products measured in supernatant varied from 2.5 mM to 44.7 mM for succinate, 5.8 mM to 29.3 mM for propionate, 3.4 mM to 38.3 mM for acetate, 0 mM to 45 mM for formate and 0.88 mM to 8.6 mM for lactate, respectively.

Example 5: Analysis of Virulence Factors 5.1 Antibiotics Resistance of Coreotics The analysis of the minimum inhibitory concentration (MIC) of several antibiotics revealed that the *Bacteroides xylanisolvens* Coreotics strain was resistant to R-lactam drugs like penicillin G, ampicillin and meziocillin. However, it was sensitive to usual antibiotics agents like metronidazole, meropenem and clindamycin and the addition of R-lactamase inhibitor restored the sensitivity to R-lactam drugs.

5.2 Detection of Plasmids in Coreotics

To investigate the potential presence of plasmids in the Coreotics strain, plasmid DNA material was isolated from Coreotics and from both control strains, *E. coli* DSM 3876, and *E. coli* DSM 6202, respectively, which contain the low copy plasmids RP4 (60 kb) and pSC101 (9.4 kb). Measurements of the plasmid DNA concentration at 260 nm revealed no presence of DNA in the plasmid preparation of Coreotics. Running the plasmid preparations on an agarose gel confirmed the isolation of both low copy plasmids from the control strains and the absence of detectable plasmid material from *Bacteroides xylanisolvens* Coreotics (FIG. 5A).

5.3 Identification of the R-Lactamase Genes cfxA, cepA and cfiA in the Genome of Coreotics In order to characterize the R-lactamase activity of the Coreotics strain, specific PCR assays were run for each of the R-lactamase genes cfiA, cfxA, and cepA known for the genus *Bacteroides*. Results indicate that the strain Coreotics exclusively contains the cepA gene (FIG. 5B-D).

5.4 Genes Encoding Virulence Factors in the Genus *Bacteroides*

The *Bacteroides fragilis* Polysaccharide A (PS A) and the *Bacteroides fragilis* enterotoxin Bft are the most important virulence factors of the genus *Bacteroides*. In order to investigate the presence of the enterotoxin Bft, a specific PCR for the bft gene was performed. In case of PS A, specific PCRs for the highly conserved open reading frames upaY, upaZ, located upstream of the biosynthesis genes of PS A, and for the most important genes wcfR encoding an aminotransferase and wcfS encoding a glycosyltransferase were designed. In contrast to the *Bacteroides fragilis* ATCC 43858, the Coreotics strain does not possess the bft gene. Also the genes wcfR, wcfS and both open reading frames upaY and upaZ could not be detected (FIG. 6A-C).

Furthermore, the presence of the gene ompW encoding the virulence factor "Ton B-Linked outer membrane protein", which may be involved in the development of IBD was analyzed. No ompW encoding gene could be detected in the Coreotics strain (FIG. 6D).

5.5 Determination of Extracellular Enzymes and Pathogenic Factors of Coreotics

Besides neuraminidase, several strains of the genus *Bacteroides* were described to produce unwanted exoenzymes including collagenase, DNAse and some proteases that may participate in infection processes. The most relevant exoenzyme activities were analyzed by means of PCR (neuraminidase) or enzymatic assays. The Coreotics strain show no DNase, chondroitinase, hyaluronidase, and neuraminidase activities, and only weak R-hemolytic and collagenase activities.

5.6 Adhesion of Coreotics to Caco-2 Cells

Caco-2 cells were cultivated and differentiation was induced. The results demonstrate that the expression level of GAPDH was constant during differentiation, whereas the level of sucrase isomaltase increased during differentiation. Microscope observation confirmed that the Caco-2 cells were well differentiated as monolayer after 14 days. The binding of bacteria to differentiated Caco-2 cells after 3 hours of co-incubation under anaerobic conditions was analyzed by means of a species-specific PCR performed on supernatants of successive wash steps, and finally on the scraped Caco-2 cells. In contrast to positive controls, Coreotics cells, which of course could be detected in the supernatant of the first wash step, could no longer be detected in later supernatants or on scraped Caco-2 cells, indicating that the Coreotics cells do not attach to epithelial cells of the human colon (FIG. 7).

Example 6: Toxicological Studies 6.1 Viability Assay

The viability of *Bacteroides xylanisolvens* Coreotics (DSM 25004) after lyophilization and rehydration was analyzed in several independent experiments. The lowest identified survival rate indicated a minimum concentration of $4 \times 10^9$ CFU/g viable bacteria. This concentration was accepted as the "available concentration".

6.2 In Vitro Mutagenicity Study (Ames-Test)

This test was performed to detect any toxic or mutagenic effects of Coreotics or their fermentation products. Five doses of viable bacteria ranging from 0.28 to 28.5 mg bacteria/plate or one dose of 59 mg pasteurized bacteria/plate were employed in two independent experiments, each carried out with and without metabolic activation. No signs of cytotoxicity and no increase in revertant colony numbers as compared with control counts were observed for any concentration of the 5 test strains with and without metabolic activation, and also in both test formats, plate incorporation and pre-incubation mode, respectively.

6.3 In Vitro Assessment of the Clastogenic Activity (In Vitro Chromosomal Aberration Assay)

The top concentration of Coreotics employed in the study was 2.8 mg viable bacteria/ml culture medium and 5.9 mg pasteurized bacteria/ml culture medium, which were considered to be the maximum reasonable concentration. In the absence of metabolic activation, the mean incidence of chromosomal aberrations (excluding gaps) observed in the negative control was 1.0% or 0.5% after a 4-hour and 24-hour exposure, respectively. None of the concentrations of Coreotics, either viable or pasteurized, produced any statistically significant increase in aberrant cells after 4-hour and 24-hour exposure (0.5% to 2.5%). In contrast, the positive control presented a 10.5% and 17.5% increase in aberrant cells after a 4-hour and 24-hour exposure, respectively. In the presence of metabolic activation, the mean incidence of chromosomal aberrations (excluding gaps) observed in the negative control was 0.5% after a 4-hour exposure. Again, none of the concentrations of Coreotics either viable or pasteurized produced any statistically significant increase in aberrant cells, resulting in 0.0% and 1.5% in two independent experiments, respectively. The positive control presented 13.5% and 16.5% aberrant cells after a 4-hour in two experiments, respectively. For all Coreotics concentrations tested, no item-related polyploidy or endoreduplication was noted in the experiments with or without metabolic activation. Furthermore, confirming precedent results, no signs of cytotoxicity were noted at any tested concentration of Coreotics in the experiments with and without metabolic activation.

6.4 90-Day Oral Toxicity Study in Mice

The aim of this study was to determine whether the oral intake of Coreotics would have any toxicological effect. Crl: NMRI mice (50 male and 50 female) were allocated to 5 test groups (10 males and 10 females per group) and administrated daily doses of bacteria orally via gavage for 90 days. We tested the effect of $1 \times 10^6$ to $1 \times 10^8$ CFU or $1 \times 10^{11}$ pasteurized Coreotics per animal per day. Results are shown in FIG. 8. During the 90 test days no mortality was noted in any group treated with viable or pasteurized Coreotics, as in the control group. None of the mice treated or untreated revealed any changes in their behavior or external appearance. Furthermore, the functional observation did not reveal any test item-related influence: motility, faeces consistency, and water consumption, as well as body weight gain and food consumption presented no significant differences throughout the experimental period between the treated groups and with the control group. The hematological examination showed no test item-related influence at any of the tested dose levels of viable and pasteurized Coreotics, and no statistically significant differences between the control group and the groups of treated mice was observed. The clinical biochemistry values and the ophthalmological examination revealed no test item-related changes in any group at any dose level for both viable and pasteurized Coreotics. Further, macroscopic post-mortem analyses revealed no test item related lesions or abnormalities. Finally, an extensive and detailed histopathological analysis of all organs revealed no differences between the treated groups and with the control group.

6.5 In Vivo Pathogenicity of Coreotics (Abscess Formation)

The in vivo intraperitoneal abscess formation model is a well-accepted model to investigate the pathologic properties of opportunistic bacterial strains (McConville et al., 1981; Onderdonk et al. 1984; Thadepalli et al. 2001). Fresh overnight bacterial cultures of *Bacteroides fragilis* RMA 6971 or *Bacteroides xylanisolvens* DSM 25004 (Coreotics) were used. A mixture containing $2.3 \times 10^7$ to $4.6 \times 10^9$ CFU per kg body weight, 50% (w/w) autoclaved rat faeces, and 10% (w/v) barium sulfate was intraperitoneally injected into mice. The viability, bacterial concentration and purity of each item were determined retrospectively after injection on remaining material. In order to identify the presence of *Bacteroides fragilis* and/or *Bacteroides xylanisolvens*, a multiplex species specific PCR as described by Liu et al. (2003) was established. This multiplex PCR also allowed identifying both species in contamination situations where one species would be strongly underrepresented. We confirmed that each single test item contained the wanted bacterial strain and was not contaminated with the other species (see FIG. 9). Further potential contaminations were analyzed through plating each test item on appropriate agar and incubated it under aerobic conditions. No single colony could be detected after 48 hours of incubation. In two separate experiments, mice injected with a high dose of Coreotics did not induce the development of more or bigger abscesses as the negative control (Barium sulfate+sterile rat faeces). In contrast, high concentrations of *Bacteroides fragilis* RMA 6971 induced the formation of more and bigger abscesses. After 7 days, 2 abscesses per animal were taken under sterile conditions, the content punctured and submitted to DNA extraction. We evaluated the presence of Coreotics or *Bacteroides fragilis* RMA 6791 in the abscesses by means of species-specific PCRs (FIG. 10). *Bacteroides fragilis* RMA 6971 could be detected in all abscesses isolated from groups 2, 4 and 6 injected with $2.3 \times 10^7$ to $4.6 \times 10^9$ *Bacteroides fragilis* per kg body weight, respectively. In contrast, independent of the bacterial concentration injected, Coreotics could not be detected in any of the analyzed abscesses. These results for injected mice with Coreotics clearly indicated that this strain does not induce the formation of abscesses, and that it is actually quickly and completely eradicated by the immune system after i.p. injection.

Example 7: Mouse Model

Mice sera may contain antibodies cross-reacting with carbohydrate structures. Following immunization, an increased binding observed on any core-1 carrier molecule or cell may as well be related to such cross-reacting antibodies, leading to false positive signals. In order to specifically analyze the core-1-specific antibody titer, the level of core-1 specific antibody at each time point was expressed as the ratio: "Core-$1_R$=signal on carrier-core-1/signal on carrier-ref". The reference structure may be any carbohydrate structure not present on the surface of Coreotics, preferably a disaccharide. An increase in the ratio following administration of Coreotics indicates an increase in core-1 specific antibody titer.

Male C3H mice aged 7 to 9 weeks were orally administered with $5*10^9$ Coreotics a day for a period of 4 weeks. As negative control, 4 mice were treated with NaCl and 4 mice were treated with the core-1-negative strain *B. ovatus* DSM 1896. Sera were taken before starting immunization and at day 21 and day 28. The sera were diluted 1/100 and their content in core-1 specific IgM antibody analyzed on glycoconjugates PAA-core-1 and PAA-ref (Galβ1-3GlcNAc) as follows.

The glycoconjugates polyacrylamid-Galβ1-3GalNAc (PAA-core-1) and polyacrylamid-Galβ1-3GlcNAc (PAA-ref) were adjusted to a concentration of 5 μg/ml in coating puffer (4.2 g $NaHCO_3$, 1.78 g $Na_2CO_3$ ad 1 L with Millipore-$H_2O$, pH 9.6). 50 μl of each glycoconjugate were applied in duplicate to the wells of a MaxiSorp microtiter plate (Nunc, Wiesbaden, Germany) and coated overnight at 4° C. Prior to all further incubation steps, the plates were washed three times with 200 μl Tris-buffered saline with Tween 20 (8.78 g NaCl, 6.06 g Tris per L, and 0.05% [v/v] Tween 20, pH 7.6). Residual binding sites were blocked by incubating the wells with 200 μl of 2% bovine serum albumin (BSA) in PBS for 20 min.

Animal sera were appropriately diluted (1/50 to 1/200) with 1% BSA containing PBS and 50 μl were applied in duplicate on wells coated with PAA-core-1 and PAA-ref and incubated for 1 h at room temperature. The plates were washed three times with 200 μl Tris-buffered saline with Tween 20 before incubation for 1 h with 50 μl of a 1/5000 dilution in 1% BSA in PBS of the secondary antibody (peroxidase-goat-anti-mouse IgM 115-035-075, Jackson ImmunoResearch). The plates were washed again three times with 200 μl Tris-buffered saline with Tween 20 and developed for 5 to 20 min in the dark by adding 100 μl of developing solution (1 mg/ml tetramethylbenzidine in 1% [v/v] DMSO in 50 μM sodium acetate buffer) to each well. Subsequently, 50 μl of 2.5 M $H_2SO_4$ was added to stop the reaction, and the absorbance ($E_{450/630}$) was measured. The level of core-1 specific antibody was expressed as the ratio: "$E_{450/630}$ on PAA-core-1/$E_{450/630}$ on PAA-ref". Comparing the ratio before and after immunization allowed to specifically analyzing the change in core-1 specific antibody titer.

As a result, the induction of a core-1 specific antibody titer in mice by the *Bacteroides xylanisolvens* strain CTC1 could be shown. Thus, it was demonstrated that the microorganisms according to the invention are capable of inducing an immune response against the core-1 antigen.

The invention claimed is:

1. An isolated pasteurized or lyophilized core-1 positive microorganism of the species *Bacteroides xylanisolvens*, wherein said microorganism is recognized by at least one core-1 specific antibody; wherein said core-1 positive microorganism is of the strain Coreotics, deposited as DSM 25004, a microorganism derived therefrom or a homolog thereof, wherein the microorganism derived from the strain Coreotics or the homolog of the strain Coreotics has the following characteristics:
   a) it belongs to the species of *Bacteroides* xylanisolvens; and
   b) in a cell culture of said microorganism, at least 50% of the microorganisms have a core-1 antigen expression level which is at least 50% of the average core-1 antigen expression of the strain Coreotics.

2. The microorganism according to claim 1, wherein the microorganism is the strain Coreotics deposited as DSM 25004.

3. The microorganism according to claim 1, wherein the microorganism derived from the strain Coreotics or the Coreotics homolog has two or more of the following characteristics:
   a) in a DNA-DNA hybridization assay, it shows a DNA-DNA relatedness of at least 50% with the strain Coreotics deposited as DSM 25004;
   b) it displays a level of 16S rRNA gene sequence similarity of at least 98% with the strain Coreotics deposited as DSM 25004; and/or
   c) it shows a core-1 antigen expression which has one or more of the following characteristics:
      i) it achieves on average an absorbance value of at least 0.3 in an ELISA assay;
      ii) it expresses on the cell surface at least one carbohydrate structure selected from the group consisting of the following structures:

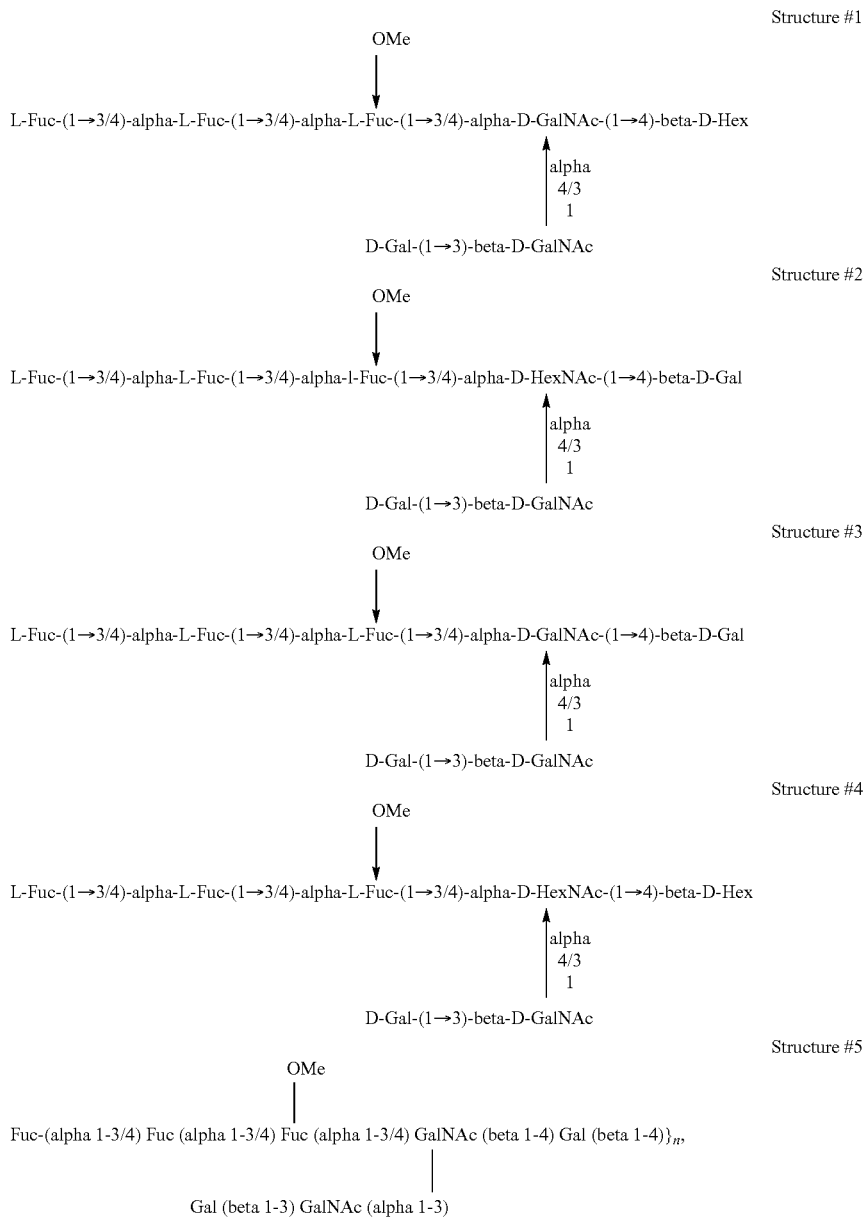

analogous structures thereof, and/or repeating units thereof;

iii) in a cell culture of said microorganism, at least 50% of said microorganisms have a core-1 antigen expression level which is at least 75% of the average core-1 antigen expression of the strain Coreotics deposited as DSM 25004; and/or iv) in a cell culture of said microorganism, at least 50% of said microorganisms have a core-1 antigen expression level which is in the range of from 70% to 150% of the average core-1 antigen expression of the strain Coreotics deposited as DSM 25004.

4. The microorganism of claim 1, wherein the microorganism is recognized and thus bound by at least one core-1 specific antibody when the core-1 specific antibody is contacted with the microorganism under appropriate binding conditions, wherein said binding of the core-1 specific antibody to the microorganism fulfills one or more of the following characteristics:

a) the core-1 specific antibody is selected from the group consisting of the following antibodies:

i) an antibody comprising a heavy chain variable region CDR1 comprising SEQ ID NO:1, a heavy chain variable region CDR2 comprising SEQ ID NO:2, a heavy chain variable region CDR3 comprising SEQ ID NO:3, a variable region CDR2 comprising SEQ ID NO:5, and a light chain variable region CDR3 comprising SEQ ID NO:6, ii) an antibody comprising a heavy chain variable region CDR1 comprising SEQ ID NO:7, a heavy chain variable region CDR2 comprising SEQ ID NO:8, a heavy chain variable region CDR3 comprising SEQ ID NO:9, a light chain variable region CDR1 comprising SEQ ID NO:10, a light chain variable region CDR2 comprising SEQ ID NO:11, and a light chain variable region CDR3 comprising SEQ ID NO:12,
iii) the antibody Nemod-TF1, and
iv) the antibody Nemod-TF2;
b) the microorganism is bound by at least two core-1 specific antibodies, wherein said at least two different antibodies recognize different epitopes;
c) binding of the at least one core-1 specific antibody to the microorganism is periodate sensitive in that the binding is reduced or absent after periodate treatment; and/or
d) the microorganism comprises the core-1 antigen in an exposed form, wherein said exposed core-1 antigen are not masked by other structures.

5. A composition comprising isolated pasteurized or lyophilized core-1 positive microorganisms according to claim 1.

6. The composition according of claim 5, wherein at least 50% of the core-1 positive microorganisms in the composition have a core-1 antigen expression level which is
a) at least 75% of the average core-1 antigen expression level of all core-1 positive microorganisms in the composition, and/or at least 75% of the average core-1 antigen expression of Coreotics deposited as DSM 25004; and/or
b) in the range of from 70% to 150% of the average core-1 antigen expression level of all core-1 positive microorganisms in the culture, and/or in the range of from 70% to 150% of the average core-1 antigen expression of Coreotics deposited as DSM 25004.

7. A method of inducing and/or enhancing an immune response against the core-1 antigen by administering the composition of claim 5.

8. A method of treating core-1 positive tumors, cancers, gastrointestinal disorders and/or core-1 positive diseases by administering the core-1 positive microorganism or a core-1 positive lysate thereof or a core-1 positive fraction thereof of claim 1.

9. A method for manufacturing a core-1 positive product, comprising the following steps:
a) providing the core-1 positive microorganism or a core-1 positive lysate thereof or a core-1 positive fraction thereof of claim 1, and
b) using said core-1 positive microorganism and/or said core-1 positive lysate or fraction thereof in the manufacture of the core-1 positive product.

10. The method according to claim 9, wherein the core-1 positive product is an antigen presenting cell and wherein step c) comprises loading said antigen presenting cell with said core-1 positive microorganism and/or said core-1 positive lysate or fragment thereof.

11. A composition comprising microorganisms, wherein at least 90% of the microorganisms are (A) core-1 positive microorganisms of the strain Coreotics, deposited as DSM 25004, microorganisms derived therefrom or homologs thereof, and/or (B) a core-1 positive lysate thereof or a core-1 positive fraction thereof;

wherein the microorganisms derived from the strain Coreotics or the homologs of the strain Coreotics have the following characteristics:
a) they belong to the species of *Bacteroides* xylanisolvens; and
b) in a cell culture of said microorganism, at least 50% of the microorganisms have a core-1 antigen expression level which is at least 50% of the average core-1 antigen expression of the strain Coreotics;

and wherein the core-1 positive fraction of the microorganism is selected from the group consisting of a cell wall preparation, an envelope preparation, a lipopolysaccharide preparation, a capsule preparation and a capsule polysaccharide preparation.

12. A method of inducing and/or enhancing an immune response against the core-1 antigen by administering the composition of claim 11.

* * * * *